US011208656B2

(12) United States Patent
Heineke et al.

(10) Patent No.: US 11,208,656 B2
(45) Date of Patent: Dec. 28, 2021

(54) INCRNAS GADLOR 1 AND 2 FOR USE IN TREATING AND PREVENTING CARDIAC REMODELLING

(71) Applicant: MEDIZINISCHE HOCHSCHULE HANNOVER, Hannover (DE)

(72) Inventors: Jörg Heineke, Hannover (DE); Natali Froese, Hannover (DE)

(73) Assignee: MEDIZINISCHE HOCHSCHULE HANNOVER, Hannover (DE)

( * ) Notice: Subject to any disclaimer, the term of this patent is extended or adjusted under 35 U.S.C. 154(b) by 101 days.

(21) Appl. No.: 16/616,398

(22) PCT Filed: May 30, 2018

(86) PCT No.: PCT/EP2018/064226
§ 371 (c)(1),
(2) Date: Nov. 22, 2019

(87) PCT Pub. No.: WO2018/220038
PCT Pub. Date: Dec. 6, 2018

(65) Prior Publication Data

US 2020/0140860 A1 May 7, 2020

(30) Foreign Application Priority Data

May 31, 2017 (EP) .................................... 17173818

(51) Int. Cl.
*C12N 15/113* (2010.01)
*C12Q 1/68* (2018.01)

(52) U.S. Cl.
CPC ...... *C12N 15/113* (2013.01); *C12N 2310/113* (2013.01); *C12N 2310/14* (2013.01); *C12N 2320/10* (2013.01)

(58) Field of Classification Search
None
See application file for complete search history.

(56) References Cited

U.S. PATENT DOCUMENTS

| | | | |
|---|---|---|---|
| 4,946,778 | A | 8/1990 | Ladner et al. |
| 6,080,560 | A | 6/2000 | Russell et al. |
| 2004/0175699 | A1 | 9/2004 | Fiszman et al. |

FOREIGN PATENT DOCUMENTS

| | | |
|---|---|---|
| WO | WO 2011/157294 A1 | 12/2011 |
| WO | WO 2018/220038 A1 | 12/2018 |

OTHER PUBLICATIONS

"International Search Report and Written Opinion dated Jul. 4, 2018 in International Patent Application No. PCT/EP2018/064226, filed on May 30, 2018", 18 pages.

Alexander, et al., "Exosome-Delivered MicroRNAs Modulate the Inflammatory Response to Endotoxin", Nature Communications, 2015, 6(7321): 16 pages.

Allay, et al., "Good Manufacturing Practice Production of Self-Complementary Serotype 8 Adeno-Associated Viral Vector for a Hemophilia B Clinical Trial", Human Gene Therapy, 2011, 22(5):595-604.

Altshuler, et al., "Generation of Recombinant Antibodies and Means for Increasing their Affinity", Biochemistry (Moscow), Dec. 2010, 75(13):1584-1605.

Appari, et al., "C1q-TNF-Related Protein-9 Promotes Cardiac Hypertrophy and Failure", Circulation Research, Jan. 6, 2017, 120(1):66-77.

Ausubel, et al., "Current Good Manufacturing Practice Production of an Oncolytic Recombinant Vesicular Stomatitis Viral Vector for Cancer Treatment", Human Gene Therapy, 2011, 22(4):489-497.

Bang, et al., "Cardiac Fibroblast-Derived MicroRNA Passenger Strand-Enriched Exosomes Mediate Cardiomyocyte Hypertrophy", Journal of Clinical Investigation, 2014, 124(5):2136-2146.

Bebbington, et al., "High-level Expression of a Recombinant Antibody from Myeloma Cells Using A Glutamine Synthetase Gene As an Amplifiable Selectable Marker", Bio/Technology, Feb. 1992, 10(2):169-175.

Borlaug, et al., "Heart Failure with Preserved Ejection Fraction: Pathophysiology, Diagnosis, and Treatment", European Heart Journal, 2011, 32(6):670-679.

Braz, et al., "Targeted Inhibition of P38 MAPK Promotes Hypertrophic Cardiomyopathy through Upregulation of Calcineurin-NFAT Signaling", Journal of Clinical Investigation, 2003, 111(10):1475-1486.

Bustin, SA, "Quantification of mRNA Using Real-Time Reverse Transcription PCR (RT-PCR): Trends and Problems", Journal of Molecular Endocrinology, 2002, 29(1):23-39.

Caley, et al., "Long Noncoding RNAs, Chromatin, and Development", The Scientific World Journal, 2010, 10:90-102.

Calza, et al., "Normalization of Gene-Expression Microarray Data", Methods in Molecular Biology, 2010, 673:37-52 (abstract only).

Charles, et al., "Pituitary-Specific Gata2 Knockout: Effects on Gonadotrope and Thyrotrope Function", Molecular Endocrinology, Jun. 2006, 20(6):1366-1377.

Chen, et al., "Abnormalities of Capillary Microarchitecture in a Rat Model of Coronary Ischemic Congestive Heart Failure", American Journal of Physiology, 2015, 308(8):H830-H840.

De Fougerolles, et al., "siRNA and the Lung: Research Tool or Therapeutic Drug?", Current Opinion in Pharmacology, 2008, 8(3):280-285.

Debosch, et al., "Akt1 Is Required for Physiological Cardiac Growth", Circulation, 2006, 113(17):2097-2104.

(Continued)

*Primary Examiner* — Sean McGarry
(74) *Attorney, Agent, or Firm* — Grant IP, Inc.

(57) ABSTRACT

The present invention relates to a compound inhibiting the expression and/or the activity of a long non-coding RNA (lncRNA) selected from GADLOR 1 and GADLOR 2 for use in treating or preventing cardiac remodelling, wherein GADLOR 1 comprises or consists of a nucleic acid sequence selected from the group consisting of SEQ ID NOs 1 to 3 and sequences being at least 75% identical thereto, and GADLOR 2 comprises or consists of a nucleic acid sequence selected from the group consisting of SEQ ID NOs 4 to 6 and sequences being at least 75% identical thereto.

13 Claims, 22 Drawing Sheets

Figure 1:
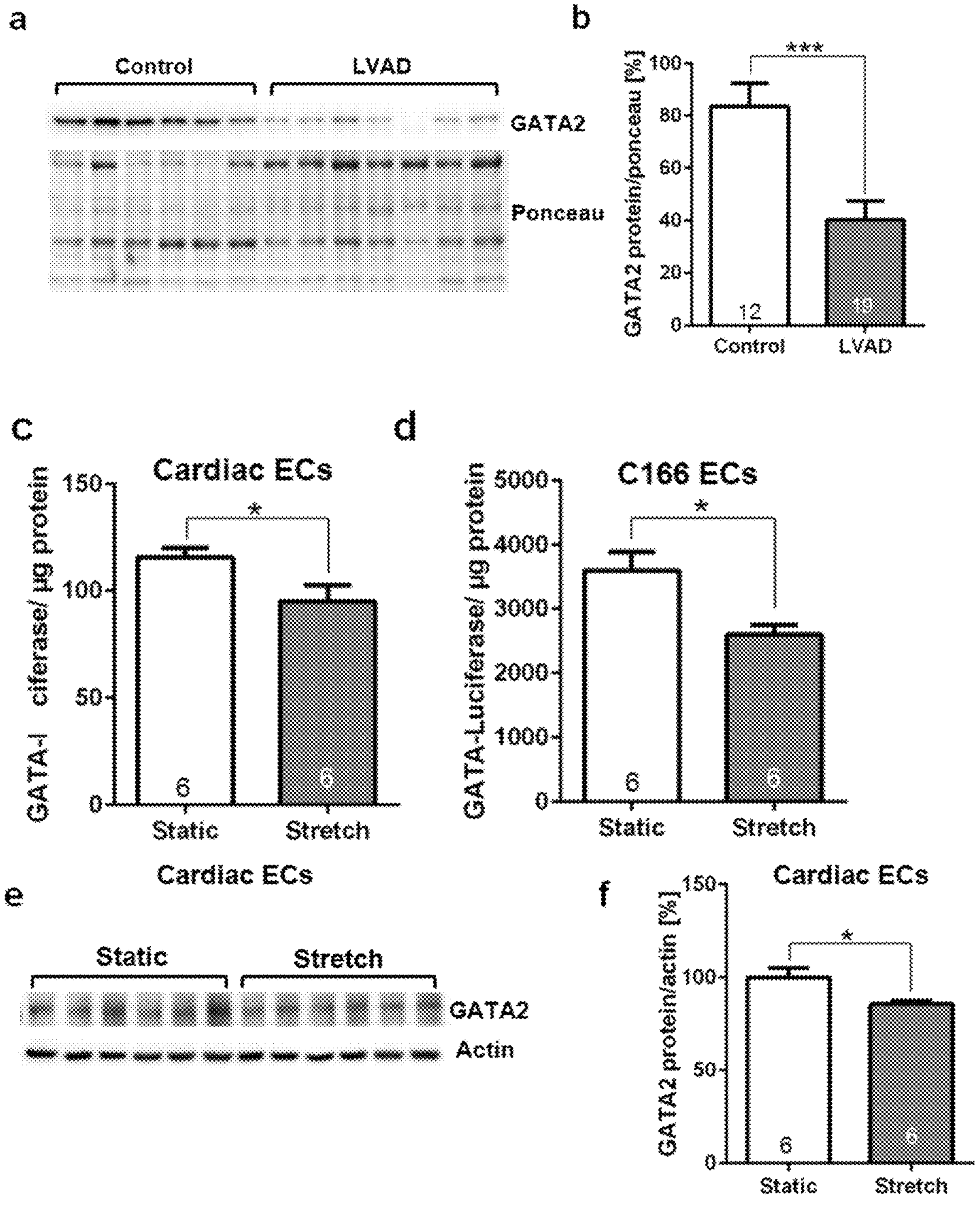

Specification includes a Sequence Listing.

(56) References Cited

OTHER PUBLICATIONS

Doetschman, et al., "Cardiac-Specific Inducible and Conditional Gene Targeting in Mice", Circulation Research, May 2012, 110(11):1498-1512.
Elbashir, et al., "Duplexes of 21-Nucleotide RNAs Mediate RNA Interference in Cultured Mammalian Cells", Nature, May 2001, 411 (6836):494-498.
Esau, et al., "MicroRNA-143 Regulates Adipocyte Differentiation", The Journal of Biological Chemistry, Oct. 25, 2004, 279(50):52361-52365.
Feyder, et al., "Investigating Long Noncoding RNAs Using Animal Models", Journal of Clinical Investigation, 2016, 126(8):2783-2791.
Fiedler, et al., "MicroRNA-24 Regulates Vascularity After Myocardial Infarction", Circulation, 2011, 124(6):720-730.
Forde, et al., "Temporal Cre-Mediated Recombination Exclusively in Endothelial Cells Using Tie2 Regulatory Elements", Genesis, 2002, 33(4):191-197.
Franco, et al., "Eplerenone Prevents Adverse Cardiac Remodeling Induced by Pressure Overload in Atrial Natriuretic Peptide-Null Mice", Clinical and Experimental Pharmacology and Physiology, 2006, 33(9):773-779.
Frey, et al., "Cardiac Hypertrophy: The Good, the Bad, and the Ugly", Annual Review of Physiology, Feb. 2003, 65(1-2):45-79.
Froese, et al., "GATA6 Promotes Angiogenic Function and Survival in Endothelial Cells by Suppression of Autocrine Transforming Growth Factor β/Activin Receptor-like Kinase 5 Signaling", Journal of Biological Chemistry, 2011, 286(7):5680-5690.
Gao, et al., "Transcriptome Complexity in Cardiac Development and Diseases", Circulation Journal, 2014, 78(5):1038-1047.
Gene Expression Omnibus, "Endothelial Cells Modulate the Cardiac Stress Response via Two Secreted IncRNAs", Accession: GSE93596, Dec. 31, 2017.
Ghahroudi, et al., "Selection and Identification of Single Domain Antibody Fragments from Camel Heavy-Chain Antibodies", FEBS Letters, 1997, 414:521-526.
Gibbings, et al., "Multivesicular Bodies Associate with Components of Mirna Effector Complexes and Modulate miRNA Activity", Nature Cell Biology, Sep. 2009, 11(9):1143-1149.
Gonzalo-Calvo, et al., "Circulating Long-Non Coding RNAs As Biomarkers of Left Ventricular Diastolic Function and Remodelling in Patients with Well-Controlled Type 2 Diabetes", Scientific Reports, Nov. 22, 2016, 6(1):12 pages.
Grote, et al., "The Tissue-Specific IncRNA Fendrr is an Essential Regulator of Heart and Body Wall Development in the Mouse", Developmental Cell, Jan. 28, 2013, 24(2):206-214.
Halkein, et al., "MicroRNA-146a is a Therapeutic Target and Biomarker for Peripartum Cardiomyopathy", Journal of Clinical Investigation, 2013, 123(5):2143-2154.
Han, et al., "A Long Non-Coding RNA Protects the Heart from Pathological Hypertrophy", Nature, 2014, 514(7520):102-106.
Haq, et al., "Differential Activation of Signal Transduction Pathways in Human Hearts With Hypertrophy Versus Advanced Heart Failure", Circulation, 2001, 103(5):670-677.
Heineke, et al., "Attenuation of Cardiac Remodeling after Myocardial Infarction by Muscle LIM Protein-Calcineurin Signaling at the Sarcomeric Z-Disc", Proceedings of the National Academy of Sciences, 2005, 102(5):1655-1660.
Heineke, et al., "Cardiomyocyte GATA4 Functions as a Stress-Responsive Regulator of Angiogenesis in the Murine Heart", Journal of Clinical Investigation, Dec. 2007, 117(11):3198-3210.
Heineke, et al., "CIB1 is a Regulator of Pathological Cardiac Hypertrophy", Nature Medicine, 2010, 16(8):872-879.
Heineke, et al., "Regulation of Cardiac Hypertrophy by Intracellular Signalling Pathways", Nature Reviews Molecular Cell Biology, 2006, 7(8):589-600.
Heineke, Joerg, "Wag the Dog: How Endothelial Cells Regulate Cardiomyocyte Growth", Arteriosclerosis, Thrombosis, and Vascular Biology, 2012, 32(3):545-547.
Hill, et al., "Cardiac Plasticity", The New England Journal of Medicine, Mar. 27, 2008, 358:1370-1380.
Holliger, et al., "Engineered Antibody Fragments and The Rise of Single Domains", Nature Biotechnology, Oct. 2005, 23(9):1126-1135.
Ishii, et al., "Identification of a Novel Non-Coding RNA, MIAT, that Confers Risk of Myocardial Infarction", Journal of Human Genetics, 2006, 51(12):1087-1099.
Izumiya, et al., "Vascular Endothelial Growth Factor Blockade Promotes the Transition from Compensatory Cardiac Hypertrophy to Failure in Response to Pressure Overload", Hypertension, May 2006, 47(5):887-893.
Johnson, et al., "Cis-Element Mutated in GATA2-Dependent Immunodeficiency Governs Hematopoiesis and Vascular Integrity", Journal of Clinical Investigation, 2012, 122(10):3692-3704.
Klattenhoff, et al., "Braveheart, A Long Non-Coding RNA Required for Cardiovascular Lineage Commitment", Cell, Jan. 31, 2013, 152(3):570-583.
Kogure, et al., "Extracellular Vesicle-Mediated Transfer of a Novel Long Noncoding RNA TUC339: A Mechanism of Intercellular Signaling in Human Hepatocellular Cancer", Genes Cancer, 2013, 4(7-8):261-272.
Kohler, et al., "Continuous Cultures of Fused Cells Secreting Antibody of Predefined Specificity", Nature, 1975, 256:495-497.
Korostowski, et al., "The Kcnq1ot1 Long Non-Coding RNA Affects Chromatin Conformation and Expression of Kcnq1, but does not Regulate Its Imprinting in the Developing Heart", PLOS Genetics, Sep. 2012, 8(9):12 pages.
Kozbor, et al., "The Production of Monoclonal Antibodies from Human Lymphocytes", Immunology Today, 1983, 4(3):72-79.
Kumarswamy, et al., "Circulating Long Noncoding RNA, LIPCAR, Predicts Survival in Patients with Heart Failure", Circulation Research, 2014, 114(10):1569-1575.
Li, et al., "Plasma Long Noncoding RNA Protected by Exosomes as a Potential Stable Biomarker for Gastric Cancer", Tumor Biology, 2015, 36(3):2007-2012.
Lim, et al., "Conditional GATA2 Inactivation Results in HSC Loss and Lymphatic Mis patterning", The Journal of Clinical Investigation, Oct. 2012, 122(10):3705-3717.
Lim, et al., "Isolation and Culture of Murine Heart and Lung Endothelial Cells for in Vitro Model Systems", Methods in Molecular Biology, 2006, 341:141-154.
Lin, et al., "The LINK-A IncRNA Activates Normoxic HIF1α Signaling in Triple-negative Breast Cancer", Nature Cell Biology, Feb. 2016, 18(2):213-224.
Linnemann, et al., "Genetic Framework for GATA Factor Function in Vascular Biology", Proceedings of the National Academy of Sciences, Aug. 16, 2011, 108(33): 13641-13646.
Liu, et al., "LncRNA NBR2 Engages a Metabolic Checkpoint by Regulating AMPK Under Energy Stress", Nature Cell Biology, 2016, 18(4):431-442.
Mai, et al., "Dyssynchronous Pacing Triggers Endothelial-Mesenchymal Transition through Heterogeneity of Mechanical Stretch in a Canine Model", Circulation Journal, Jan. 2015, 79(1):201-209.
Maillet, et al., "Heart-specific Deletion of CnB1 Reveals Multiple Mechanisms Whereby Calcineurin Regulates Cardiac Growth and Function", Journal of Biological Chemistry, 2010, 285(9):6716-6724.
Mammoto, et al., "A Mechanosensitive Transcriptional Mechanism that Controls Angiogenesis", Nature, Mar. 2009, 457(7233):1103-1108.
Matkovich, et al., "Epigenetic Coordination of Embryonic Heart Transcription by Dynamically Regulated Long Noncoding RNAs", Proceedings of the National Academy of Sciences, 2014, 111(33): 12264-12269.
Mccormick, et al., "Experimental Design, Preprocessing, Normalization and Differential Expression Analysis of Small RNA Sequencing Experiments", Silence, 2011, 2(2):19 pages.
Mcpherson, et al., "A Common Allele on Chromosome 9 Associated with Coronary Heart Disease", Science, Jun. 8, 2007, 316(5830):1488-1491.

(56) References Cited

OTHER PUBLICATIONS

Mestdagh, et al., "A Novel and Universal Method for MicroRNA RT-Qpcr Data Normalization", Genome Biology, 2009, 10(R64):10 pages.
Michalik, et al., "Long Noncoding RNA MALAT1 Regulates Endothelial Cell Function and Vessel Growth", Circulation Research, 2014, 114(9):1389-1397.
Milstein, Cesar, "The Hybridoma Revolution: An Offshoot of Basic Research", BioEssays, Nov. 1999, 21(11):966-973.
Mohammed, et al., "Coronary Microvascular Rarefaction and Myocardial Fibrosis in Heart Failure with Preserved Ejection Fraction", Circulation, Feb. 10, 2015, 131(6):550-559.
Molkentin, et al., "A Calcineurin-Dependent Transcriptional Pathway for Cardiac Hypertrophy", Cell, 1998, 93(2):215-228.
Murphy, et al., "Matrix Metalloproteinase Degradation of Elastin, Type IV Collagen and Proteoglycan. A Quantitative Comparison of the Activities of 95 Kda and 72 Kda Gelatinases, Stromelysins-1 And -2 and Punctuated Metalloproteinase", Biochemical Journal, 1991, 277(1):277-279.
Nishida, et al., "p38α Mitogen-Activated Protein Kinase Plays a Critical Role in Cardiomyocyte Survival but Not in Cardiac Hypertrophic Growth in Response to Pressure Overload", Molecular and Cellular Biology, 2004, 24(24):10611-10620.
Ounzain, et al., "Genome-Wide Profiling of the Cardiac Transcriptome after Myocardial Infarction Identifies Novel Heart-Specific Long Non-Coding RNAs", European Heart Journal, 2015, 36(6):353-368.
Owens, et al., "Identification of Two Short Internal Ribosome Entry Sites Selected from Libraries of Random Oligonucleotides", Proceedings of the National Academy of Sciences, Feb. 13, 2001, 98(4):1471-1476.
Ozawa, et al., "Histone Deacetylase 3 Associates with and Represses the Transcription Factor GATA-2", Blood, Oct. 2001, 98(7):2116-2123.
Poller, et al., "Non-coding RNAs in Cardiovascular Diseases: Diagnostic and Therapeutic Perspectives", European Heart Journal, 2018, 39(29): 2704-2716.
Re, Richard, "The Application of Antisense Technology to Medicine", Ochsner Journal, 2000, 2(4):233-236.
Rosario, et al., "Activation of the Ral and Phosphatidylinositol 3' Kinase Signaling Pathways by the Ras-Related Protein TC21", Molecular and Cellular Biology, Jun. 2001, 21(11):3750-3762.
Sano, et al., "p53-induced Inhibition of Hif-1 Causes Cardiac Dysfunction During Pressure Overload", Nature, Apr. 2007, 446(7134):444-448.
Scheuermann, et al., "Getting to the Heart of the Matter: Long Non-Coding Rnas in Cardiac Development and Disease", The EMBO Journal, 2013, 32(13):1805-1816.
Schonrock, et al., "Long Noncoding RNAs in Cardiac Development and Pathophysiology", Circulation Research, 2012, 111(10):1349-1362.
Tamhane, et al., "Multiple Test Procedures for Identifying the Minimum Effective and Maximum Safe Doses of a Drug", Journal of the American Statistical Association, Mar. 2002, 97(457):293-301.
Thum, Thomas, "Facts and Updates about Cardiovascular Non-Coding RNAs in Heart Failure", ESC Heart Failure, 2015, 2(3):108-111.
Thum, et al., "Long Noncoding RNAs and MicroRNAs in Cardiovascular Pathophysiology", Circulation Research, 2015, 116(4):751-762.
Thum, et al., "Microrna-21 Contributes to Myocardial Disease by Stimulating MAP Kinase Signaling in Fibroblasts", Nature, Dec. 25, 2008, 456(7224):980-984.
Tirziu, et al., "Myocardial Hypertrophy in the Absence of External Stimuli is Induced by Angiogenesis in Mice", Journal of Clinical Investigation, 2007, 117(11):3188-3197.
Tomlinson, Ian M., "Next-generation Protein Drugs", Nature Biotechnology, 2004, 22:521-522.
Topkara, et al., "Role of MicroRNAs in Cardiac Remodeling and Heart Failure", Cardiovascular Drugs and Therapy, 2011, 25(2):171-182.
Tsai, et al., "An Early Hematopoietic Defect in Mice Lacking the Transcription Factor GATA-2", Nature, 1994, 371 (6494):221-226.
Tsai, et al., "Long Noncoding RNA as Modular Scaffold of Histone Modification Complexes", Science, Aug. 2010, 329(5992):689-693.
Ucar, et al., "The miRNA-212/132 Family Regulates both Cardiac Hypertrophy and Cardiomyocyte Autophagy", Nature Communications, Sep. 25, 2012, 3(1078):11 pages.
Uchida, et al., "Long Noncoding RNAs in Cardiovascular Diseases", Circulation Research, 2015, 116(4)737-750.
Vermeulen, et al., "RNA Pre-Amplification Enables Large-Scale RT-qPCR Gene-Expression Studies on Limiting Sample Amounts", BMC Research Notes, 2009, 2(235):9 pages.
Viereck, et al., "Long Noncoding RNA Chast Promotes Cardiac Remodeling", Science Translational Medicine, Feb. 17, 2016, 8(326):13 pages.
Viereck, et al., "Regulatory RNAs and Paracrine Networks in the Heart", Cardiovascular Research, 2014, 102(2):290-301.
Wang, et al., "Ephrin-B2 Controls VEGF-Induced Angiogenesis and Lymph angiogenesis", Nature, May 2010, 465(7297):483-486.
Wang, et al., "The Long Noncoding RNA CHRF Regulates Cardiac Hypertrophy by Targeting miR-489", Circulation Research, 2014, 114(9):1377-1388.
Yang, et al., "Deep RNA Sequencing Reveals Dynamic Regulation of Myocardial Noncoding RNAs in Failing Human Heart and Remodeling with Mechanical Circulatory Support", Circulation, 2014, 129(9):1009-1021.
Zaher, et al., "Selection of an Improved RNA Polymerase Ribozyme with Superior Extension and Fidelity", RNA, Aug. 2007, 13(7):1017-1026.
Zimmermann, et al., "RNAi-mediated Gene Silencing in Non-Human Primates", Nature, 2006, 441(7089):111-114.

Figure 2:
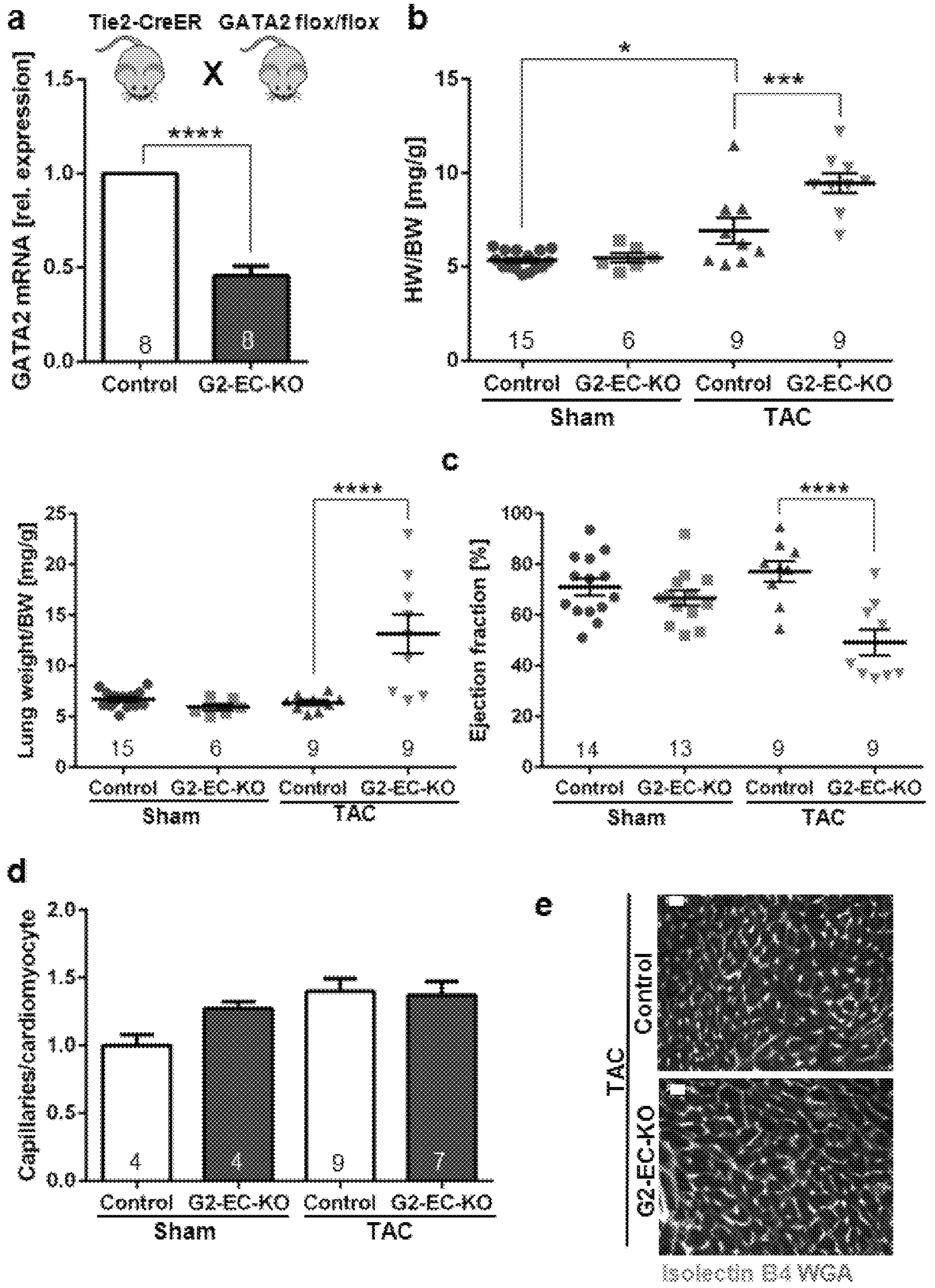

Figure 2 –continued
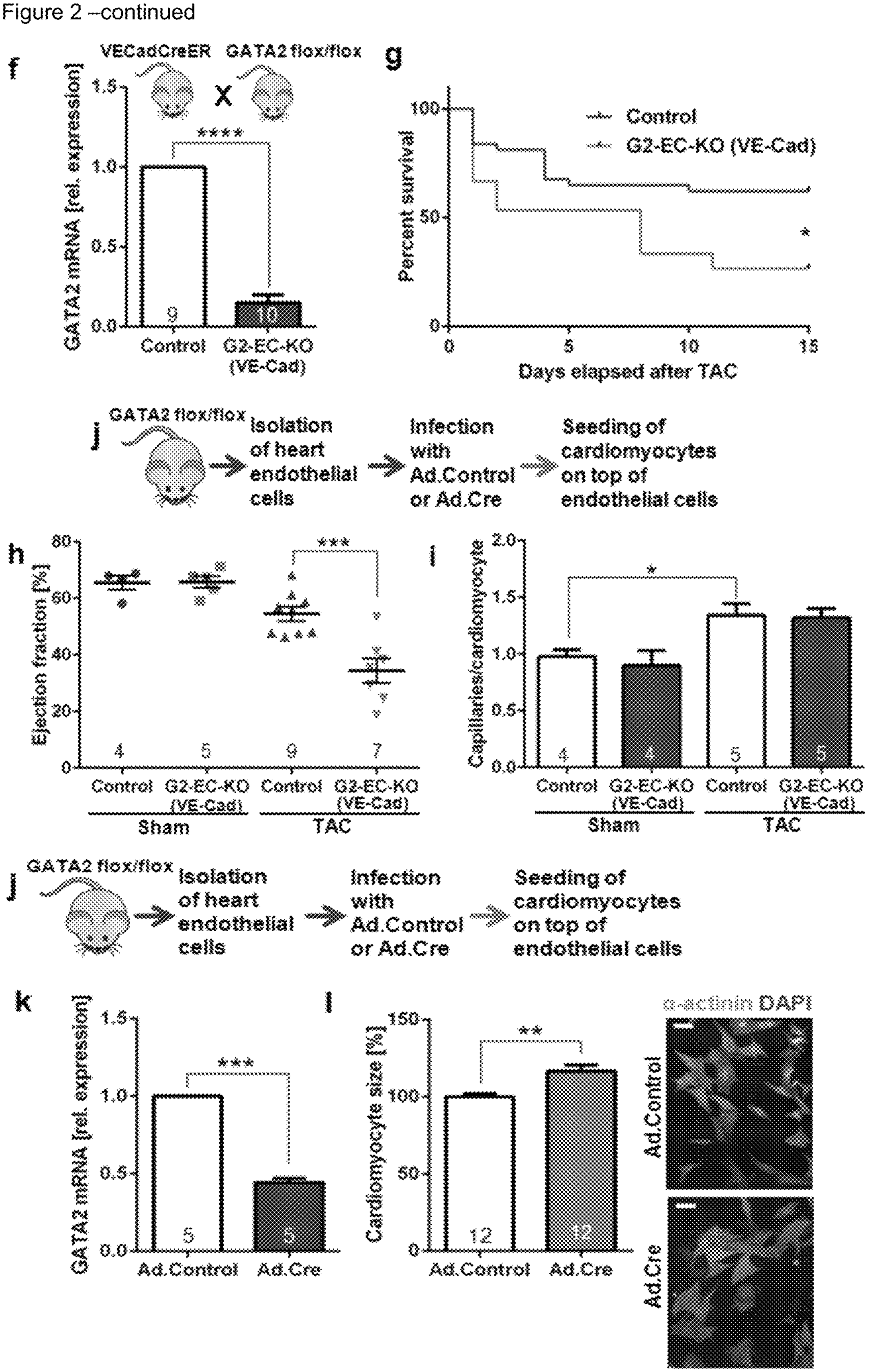

Figure 3:
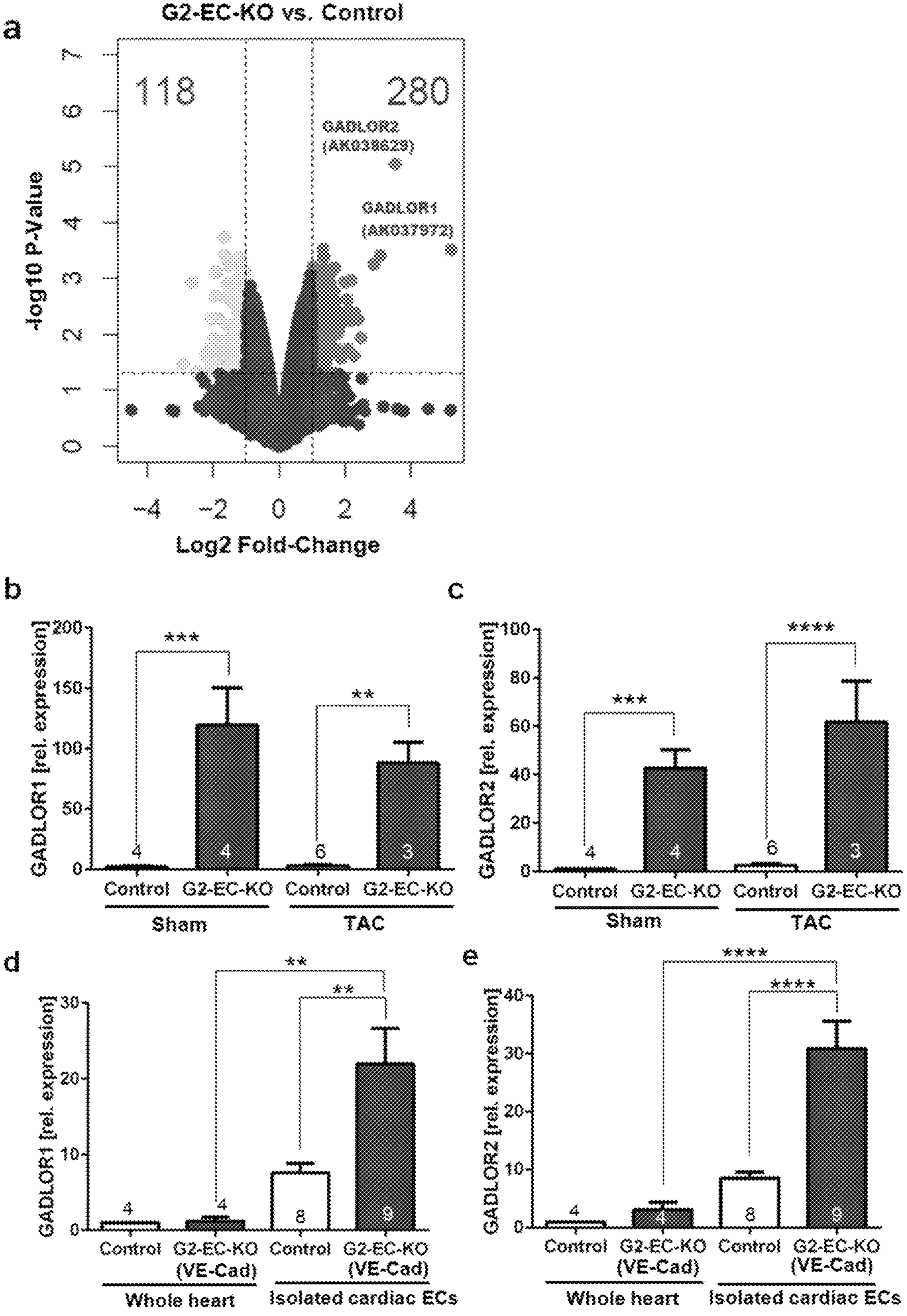

Figure 3 – continued
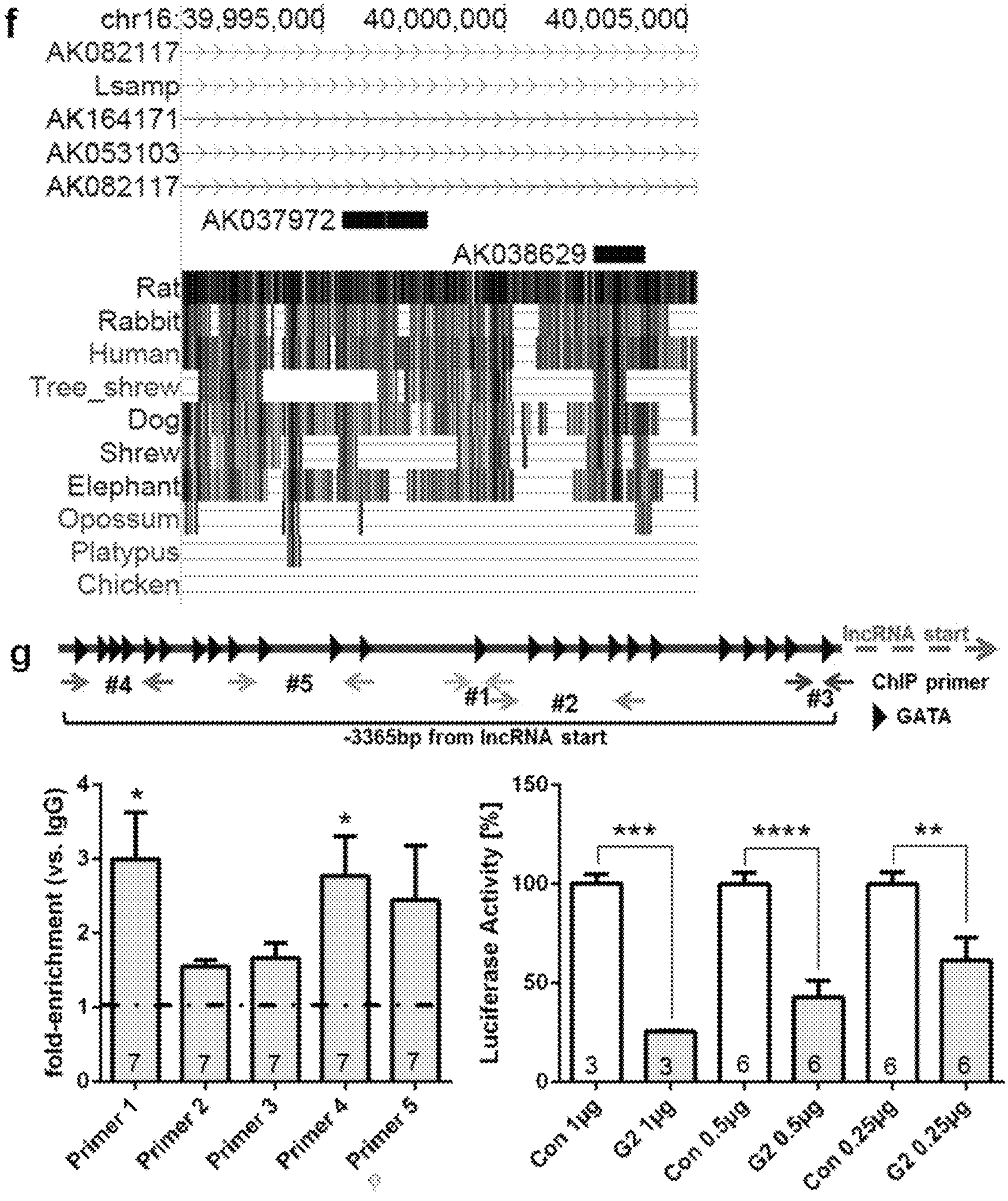

Figure 3 – continued
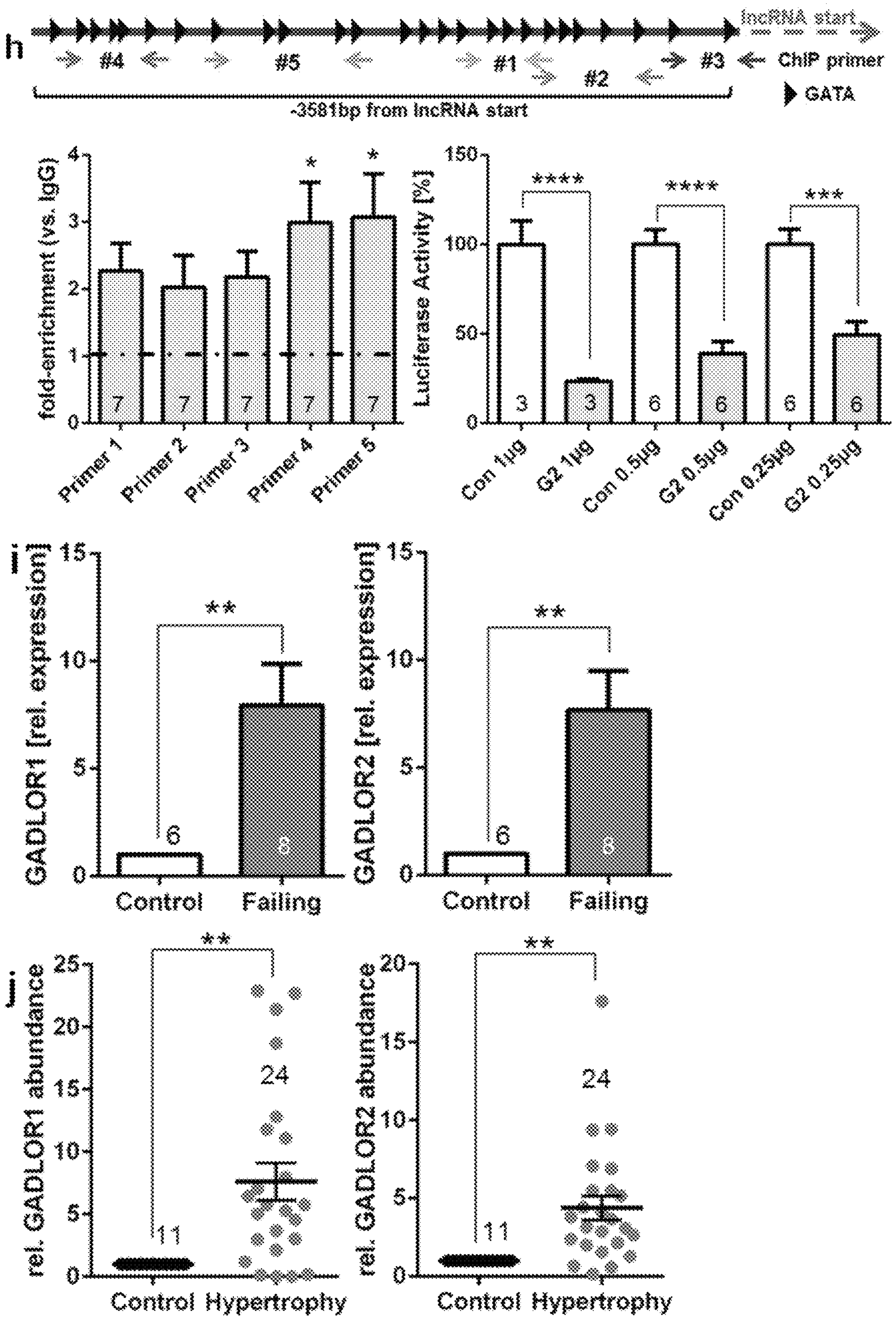

Figure 4:
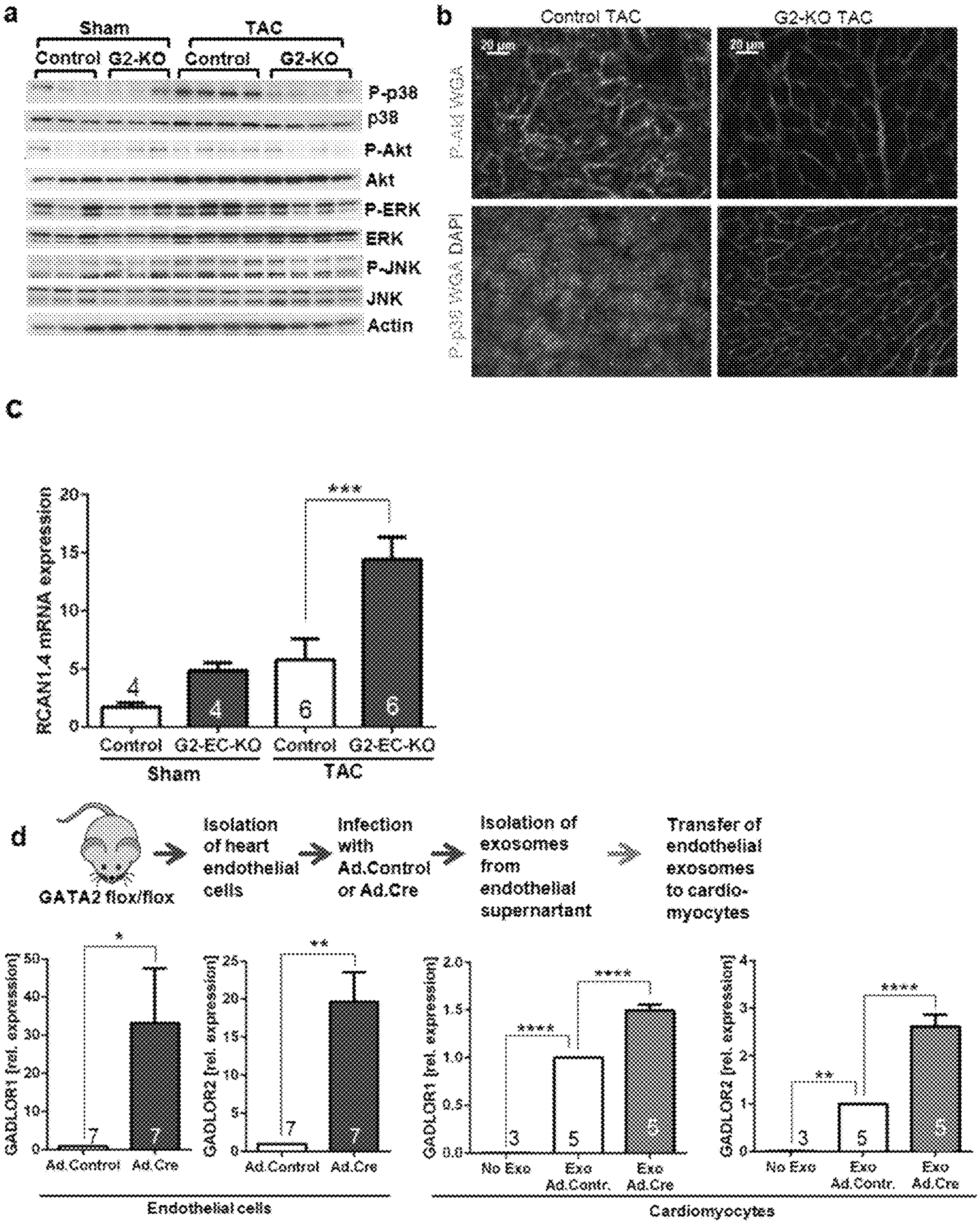

Figure 4 – continued
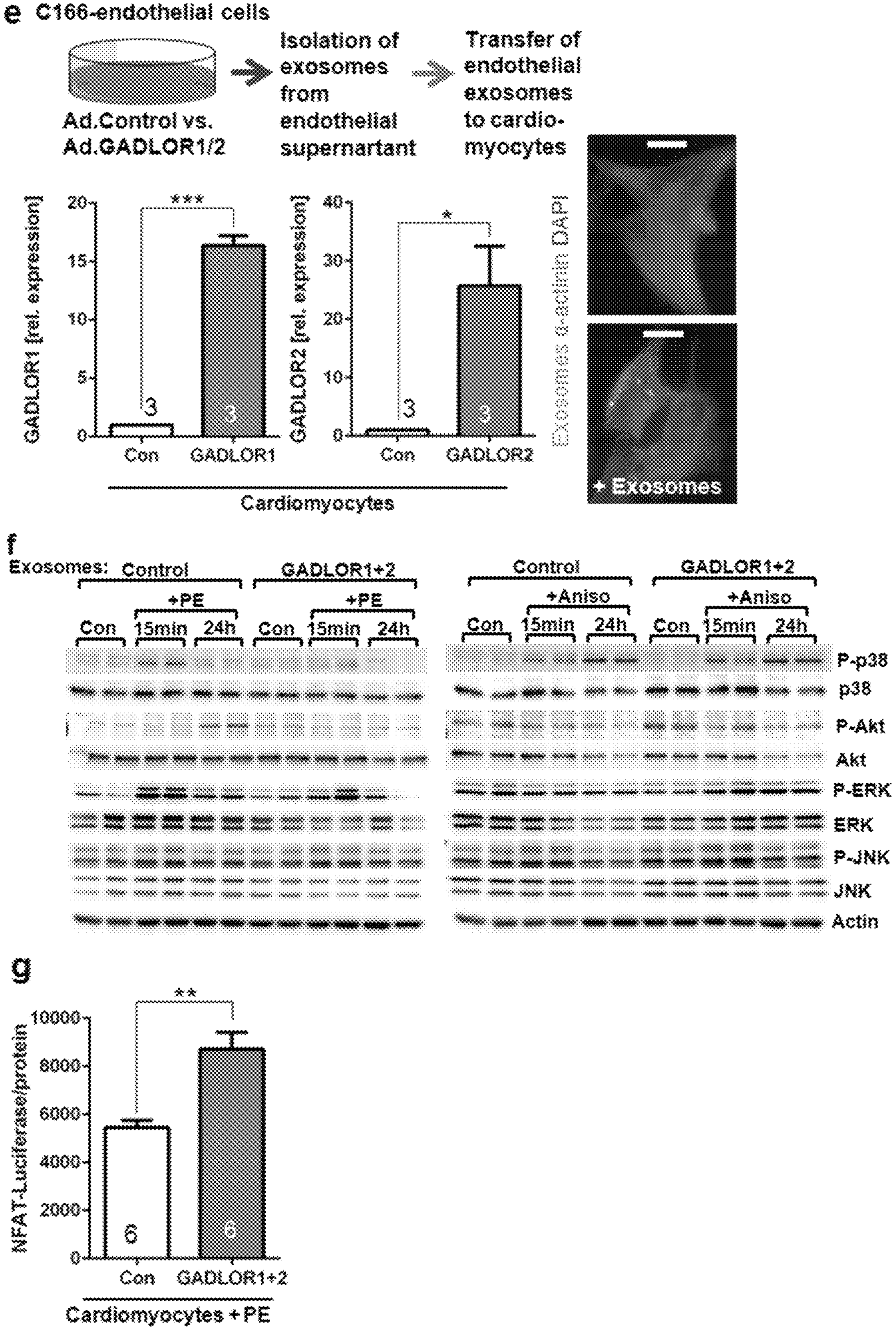

a b

| GADLOR2 bound proteins | Protein function |
|---|---|
| Polyubiquitin A, C<br>Ubiquitin 60S, 40S ribos. proteins<br>Obsl1 (E3 ligase adapter) | Ubiquitin-related |
| TC21(Rras2), Ral-A | Signaling |
| Ran, Argonaute-2, Nuclease sensitive element binding protein1, HnRNPA2/B1, Tial1, Dazap1, Ddx17 | RNA-binding, RNA metabolism |
| Rab11A, 11B, Rab2A, Sec22b, Myof | Vesicle formation<br>Exocytosis |
| Ankyrin3, Moesin, Krt16 | Structural |

Figure 5:
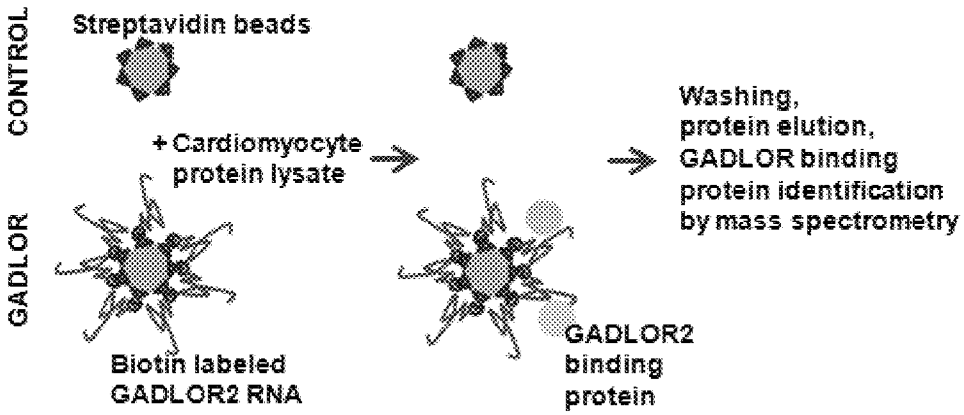

Figure 5 – continued
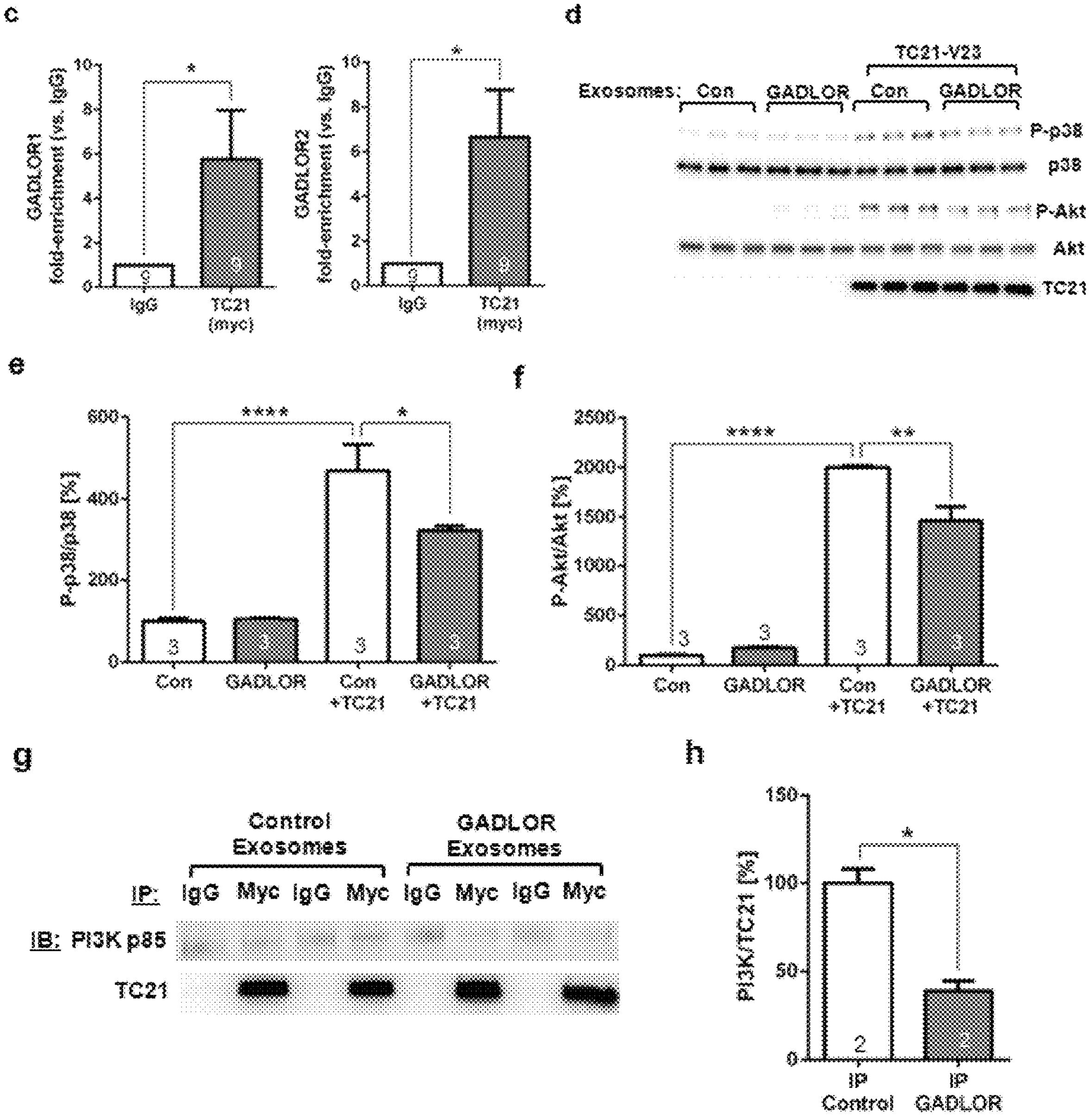

a b c

Figure 6:
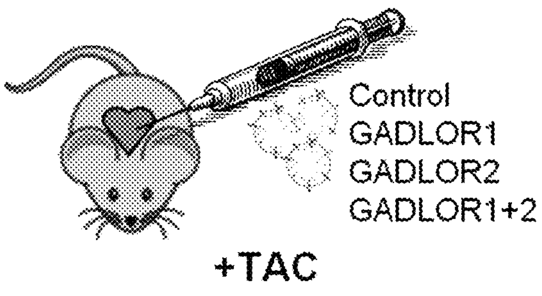
Figure 6:
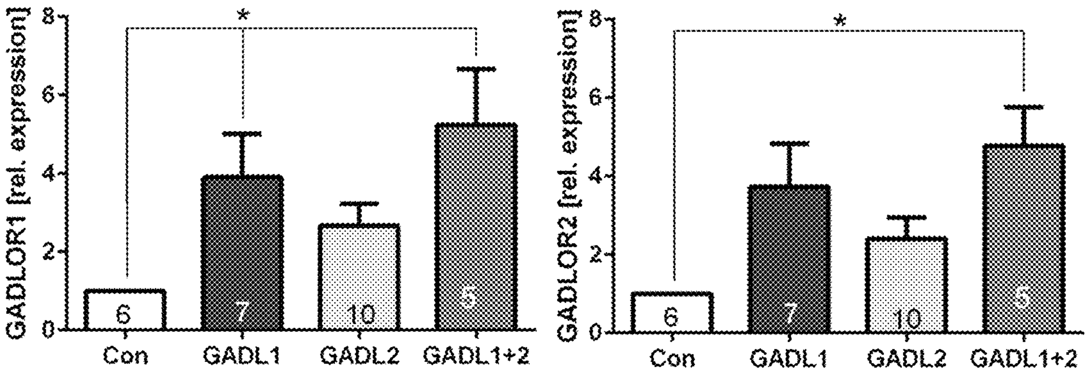
Figure 6:
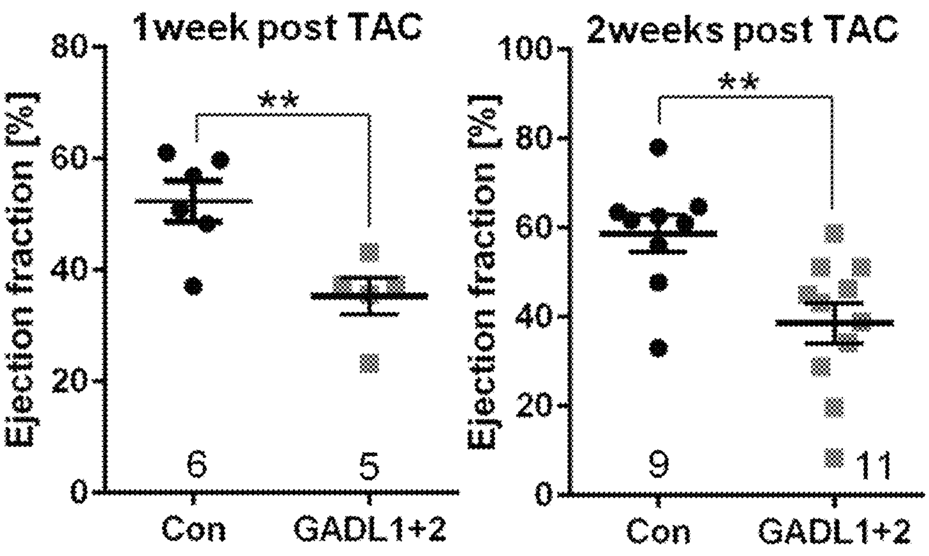

Figure 6 – continued
d
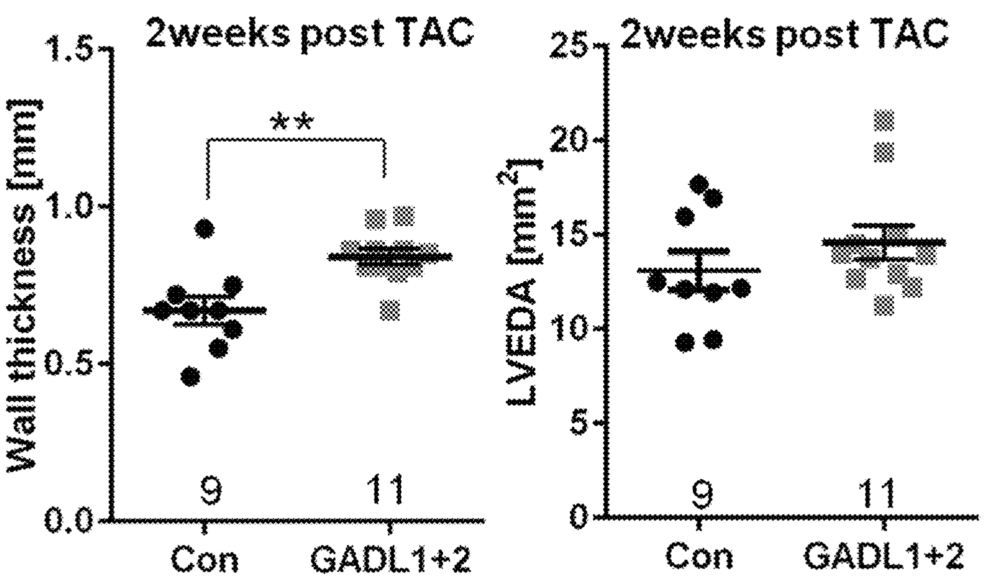
e
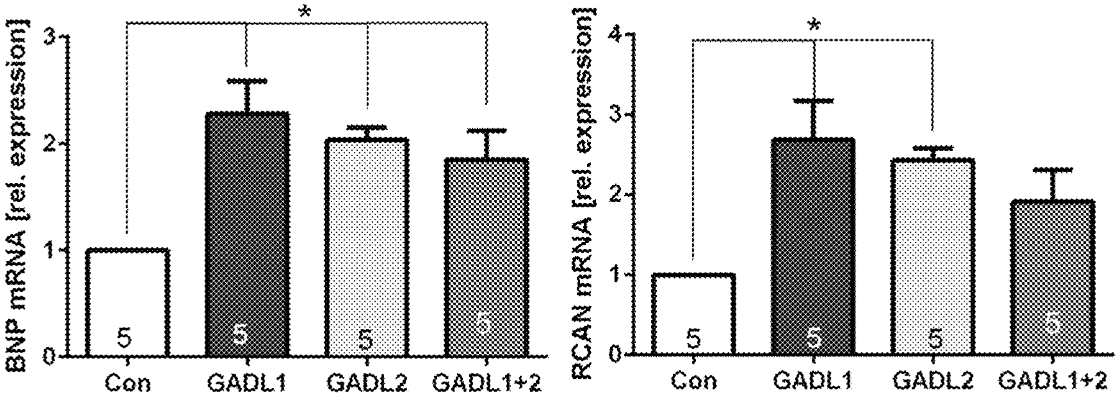
f
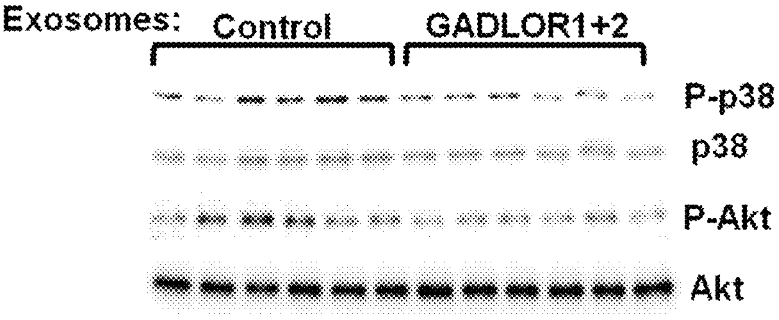

Figure 6 - continued
g
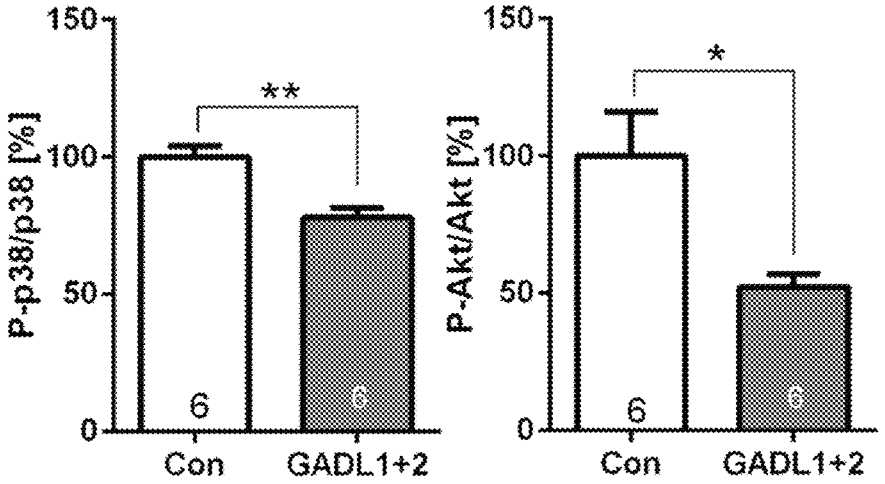
h
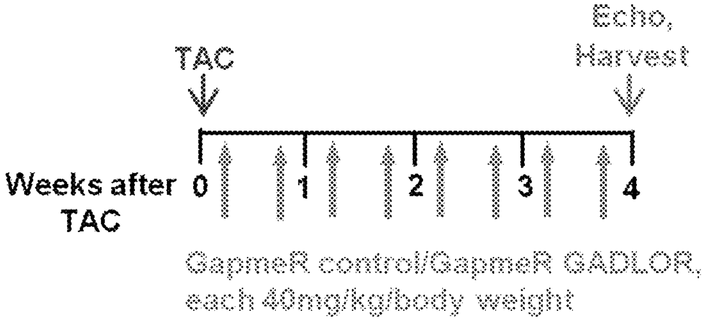
i
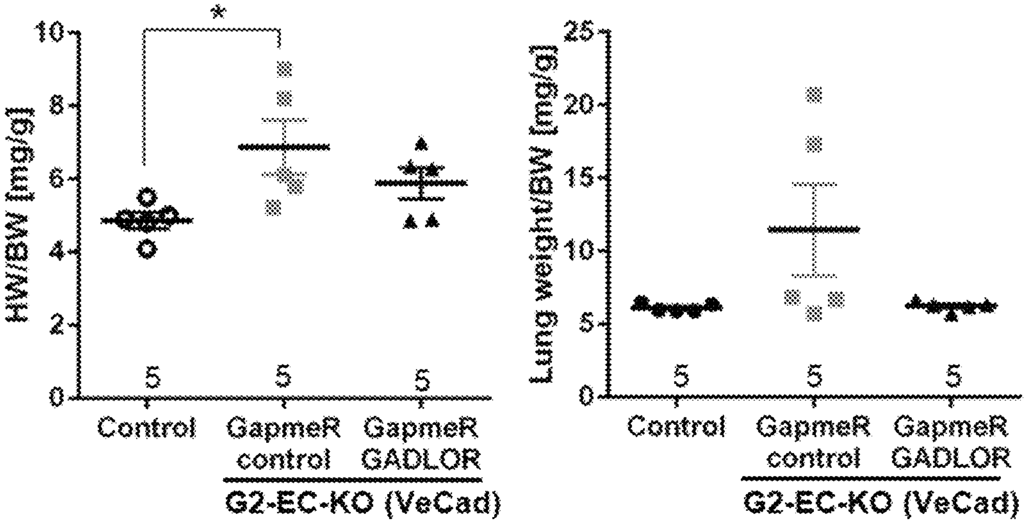

Figure 6 - continued
j
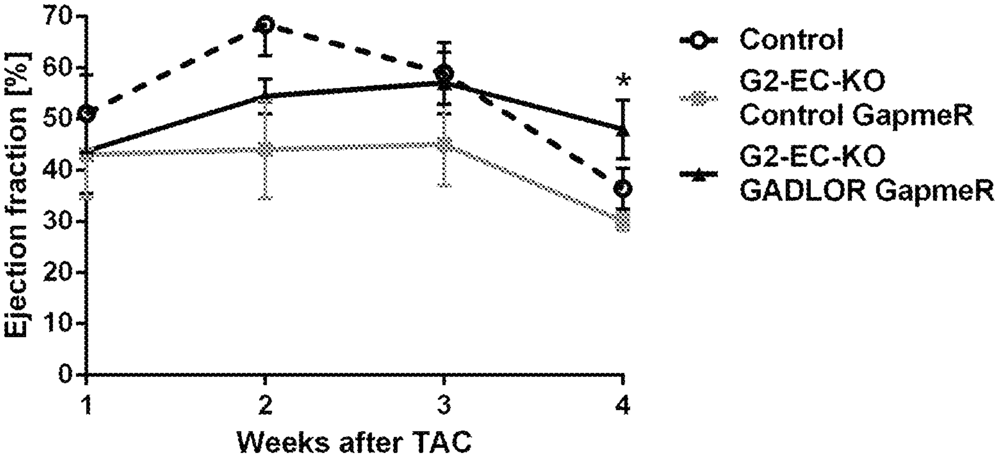
k
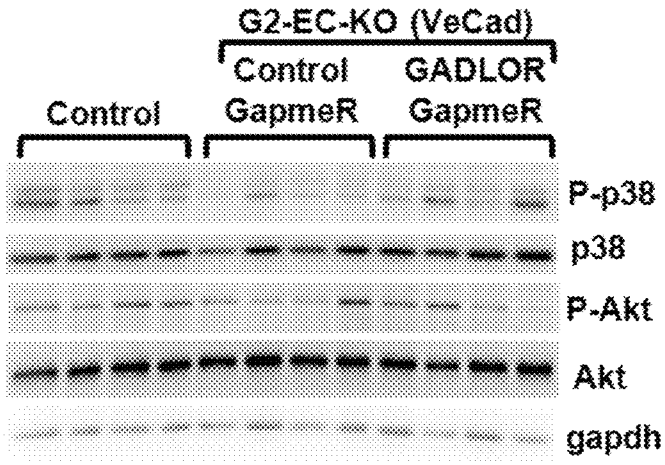
l
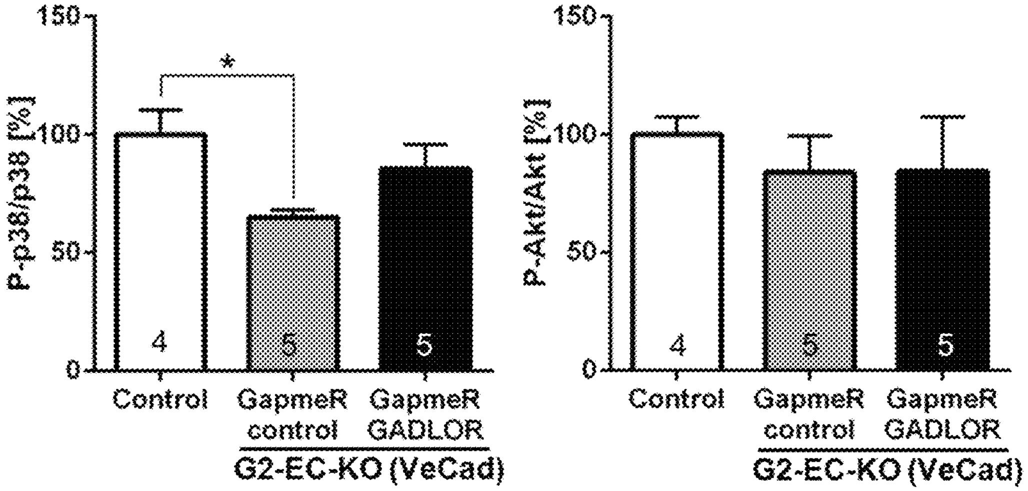

Figure 7:
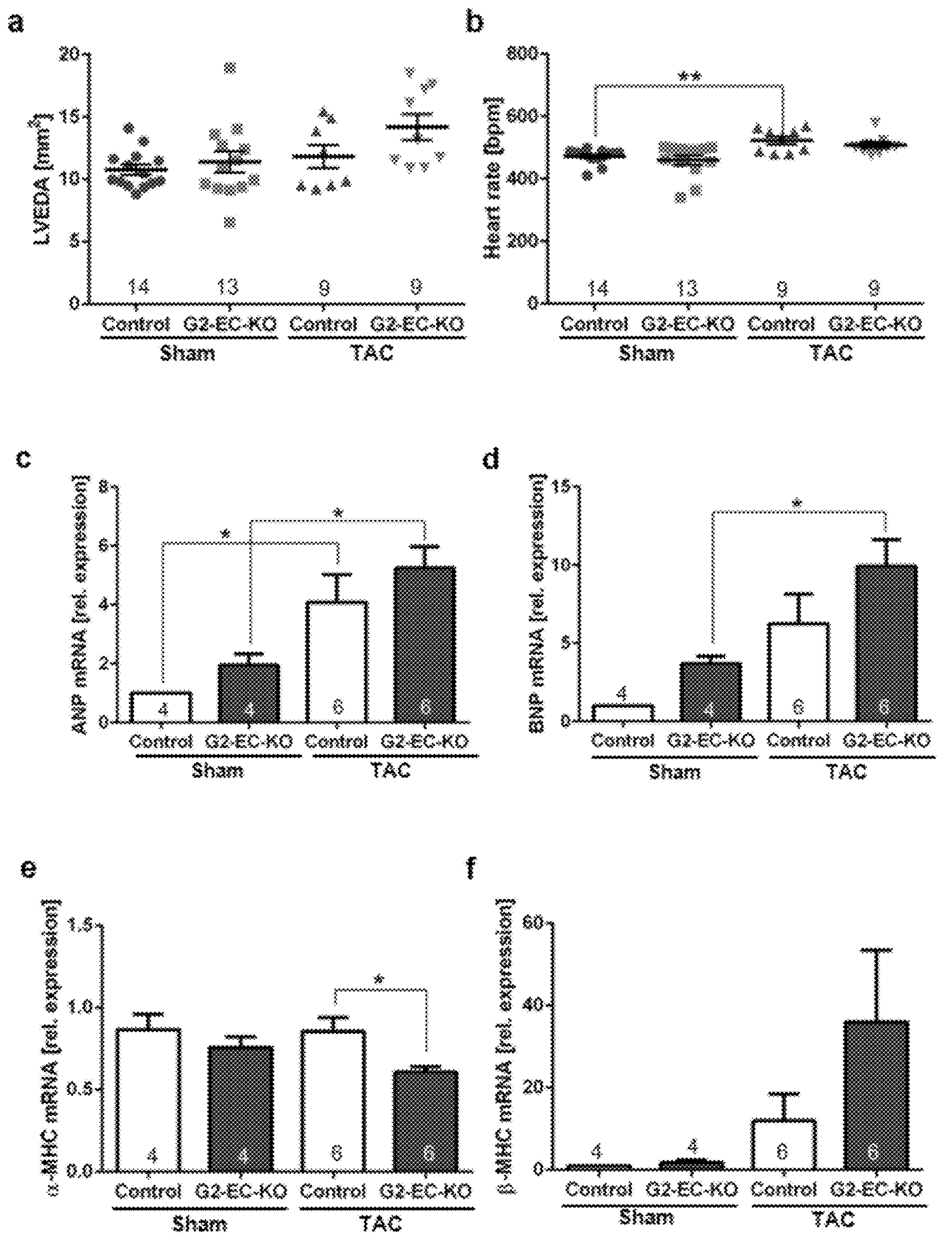

Figure 7 - continued
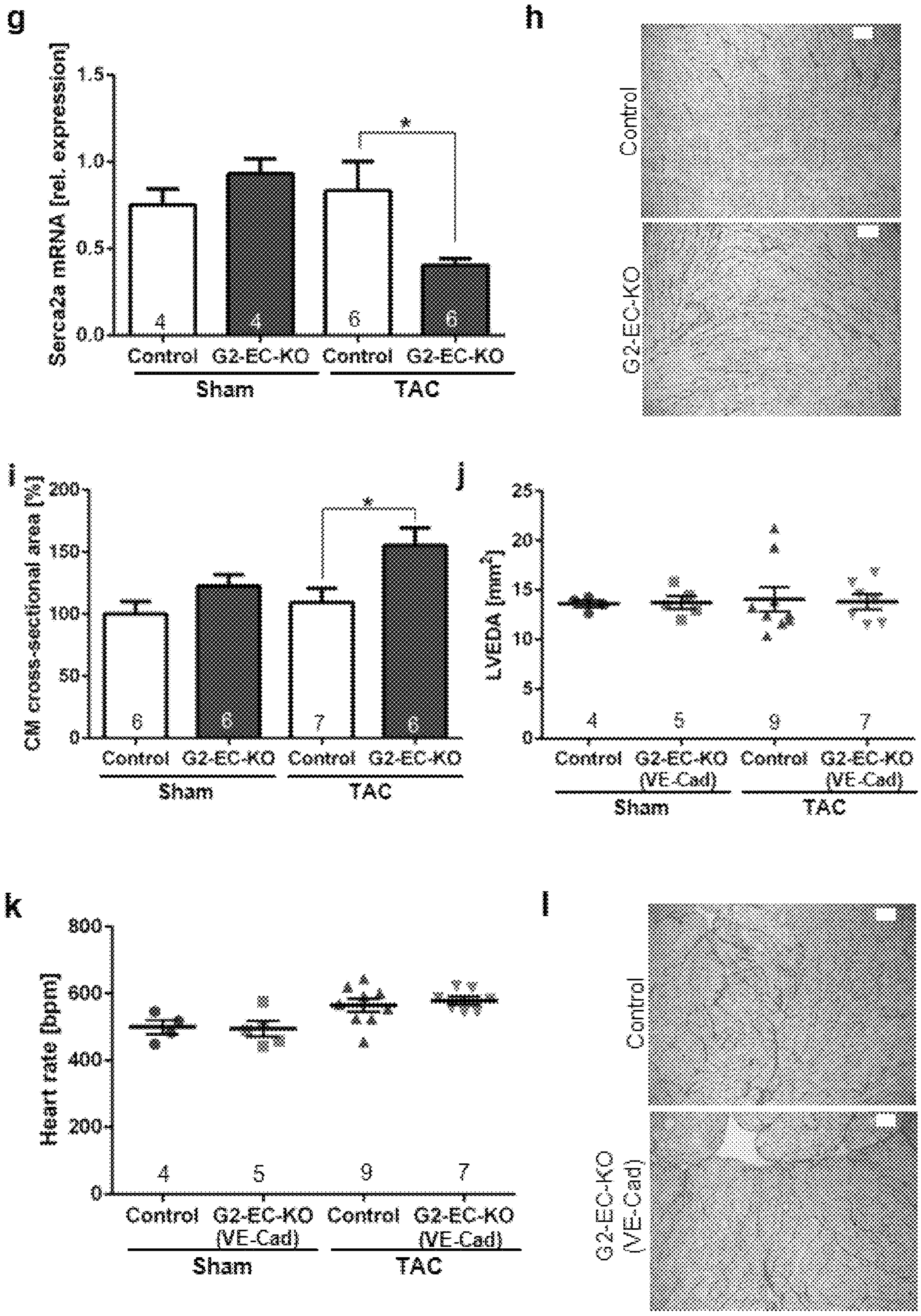

a

Figure 8:
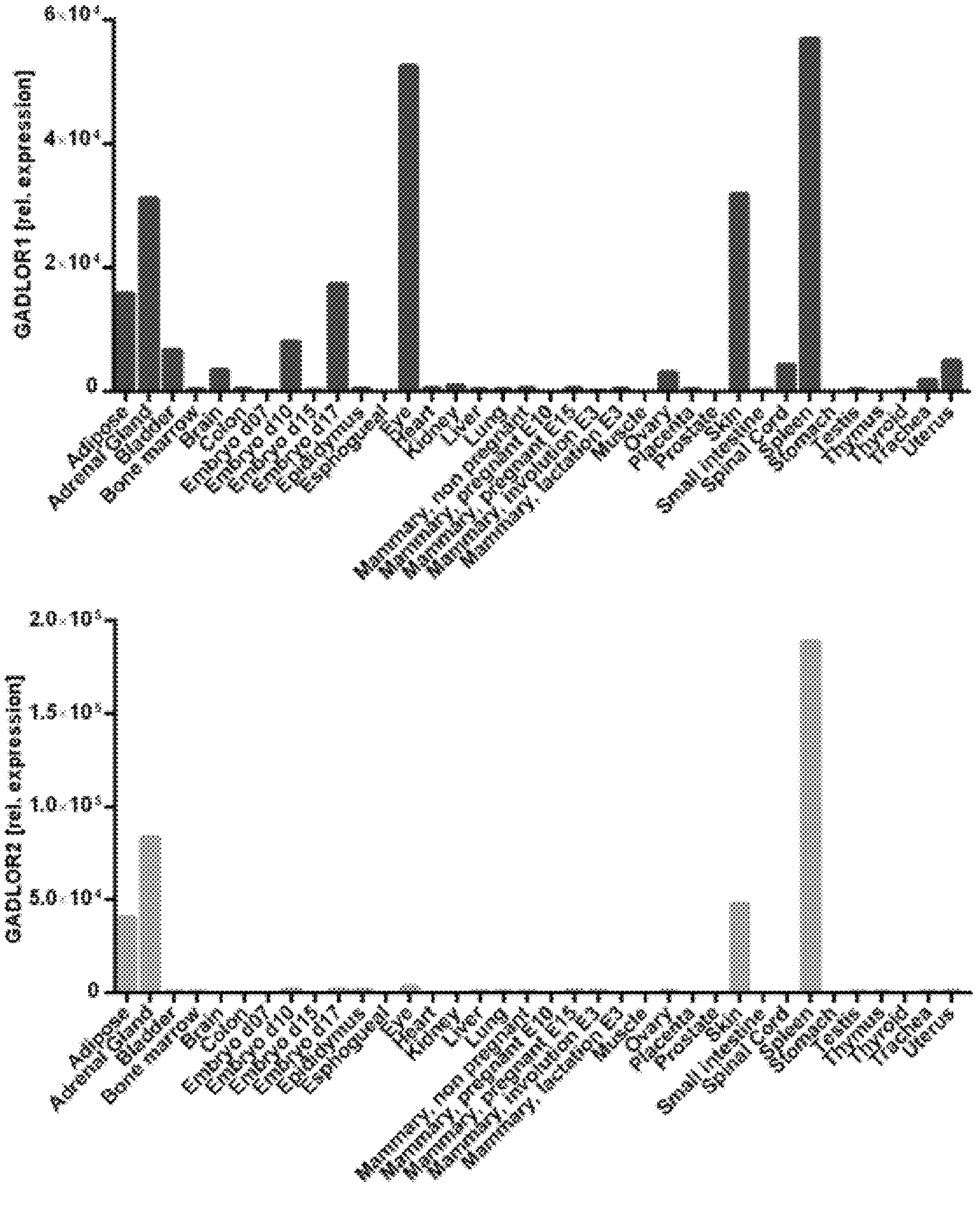

Figure 8 - continued
b
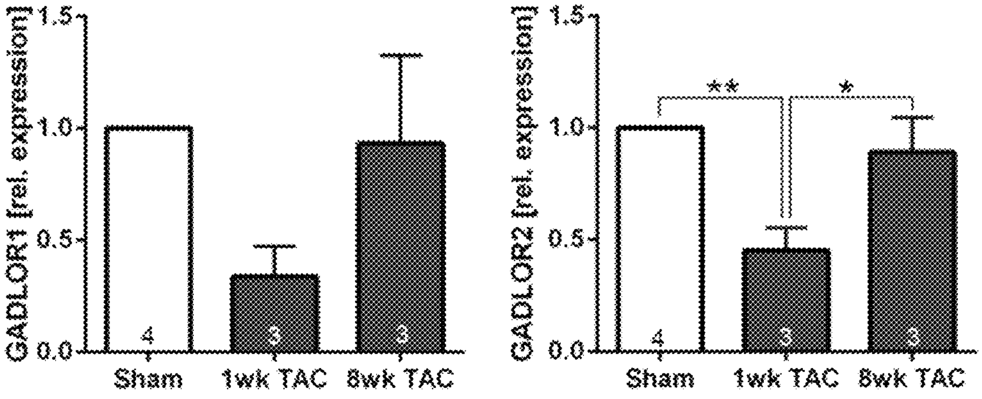
Figure 9
GADLOR1
| Label | Strand | Frame | Start | Stop | Length (bp \| aa) |
|---|---|---|---|---|---|
| ORF8 | + | 3 | 309 | 542 | 234 \| 77 |
| ORF1 | + | 1 | 196 | 423 | 228 \| 75 |
| ORF6 | + | 2 | 1355 | 1522 | 168 \| 55 |
| ORF4 | + | 2 | 302 | 436 | 135 \| 44 |
| ORF2 | + | 1 | 1087 | 1200 | 114 \| 37 |
| ORF7 | + | 2 | 2105 | 2218 | 114 \| 37 |
| ORF9 | - | 3 | 2198 | 2094 | 105 \| 34 |
| ORF5 | + | 2 | 446 | 529 | 84 \| 27 |
| ORF3 | + | 1 | 1519 | 1599 | 81 \| 26 |
GADLOR2
| Label | Strand | Frame | Start | Stop | Length (bp \| aa) |
|---|---|---|---|---|---|
| ORF6 | - | 3 | 794 | 627 | 168 \| 55 |
| ORF7 | - | 3 | 353 | 246 | 108 \| 35 |
| ORF4 | - | 2 | 867 | 769 | 99 \| 32 |
| ORF3 | - | 1 | 886 | 794 | 93 \| 30 |
| ORF2 | + | 3 | 1197 | 1283 | 87 \| 28 |
| ORF1 | + | 2 | 1136 | 1213 | 78 \| 25 |
| ORF5 | - | 2 | 753 | 676 | 78 \| 25 |

Figure 10:
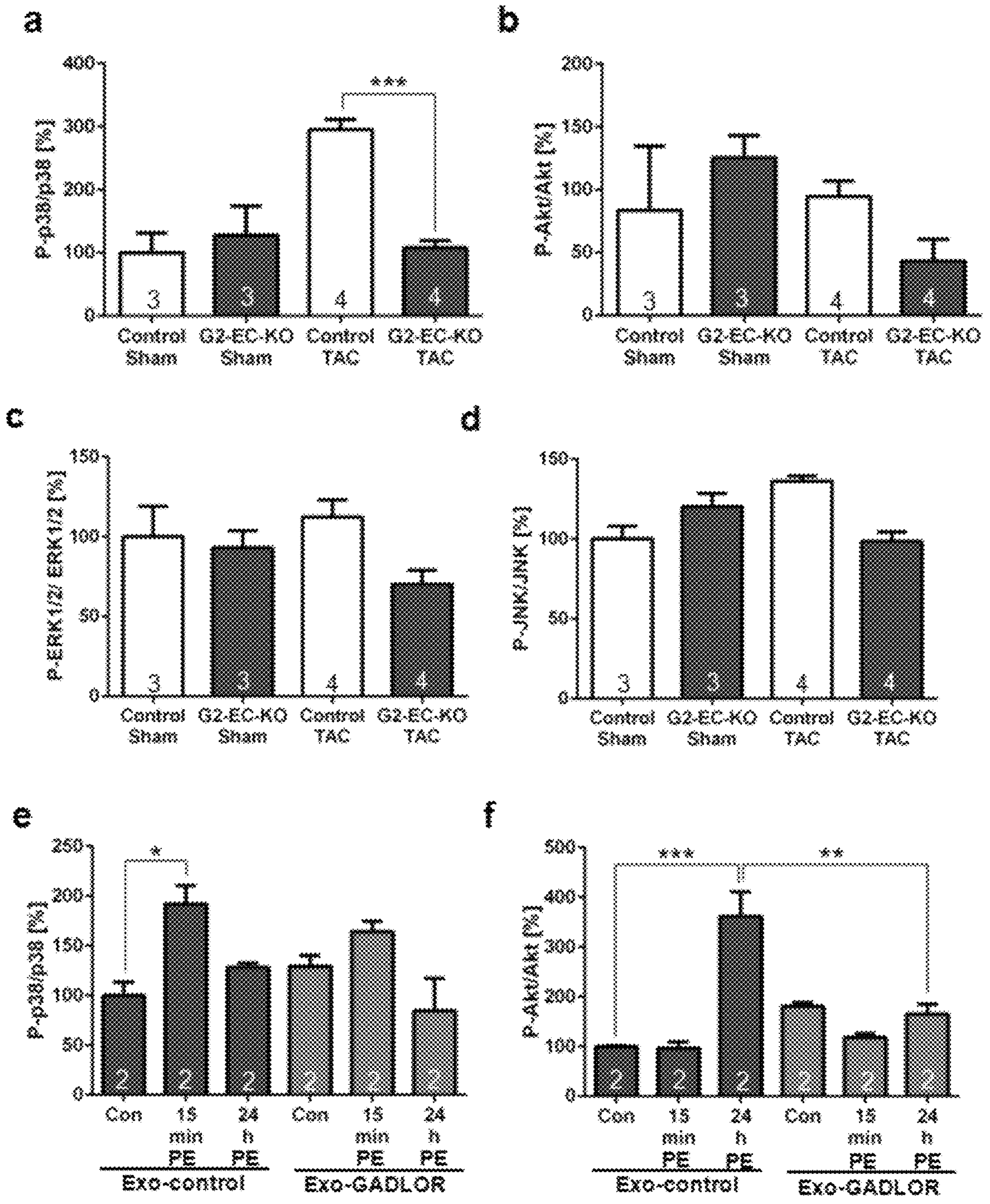

Figure 10 - continued
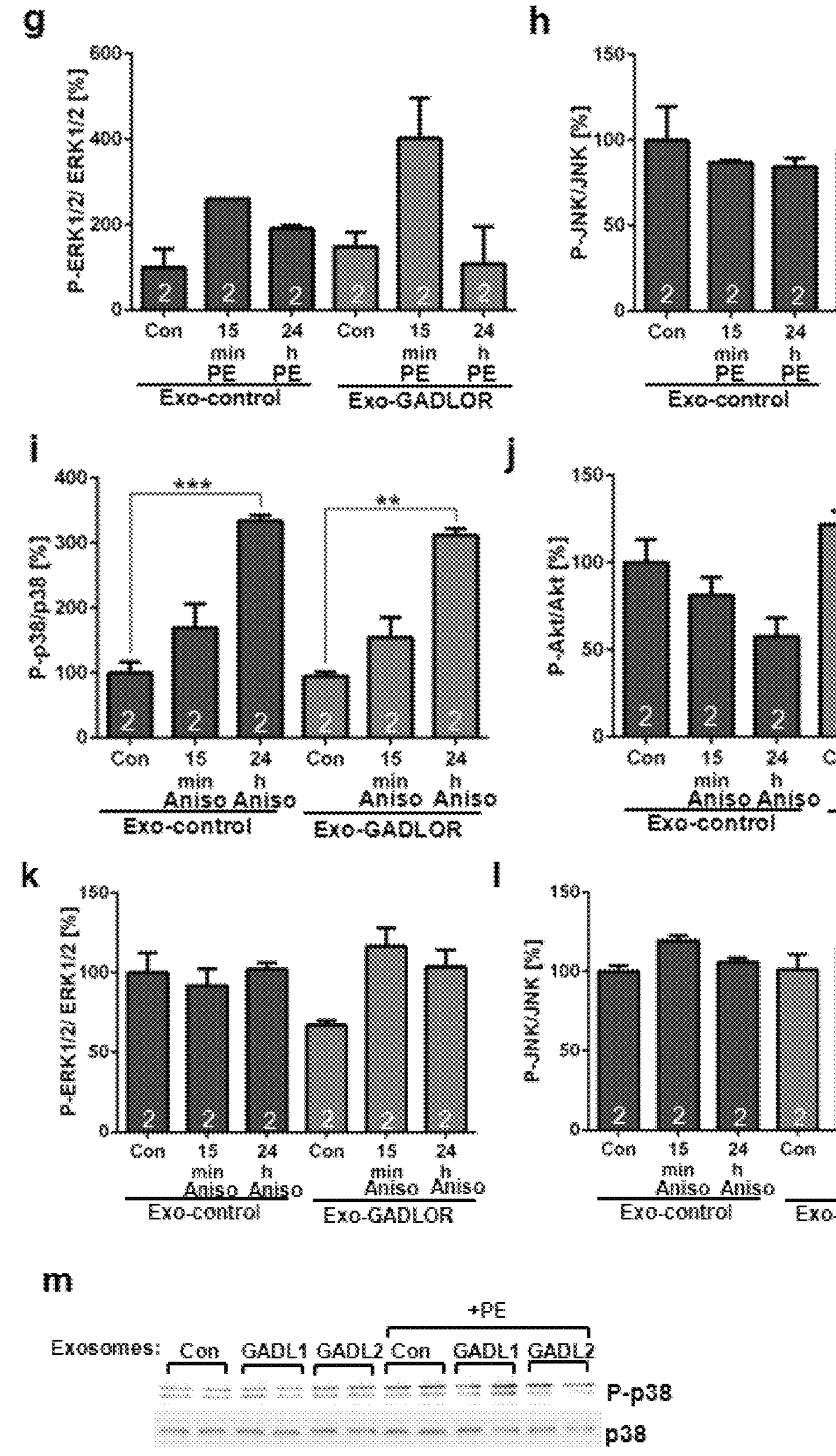

INCRNAS GADLOR 1 AND 2 FOR USE IN TREATING AND PREVENTING CARDIAC REMODELLING

RELATED PATENT APPLICATION

This patent application is a 35 U.S.C. 371 national phase patent application of PCT/EP2018/064226, filed on May 30, 2018, entitled "lncRNAs GADLOR 1 AND 2 FOR USE IN TREATING AND PREVENTING CARDIAC REMODELLING", naming Jorg Heineke and Natali FROESE as inventors, which claims priority to European Application No. 17173818.0 filed on May 31, 2017, entitled "lncRNAs GADLOR 1 AND 2 FOR USE IN TREATING AND PREVENTING CARDIAC REMODELLING," naming Jorg Heineke and Natali FROESE as inventors. The entire content of the foregoing patent applications is are incorporated herein by reference, including all text, tables and drawings.

SEQUENCE LISTING

The instant application contains a Sequence Listing which has been submitted electronically in ASCII format and is hereby incorporated by reference in its entirety. Said ASCII copy is named Sequenzprotokoll and is 26.365 bytes in size.

The present invention relates to a compound inhibiting the expression and/or the activity of a long non-coding RNA (lncRNA) selected from GADLOR 1 and GADLOR 2 for use in treating or preventing cardiac remodelling, wherein GADLOR 1 comprises or consists of a nucleic acid sequence selected from the group consisting of SEQ ID NOs 1 to 3 and sequences being at least 75% identical thereto, and GADLOR 2 comprises or consists of a nucleic acid sequence selected from the group consisting of SEQ ID NOs 4 to 6 and sequences being at least 75% identical thereto.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Large-scale analysis of mammalian transcriptomes uncovered that transcription of genomes leads to a complex proportion of RNA molecules of which only a small fraction serves as templates for protein synthesis. Several studies indicate that these non-coding RNAs (ncRNAs) have as important biological functions as their protein coding counterparts and suggest that altered expression or function of ncRNAs effects cardiovascular diseases, including cardiac diseases involving cardiac remodelling, such as cardiac hypertrophy and fibrosis, coronary artery disorders, as well as myocardial infarction.

The most reflected ncRNAs in cardiovascular research are microRNAs (miRNAs, miRs). These are endogenous, single-stranded RNAs composed of approximately 20-22 nucleotides that bind other transcripts reducing the stability and/or translation of their targets. For example, it was shown that miR-21 and miR-132 induce cardiac fibrosis or hypertrophy, respectively, and that in vivo repression of these miRNAs by specific AntagomiRs (being chemically engineered oligonucleotides silencing miRNAs) rescues fibrosis or hypertrophy in cardiac disease model of pressure-overload (Thum et al. Nature. 2008 456(7224):980-4.; Ucar and Gupta et al. Nat Commun. 2012 3:1078). In another study it was found that miR-24 acts as a critical regulator of angiogenesis in ischemic heart disease (Fiedler et al. Circulation. 2011 124(6):720-30). Topkara and Mann (2011), Cardiovasc Drugs Ther.; 25(2):171-82 provides a review on the role of miRNAs in cardiac remodelling and heart failure.

More recent studies indicate that similar to miRNAs, long ncRNAs (lncRNAs) may also play an important role in various biological processes. LncRNAs are mRNA-like transcripts ranging from 200 nucleotides up to 100 kilobases and are classified based on their genomic distribution relative to protein-coding genes (sense to exons and/or introns, antisense, bidirectional, or intergenic). Several lncRNA transcripts are exclusively restricted to the nucleus, while others are also found in the cytoplasm. Here they interact with proteins as well as other RNA or DNA molecules enabling lncRNAs to influence a variety of gene regulatory mechanisms including chromatin modification, genomic imprinting, nuclear compartmentalization and architecture, as well as transcriptional and post-transcriptional regulation (Schonrock et al. Circ Res. 2012 Oct. 26; 111(10):1349-62.; Caley et al. ScientificWorldJournal. 2010 10:90-102). Not surprisingly, lncRNAs are involved in human disease, such as cancer, metabolic and neuronal disorders.

However, little is known about their role in cardiovascular biology and in particular in cardiac disease. Chronic heart failure is a common and deadly disease. It mainly develops after myocardial infarction or due to arterial hypertension or abnormalities of the cardiac valves[1,2]. In the course of these diseases, an increased workload is imposed on the left ventricular chamber of the heart. As consequence, the myocardium mounts a hypertrophic response with growth of cardiomyocytes in order to maintain cardiac output. Although initially compensatory, this pathological hypertrophy often leads to the development of heart failure in the long term[1,2]. Beside cardiomyocyte growth, there are profound changes in the myocardial capillary network during disease progression: In the initial compensatory phase angiogenesis and capillary density are increased[3,4], but in endstage heart failure, capillary rarefaction emerges in the myocardium of mice and patients[5]. In addition to their crucial role for blood supply, capillary endothelial cells (ECs) communicate with cardiomyocytes and regulate growth and function of these cells independent of perfusion[3,4,6,7]. ECs relay specific paracrine signals for example via protein growth factors[8,9], but they also shed small vesicles like exosomes and thereby transfer micro-RNAs to cardiomyocytes[10].

Recent studies indicated that the two lncRNAs Braveheart (Bvht) and FOXF1 adjacent non-coding developmental regulatory RNA (Fendrr) are required for the differentiation of cardiomyocytes and the development of lateral mesoderm tissue in the heart and body wall, respectively (Klattenhoff et al. Cell. 2013 152(3):570-83.; Grote et al. Dev Cell. 2013 24(2):206-14). Both lncRNAs modulate the epigenetic profile of cells via an interaction with chromatin modifying complexes. Recent reports have also started to explore the role of lncRNAs in cardiovascular disease. Genome-wide association study (GWAS) identified single-nucleotide polymorphisms (SNPs) in loci encoding for the lncRNAs MIAT (myocardial infarction-associated transcript) or ANRIL (antisense noncoding RNA in the INK4 locus) that seem to be related to risk of myocardial infarction or coronary artery disease (Ishii et al. J Hum Genet. 2006 51(12):1087-99.; McPherson et al. Science. 2007 316(5830):1488-91). The lncRNA Kcnq1ot1 controls the expression of its antisense gene Kcnq1 that encodes for a potassium channel. Since the potassium channel activity is essential for a normal cardiac performance, an altered regulation related by lncRNAs might lead to an abnormal heart function (Korostowski et al. PLoS Genet. 2012 8(9):e1002956). The circulating lncRNA LIPCAR can be used to predict survival in patients with heart failure (Kumarswamy et al. (2014), Circ Res.; 114 (10):1569-75). Moreover, the lncRNA Chast has been shown to promote cardiac remodelling (Viereck et al. (2016), Sci Transl Med.; 8(326):326ra22).

One of the main challenges in cardiac disease research is to identify novel and effective approaches to modulate gene networks or specific intracellular signaling pathways that may prove as effective therapeutic options themselves or have the potential to expand the efficiency of existing therapeutic strategies. The object of the present invention is therefore the provision of novel means and methods for treating or preventing cardiac diseases, in particular cardiac remodelling. It was surprisingly found in connection with the present invention that the lncRNAs GADLOR 1 and 2 play a role in the development of cardiac remodelling thereby providing novel therapeutic and diagnostic strategies.

Hence, the present invention relates in a first aspect to a compound inhibiting the expression and/or the activity of a long non-coding RNA (lncRNA) selected from GADLOR 1 and GADLOR 2 for use in treating or preventing cardiac remodelling, wherein GADLOR 1 comprises or consists of a nucleic acid sequence selected from the group consisting of SEQ ID NOs 1 to 3 and sequences being at least 75% identical thereto, and GADLOR 2 comprises or consists of a nucleic acid sequence selected from the group consisting of SEQ ID NOs 4 to 6 and sequences being at least 75% identical thereto.

The present invention also encompasses a method for treating or preventing cardiac remodelling in a patient in need thereof by administering to the patient a therapeutically effective amount of a compound inhibiting the expression and/or the activity of a long non-coding RNA (lncRNA) selected from GADLOR 1 and GADLOR 2, wherein GADLOR 1 comprises or consists of a nucleic acid sequence selected from the group consisting of SEQ ID NOs 1 to 3 and sequences being at least 75% identical thereto, and GADLOR 2 comprises or consists of a nucleic acid sequence selected from the group consisting of SEQ ID NOs 4 to 6 and sequences being at least 75% identical thereto.

As used herein "GADLOR 1" and "GADLOR 2" (GATA Downregulated Long non-coding RNA 1 and 2) designate two lncRNAs that were found to be expressed in cardiac endothelial cells of mice. The mouse GADLOR 1 and GADLOR 2 genes are both found on chromosome 16 in close proximity to each other. Only 3601 bp separate these genes. An orthologous genomic region can be found on human chromosome 3. GADLOR 1 and GADLOR 2 are conserved in mammals (see FIG. 3*f*). The lncRNA GADLOR 1 sequences of human, mouse, and rat are shown in SEQ ID NO: 1, 2 and 3, respectively. Among the GADLOR 1 sequences the human GADLOR 1 sequence is most preferred. The human GADLOR 1 sequence of SEQ ID NO: 1 shares 57.3% identity with the mouse GADLOR 1 sequence of SEQ ID NO: 2 (in a 2628 nucleotides overlap), and shares 57.5% identity with the rat GADLOR 1 sequence of SEQ ID NO: 3 (in a 2694 nucleotides overlap). The mouse and rat GADLOR 1 sequences share 77.3% identity (in a 2447 nucleotides overlap). The lncRNA GADLOR 2 sequences of human, mouse, and rat are shown in SEQ ID NO: 4, 5 and 6, respectively. Among the GADLOR 2 sequences the human GADLOR 2 sequence is most preferred. The human GADLOR 2 sequence of SEQ ID NO: 4 shares 75.1% identity with the mouse GADLOR 2 sequence of SEQ ID NO: 5 (in a 619 nucleotides overlap), and shares 75.4% identity with the rat GADLOR 2 sequence of SEQ ID NO: 6 (in a 621 nucleotides overlap). The mouse and rat GADLOR 2 sequences share 87.0% identity (in a 1378 nucleotides overlap).

It is of further note with respect to the sequence conversation of GADLOR 1 among mammals that the mouse GADLOR 1 sequence is reversely expressed as compared to the human and rat GADLOR 1 sequences. Hence, when aligning the mouse GADLOR 1 sequence with the human or rat GADLOR 1 sequence the above-discussed sequence identities are found when the mouse sequence has a 3' to 5' orientation whereas the human or rat sequence has a 5' to 3' orientation (or vice versa). The same reverse orientation can be found for the GADLOR 2 sequences of human, mouse and rat.

The sequence identity of at least 75% with respect to any one of SEQ ID NOs 1 to 3 is with increasing preference at least 80%, at least 85%, at least 90%, at least 95%, at least 96%, at least 97%, at least 98%, at least 99% and at least 99.5%. The sequence identity is selected separately for each of the GADLOR 1 sequences of SEQ ID NOs 1 to 3. Also the sequence identity of at least 75% with respect to any one of SEQ ID NOs 4 to 6 is with increasing preference at least 80%, at least 85%, at least 90%, at least 95%, at least 96%, at least 97%, at least 98%, at least 99% and at least 99.5%. Again, the sequence identity is selected separately for each of the GADLOR 2 sequences of SEQ ID NOs 4 to 6. Preferred examples of nucleic acid sequences being at least 75% identical to one or more sequences of SEQ ID NOs 1 to 6 are nucleic acid sequences differing with increasing preference by no more than 10, such as 5, 4, 3, 2 or 1 nucleotide(s) from any one of SEQ ID NOs 1 to 6. The nucleotide differences may be the addition, deletion and/or substitution of nucleotide(s).

The term "ncRNA" or "non-coding RNA" as used herein designates a functional RNA molecule that is not translated into a protein. The DNA sequence from which a non-coding RNA is transcribed is often called in the art an RNA gene. The term "lncRNA" or "long non-coding RNA" is commonly used in the art and designates an ncRNA comprising more than 200 nucleotides. All species orthologs of GADLOR 1 and GADLOR 2 have more than 200 nucleotides. GADLOR 1 and GADLOR 2 are therefore lncRNAs.

A compound inhibiting the expression of GADLOR 1 and/or GADLOR 2 is in accordance with the present invention a compound lowering or preventing the transcription of the gene encoding GADLOR 1 and/or GADLOR 2. Such compounds include compounds interfering with the transcriptional machinery and/or its interaction with the promoter of said gene and/or with expression control elements remote from the promoter such as enhancers. The compound inhibiting the expression of GADLOR 1 and/or GADLOR 2 specifically inhibits the expression of said lncRNA(s), for example, by specifically interfering with the promoter region controlling the expression of one or both of these lncRNAs. Preferably, the transcription of GADLOR 1 and/or GADLOR 2 is reduced by at least 50%, more preferred at least 75% such as at least 90% or 95%, even more preferred at least 98% and most preferred by about 100% (e.g., as compared to the same experimental set up in the absence of the compound).

A compound inhibiting the activity of GADLOR 1 and/or GADLOR 2 in accordance with the present invention causes said lncRNA(s) to perform its/their function with lowered efficiency. The compound inhibiting the activity of GAD- LOR 1 and/or GADLOR 2 specifically inhibits the activity of said lncRNA(s). Preferably, the activity of GADLOR 1 and/or GADLOR 2 is reduced by at least 50%, more preferred at least 75% such as at least 90% or 95%, even more preferred at least 98%, and most preferably about 100% (e.g., as compared to the same experimental set up in the absence of the compound). The activity of GADLOR 1 and/or GADLOR 2 is preferably its/their capability to induce cardiac remodelling. Means and methods for determining the reduction of activity of a RNA are established in the art and are described, for example, in Esau et al. (2004), JBC, 279:52361-52365 or Gribbings et al. (2009), Nature Cell Biology 11, 1143-1149. A compound inhibiting the activity of GADLOR 1 and/or GADLOR 2 may be, for example, an antisense molecule, siRNA, shRNA, antibody, ribozyme, aptamer, or small molecule. These and other compounds will be further detailed herein below.

The efficiency of an inhibiting said compound can be quantified by methods comparing the level of activity in the presence of the inhibitor to that in the absence of the inhibitor. For example, the change in the amount of GADLOR 1 and/or GADLOR 2 formed may be used in the measurement of its activity. As a further example, a reduction in the amount of BNP and/or RCAN1.4 formed may be used in the measurement of its activity (noting that the upregulation of GADLOR 1 and GADLOR 2 is shown in the examples to be accompanied by the upregulation of BNP and RCAN1.4). As another example, an increase in the activation of the kinases p38 and/or Akt formed may be used in the measurement of its activity (noting that the upregulation of GADLOR 1 and GADLOR 2 is shown in the examples to be accompanied by the downregulation of the activation of p38 and Akt). As a further example, the change in the amount of GADLOR 1 and/or GADLOR 2 formed may be used in the measurement of its activity. Such methods may be effected in high-throughput format in order to test the efficiency of several inhibiting compounds simultaneously. High-throughput assays, independently of being biochemical, cellular or other assays, generally may be performed in wells of microtiter plates, wherein each plate may contain 96, 384 or 1536 wells. Handling of the plates, including incubation at temperatures other than ambient temperature, and bringing into contact of test compounds with the assay mixture is preferably effected by one or more computer-controlled robotic systems including pipetting devices. In case large libraries of test compounds are to be screened and/or screening is to be effected within short time, mixtures of, for example 10, 20, 30, 40, 50 or 100 test compounds may be added to each well. In case a well exhibits the expected activity, said mixture of test compounds may be de-convoluted to identify the one or more test compounds in said mixture giving rise to said activity.

The compounds inhibiting the expression and/or the activity of GADLOR 1 and/or GADLOR 2 may be formulated as vesicles, such as liposomes or exososmes. Liposomes have attracted great interest because of their specificity and the duration of action they offer from the standpoint of drug delivery. Liposomal delivery systems have been used to effectively deliver nucleic acids, such as siRNA in vivo into cells (Zimmermann et al. (2006) Nature, 441:111-114). Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are phagocytosed by macrophages and other cells in vivo. Exosomes are lipid packages which can carry a variety of different molecules including RNA (Alexander et al. (2015), Nat Commun; 6:7321). The exosomes including the molecules comprised therein can be taken up by recipient cells. Hence, exosomes are important mediators of intercellular communication and regulators of the cellular niche. Exosomes are useful for diagnostic and therapeutic purposes, since they can be used as drug delivery vehicles.

The compounds inhibiting the expression and/or the activity of GADLOR 1 and/or GADLOR 2 can be administered to the subject at a suitable dose. The dosage regimen will be determined by the attending physician and clinical factors. As is well known in the medical art, dosages for any one patient depend upon many factors, including the patient's size, body surface area, age, the particular compound to be administered, sex, time and route of administration, general health, and other drugs being administered concurrently. The therapeutically effective amount for a given situation will readily be determined by routine experimentation and is within the skills and judgement of the ordinary clinician or physician. Generally, the regimen as a regular administration of the pharmaceutical composition should be in the range of 1 μg to 5 g units per day. However, a more preferred dosage is in the range of 0.01 mg to 100 mg, even more preferably 0.01 mg to 50 mg and most preferably 0.01 mg to 10 mg per day. Furthermore, if for example said compound comprises or is an nucleic acid molecule, such as an siRNA, the total pharmaceutically effective amount of pharmaceutical composition administered will typically be less than about 75 mg per kg of body weight, such as for example less than about 70, 60, 50, 40, 30, 20, 10, 5, 2, 1, 0.5, 0.1, 0.05, 0.01, 0.005, 0.001, or 0.0005 mg per kg of body weight. More preferably, the amount will be less than 2000 nmol of nucleic acid molecule per kg of body weight, such as for example less than 1500, 750, 300, 150, 75, 15, 7.5, 1.5, 0.75, 0.15, 0.075, 0.015, 0.0075, 0.0015, 0.00075 or 0.00015 nmol per kg of body weight.

The length of treatment needed to observe changes and the interval following treatment for responses to occur vary depending on the desired effect. The particular amounts may be determined by conventional tests which are well known to the person skilled in the art. Suitable tests are, for example, described in Tamhane and Logan (2002), "Multiple Test Procedures for Identifying the Minimum Effective and Maximum Safe Doses of a Drug", Journal of the American statistical association, 97(457):1-9.

The compounds inhibiting the expression and/or the activity of GADLOR 1 and/or GADLOR 2 are preferably admixed with a pharmaceutically acceptable carrier or excipient to form a pharmaceutical composition. By "pharmaceutically acceptable carrier or excipient" is meant a non-toxic solid, semisolid or liquid filler, diluent, encapsulating material or formulation auxiliary of any type (see also Handbook of Pharmaceutical Excipients 6ed. 2010, Published by the Pharmaceutical Press). The compounds inhibiting the expression and/or the activity of GADLOR 1 and/or GADLOR 2 or the pharmaceutical composition may be administered, for example, orally, parenterally, such as subcutaneously, intravenously, intramuscularly, intraperitoneally, intrathecally, transdermally, transmucosally, subdurally, locally or topically via iontopheresis, sublingually, by inhalation spray, aerosol or rectally and the like in dosage unit formulations optionally comprising conventional pharmaceutically acceptable carriers or excipients.

The term cardiac remodelling is defined herein as an alteration in the structure (e.g., dimensions, mass, shape) of the heart. Cardiac remodelling may occur in response to hemodynamic load and/or cardiac injury in association with neurohormonal activation. Remodelling may be described as physiologic or pathologic. For instance, pathologic (or unhealthy) cardiac remodelling is to be held distinct from physiologic (or healthy) cardiac remodelling (such cardiac remodelling or "athlete's heart") which is a normal response of the heart, for example, in response to healthy exercise or pregnancy. Among healthy subjects, rowers or cyclists tend to have the largest hearts, with an average left ventricular wall thickness of 1.3 centimeters, compared to 1.1 centimeters in average adults. Cardiac remodelling is in accordance with the invention also unhealthy cardiac remodelling or pathological remodelling, such as cardiac remodelling in response to stress or disease, e.g., hypertension, heart muscle injury (myocardial infarction), heart failure or neurohormones. The remodelling process preferably includes increases in myocardial mass.

The term "nucleic acid sequence" or "nucleotide sequence" or "polynucleotide sequence", in accordance with the present invention, includes DNA and RNA. SEQ ID NOs 1 to 3 are sequences of the lncRNA GADLOR 1 and SEQ ID NOs 4 to 6 are sequences of the lncRNA GADLOR 2. SEQ ID NOs 1 to 6 are therefore single-stranded RNA sequences. As will be further detailed herein below, nucleotide-based compounds inhibiting the expression of GADLOR 1 and/or 2 may comprise DNA sequences (e.g. LNA GapmeRs) or RNA sequences (e.g. siRNAs). As will be also further detailed herein below, nucleotide-based compounds inhibiting the expression of GADLOR 1 and/or 2 may be single stranded (e.g. LNA GapmeRs) or double-stranded (e.g. siRNAs). Short "nucleic acid sequences" are also referred to herein as "oligonucleotide sequences". Oligonucleotide sequences are less than 50 nucleotides in length, preferably less than 40 nucleotides and most preferably less than 30 nucleotides.

Capillary endothelial cells modulate myocardial growth and function during pathological stress, but it is unknown how and whether this contributes to the formation of heart failure. As is shown in the examples herein below, the endothelial cell transcription factor GATA2 is downregulated in human failing myocardium. Endothelial GATA2 knock-out (G2-EC-KO) mice develop heart failure and defective myocardial signal-transduction during pressure overload, indicating that the GATA2 downregulation is maladaptive. Heart failure and perturbed signalling in G2-EC-KO mice is induced by strong upregulation of the two endothelial cell derived lncRNAs GADLOR 1 and 2. Mechanistically, the GADLOR 1 and 2 lncRNAs transfer from endothelial cells to cardiomyocytes via exosomes, where they bind the Ras-like protein TC21 and block downstream stress-induced signalling. Therefore, lncRNAs can contribute to disease as paracrine effectors of signal-transduction. It is furthermore shown in the examples of this application that the administration of effect of GADLOR 1 and 2 prior to TCA surgery of mice induces cardiac function and cardiac remodelling. The TAC mouse model is well-established model for cardiac remodelling (Mei et al. (2006), Clin Exp Pharmacol Physiol.; 33(9):773-9.). Increased GADLOR 1 and 2 levels in the myocardium and serum of human heart failure patients were observed, thereby showing that the findings in mouse can be transferred to humans and other mammals. Hence, a direct effect of GADLOR 1 and 2 on cardiac remodelling is demonstrated in the examples herein below. GADLOR 1 and 2 are therefore prospective therapeutic targets for treating and preventing cardiac remodelling.

In accordance with a preferred embodiment of the first aspect of the invention, the cardiac remodelling is Heart Failure with preserved Ejection Fraction (HFpEF), Heart Failure with reduced Ejection Fraction (HFrEF), myocardial infarction related cardiac remodelling, a genetic cardiac disease associated cardiac remodelling, cardiac hypertrophy and/or cardiac dysfunction related cardiac remodelling.

Among this list of cardiac remodelling conditions Heart Failure with preserved Ejection Fraction (HFpEF), Heart Failure with reduced Ejection Fraction (HFrEF) are more preferred. As will be described in more detail in the following, all heart conditions listed in this preferred embodiment are associated with cardiac remodelling and therefore can be treated or prevented in accordance with the present invention by a compound inhibiting the expression and/or the activity of GADLOR 1 and/or GADLOR 2.

Heart Failure with preserved Ejection Fraction (HFpEF) (also referred to as diastolic heart failure) is commonly understood as manifestation of signs and symptoms of heart failure with a normal ejection fraction (>50%). HFpEF is characterized by cardiac remodelling, in particular a decrease in left ventricular compliance, leading to increased pressure in the left ventricle. Accordingly, concentric remodelling (with or without LV hypertrophy) is seen in many HFpEF patients. Also an increased left atrial size is often seen with HFpEF as a result of the poor left ventricular diastolic function. There is an increased risk for the development of congestive heart failure, atrial fibrillation, and pulmonary hypertension. Risk factors are hypertension, hyperlipidemia, diabetes, smoking, and obstructive sleep apnea. Morbidity and mortality in HFpEF patients are similar to values observed in patients with heart failure (HF) and reduced EF (i.e. HFrEF patients). However, so far no effective treatment has been identified for HFpEF (Borlaug and Paulus et al. (2014), Eur Heart J., 32(6):670-679). For this reason the treatment means and methods disclosed herein are of particular importance for HFpEF patients or patients being at risk of becoming HFpEF.

Heart Failure with reduced Ejection Fraction (HFrEF) (also referred to as systolic heart failure) is commonly understood as manifestation of signs and symptoms of heart failure with an ejection fraction less than 40%. HFrEF generally occurs when the left ventricle is dilated and enlarged with poor systolic function. Around 50% of HF patients have a HFpEF and around 50% of heart failure patients have a HFrEF. Just as HfpEF, HFrEF is characterized by cardiac remodelling, in particular a decrease in left ventricular compliance, leading to increased pressure in the left ventricle.

Myocardial infarction (MI) is commonly known as a heart attack. MI occurs when blood flow stops to a part of the heart causing damage to the heart muscle. After an MI typically postinfarction cardiac remodelling is observed. In more detail, the acute loss of myocardium caused by the MI results in an abrupt increase in loading conditions that induces a unique pattern of remodelling involving the infarcted border zone and remote noninfarcted myocardium. Myocyte necrosis and the resultant increase in load trigger a cascade of biochemical intracellular signaling processes that initiates and subsequently modulates reparative changes, which include dilatation, hypertrophy, and the formation of a discrete collagen scar. In particular, ventricular remodelling may continue for weeks or months after the MI until the distending forces are counterbalanced by the tensile strength of the collagen scar. The postinfarction cardiac remodelling after MI is referred to herein as "myocardial infarction related cardiac remodelling".

A genetic (or inherited) cardiac disease is caused by changes in genes that are passed from generation to generation. Many different types of heart diseases can be inherited. Examples include conditions that affect the heart muscle, called inherited cardiomyopathies, such as hypertrophic cardiomyopathy, dilated cardiomyopathy, Morbus Fabry disease, amyloidoses and arrhythmogenic right ventricular cardiomyopathy. These examples also involve cardiac remodelling. Specific examples of genetic cardiac diseases which are associated with cardiac remodelling include but are not limited to hereditary hypertrophic cardiomyopythies (such as familial hypertrophic cardiomyopathy) or Morbus Fabry disease.

Cardiac hypertrophy is defined as an increase in size of the heart without any increase in myocyte number. This results in a thickening of the heart walls. Pathological cardiac hypertrophy occurs in response to haemodynamic overload due to different forms of stress, such as hypertension, valve disease, and myocardial infarction (MI). Prolonged hypertrophic growth of the heart results in cardiac arrhythmias, heart failure and may lead to sudden death (Frey and Olson (2003), Annu Rev Physiol; 65: 45-79). Thus, cardiac hypertrophy is in accordance with the invention unhealthy cardiac hypertrophy (or pathological hypertrophy), such as cardiac hypertrophy in response to stress or disease, e.g., hypertension, heart muscle injury (myocardial infarction), heart failure or neurohormones.

Cardiac dysfunction is defined as an alteration in the relationship between preload (often defined by left ventricular filling pressure) and stroke volume of the heart. Cardiac dysfunction may lead to cardiac remodelling and vice versa.

In accordance with another preferred embodiment of the first aspect of the invention, the compound inhibiting the expression and/or the activity of the lncRNA is a small molecule inhibitor, a nucleotide-based inhibitor or an amino acid-based inhibitor.

A small molecule inhibitor is a low molecular weight organic compound which is by definition not a polymer. The small molecule of the invention is a molecule that binds with high affinity to GADLOR 1 and/or GADLOR 2 and in addition inhibits the activity of GADLOR 1 and/or GADLOR 2. The upper molecular weight limit for a small molecule is preferably 1500 Da, more preferably 1000 Da and most preferably 800 Da which allows for the possibility to rapidly diffuse across cell membranes so that they can reach intracellular sites of action. Libraries of small organic molecules are screened by high-throughput techniques with a specific target molecule, in the present case the lncRNA GADLOR 1 and/or GADLOR 2, and preferably a polynucleotide selected from the group consisting of SEQ ID NOs 1 to 6.

A nucleotide-based inhibitor comprises or consists of a nucleic acid molecule. The nucleic acid is preferably complementary to a nucleic acid sequence of at least 12 contiguous nucleotides of one or more sequences of SEQ ID NOs 1 to 6 or a sequence being at least 75% identical to one or more sequences of SEQ ID NOs 1 to 6. The nucleotide-based inhibitor may comprise or consist of RNA, DNA or both. The nucleotide-based inhibitor of the invention is a molecule that binds specifically to GADLOR 1 or GADLOR 2 and in addition inhibits the activity of GADLOR 1 or GADLOR 2. As used herein specific binding means that the inhibitor specifically targets the lncRNA GADLOR 1 or GADLOR 2 and does substantially not exert any off target inhibitory effects, in particular on other cellular nucleic acid molecules.

An amino acid-based inhibitor comprises or consists of a (poly)peptide/protein having preferably an amino acid sequence of at least 25, more preferably at least 50 amino acids. The amino acid-based inhibitor of the invention is a molecule that binds specifically to GADLOR 1 or GADLOR 2 and in addition inhibits the activity of GADLOR 1 or GADLOR 2. The amino acid-based inhibitor preferably comprises natural amino acids but may also comprise unnatural amino acids. The amino acid-based inhibitor is preferably selected or designed such that it specifically binds to a nucleic acid sequence selected from one or more of SEQ ID NOs 1 to 3 (GADLOR 1) or a sequence being at least 75% identical to one or more of SEQ ID NOs 1 to 3, or from one or more of SEQ ID NOs 4 to 6 (GADLOR 2) or a sequence being at least 75% identical to one or more of SEQ ID NOs 4 to 6.

In accordance with a more preferred embodiment of the first aspect of the present invention, the nucleotide-based inhibitor or amino acid-based inhibitor is an aptamer, a ribozyme, a siRNA, a shRNA or an antisense oligonucleotide and the amino acid-based inhibitor is an antibody or a protein drug.

The aptamer, ribozyme, antibody, protein drug, siRNA, a shRNA or an antisense oligonucleotide of this embodiment specifically bind to GADLOR 1 or GADLOR 2, thereby inhibiting the activity of GADLOR 1 or GADLOR 2.

The term "aptamer" in accordance with the present invention refers to DNA or RNA molecules being either in the natural D-conformation or in the L-conformation ("spiegelmer") that have been selected from random pools based on their ability to bind other molecules. Aptamers have been selected which bind nucleic acid, proteins, small organic compounds, and even entire organisms. A database of aptamers is maintained at http://aptamer.icmb.utexas.edu/. More specifically, aptamers can be classified as DNA or RNA aptamers or peptide aptamers. Whereas the former consist of (usually short) strands of oligonucleotides, the latter consist of a short variable peptide domain, attached at both ends to a protein scaffold. Nucleic acid aptamers are nucleic acid species that have been engineered through repeated rounds of in vitro selection or equivalently, SELEX (systematic evolution of ligands by exponential enrichment) to bind to various molecular targets such as small molecules, proteins, nucleic acids, and even cells, tissues and organisms. The molecular target envisaged by the present invention is a nucleic acid, namely the lncRNA GADLOR 1 or GADLOR 2. Hence, aptamers can be produced against the target molecule of the invention. Aptamers offer the utility for biotechnological and therapeutic applications as they offer molecular recognition properties that rival those of the commonly used biomolecules, in particular antibodies. In addition to their discriminate recognition, aptamers offer advantages over antibodies as they can be engineered completely in a test tube, are readily produced by chemical synthesis, possess desirable storage properties, and elicit little or no immunogenicity in therapeutic applications. Non-modified aptamers are cleared rapidly from the bloodstream, with a half-life of minutes to hours, mainly due to nuclease degradation and clearance from the body by the kidneys, a result of the aptamer's inherently low molecular weight. The rapid clearance of aptamers can be an advantage in applications such as in vivo diagnostic imaging. Several modifications, such as 2'-fluorine-substituted pyrimidines, polyethylene glycol (PEG) linkage, etc. are available to scientists with which the half-life of aptamers easily can be increased to the day or even week time scale.

The term "ribozymes" refers to RNA molecules that act as enzymes in the absence of proteins. These RNA molecules act catalytic or autocatalytic and are capable of cleaving e.g. other RNAs at specific target sites but they have also been found to catalyze the aminotransferase activity of the ribosome. Selection of appropriate target sites and corresponding ribozymes can be done as described for example in Zaher and Unrau (2007), RNA, 13 (7): 1017-1026. Examples of well-characterized small self-cleaving RNAs are the hammerhead, hairpin, hepatitis delta virus, and in vitro-selected lead-dependent ribozymes. The organization of these small catalysts is in contrast to that of larger ribozymes, such as the group I intron. The principle of catalytic self-cleavage has become well established in the last 10 years. The hammerhead ribozymes are characterized best among the RNA molecules with ribozyme activity. Since it was shown that hammerhead structures can be integrated into heterologous RNA sequences and that ribozyme activity can thereby be transferred to these molecules, it appears that catalytic sequences for almost any target sequence can be created, provided the target sequence contains a potential matching cleavage site. The basic principle of constructing hammerhead ribozymes is as follows: An interesting region of the RNA, which contains the GUC (or CUC) triplet, is selected. Two oligonucleotide strands, each with 6 to 8 nucleotides, are taken and the catalytic hammerhead sequence is inserted between them. Molecules of this type were synthesized for numerous target sequences. They showed catalytic activity in vitro and in some cases also in vivo. The best results are usually obtained with short ribozymes and target sequences. Since the target sequence is in accordance with the present invention a RNA sequence, GADLOR 1 and GADLOR 2 are a bona fide target for the generation of ribozymes being capable to specifically cleave GADLOR 1 or GADLOR 2.

The aptamers and ribozymes may comprise modified nucleotides, such as locked nucleic acids (LNAs).

The term "antibody" as used in accordance with the present invention comprises, for example, polyclonal or monoclonal antibodies. Furthermore, also derivatives or fragments thereof, which still retain the binding specificity, are comprised in the term "antibody". Antibody fragments or derivatives comprise, inter alia, Fab or Fab' fragments, Fd, $F(ab')_2$, Fv or scFv fragments, single domain $V_H$ or V-like domains, such as VhH or V-NAR-domains, as well as multimeric formats such as minibodies, diabodies, tribodies, tetrabodies or chemically conjugated Fab'-multimers (see, for example, Altshuler et al., Biochemistry (Mosc). 2010 December; 75(13):1584-605, Holliger and Hudson, Nat Biotechnol., 2005; 23(9):1126-36). The term "antibody" also includes embodiments such as chimeric (human constant domain, non-human variable domain), single chain and humanized (human antibody with the exception of non-human CDRs) antibodies. Various techniques for the production of antibodies and fragments thereof are well known in the art and described, e.g. in Altshuler et al., Biochemistry (Mosc). 2010 December; 75(13):1584-605. Thus, polyclonal antibodies can be obtained from the blood of an animal following immunisation with an antigen in mixture with additives and adjuvans and monoclonal antibodies can be produced by any technique which provides antibodies produced by continuous cell line cultures. Examples for such techniques are described, e.g. Harlow and Lane, Antibodies: A Laboratory Manual, Cold Spring Harbor Laboratory Press, 1988 and Harlow and Lane, Using Antibodies: A Laboratory Manual, Cold Spring Harbor Laboratory Press, 1999 and include the hybridoma technique originally described by Kohler and Milstein, Nature 256 (1975), 495-497, the trioma technique, the human B-cell hybridoma technique (see e.g. Kozbor, Immunology Today 4 (1983), 72; Milstein, C (1999), BioEssays 21 (11): 966-73.) and the EBV-hybridoma technique to produce human monoclonal antibodies (Cole et al., Monoclonal Antibodies and Cancer Therapy, Alan R. Liss, Inc. (1985), 77-96). Furthermore, recombinant antibodies may be obtained from monoclonal antibodies or can be prepared de novo using various display methods such as phage, ribosomal, mRNA, or cell display. A suitable system for the expression of the recombinant (humanized) antibodies or fragments thereof may be selected from, for example, bacteria, yeast, insects, mammalian cell lines or transgenic animals or plants (see, e.g., U.S. Pat. No. 6,080,560; Holliger and Hudson, Nat Biotechnol., 2005; 23(9):1126-36). Further, techniques described for the production of single chain antibodies (see, inter alia, U.S. Pat. No. 4,946,778) can be adapted to produce single chain antibodies specific for the target of this invention. Surface plasmon resonance as employed in the BIAcore system can be used to increase the efficiency of phage antibodies.

The term "protein drug" designates designer drugs that are derivatives of human proteins. These proteins are used as scaffold to create a protein drug by well-established screening procedures (see Tomlinson et al (2004), Nature Biotechnology, 22(5): 521-522). Non-limiting examples of human proteins which serve as a scaffold for designing protein drugs are transferrin, C-type lectins, trinectins, domain antibodies, kunitz domains, lipocalins and the Fyn SH3 domain.

The antisense technology for the downregulation of RNA is well-established and widely used in the art to treat various diseases. The basic idea of the antisense technology is the use of oligonucleotides for silencing a selected target RNA through the exquisite specificity of complementary-based pairing (Re, Ochsner J. 2000 October; 2(4): 233-236). Herein below details on the antisense construct compound classes of siRNAs, shRNAs and antisense oligonucleotides will be provided. As will be further detailed herein below, antisense oligonucleotides are single stranded antisense constructs while siRNAs and shRNAs are double stranded antisense constructs with one strand comprising an antisense oligonucleotide sequence being (i.e. the so-called antisense strand). All these compound classes may be used to achieve downregulation or inhibition of a target RNA.

In accordance with the present invention the target of antisense constructs in general as well as all the specific classes of antisense constructs being described herein is the lncRNA GADLOR 1 or GADLOR 2. Accordingly, the target is preferably a nucleic acid sequence selected from one or more sequences of SEQ ID NOs 1 to 6 or a sequence being at least 75% identical to one or more sequences of SEQ ID NOs 1 to 6.

Also with respect to any amino acid-based inhibitor, nucleotide-based inhibitor or antisense construct being described herein the sequence identity of at least 75% to one or more sequences of SEQ ID NOs 1 to 6 is with increasing preference at least 80%, at least 85%, at least 90%, at least 95%, at least 96%, at least 97%, at least 98%, at least 99% and at least 99.5%. The sequence identity can be selected separately for each of the GADLOR 1 sequences of SEQ ID NOs 1 to 3 as well as for each of the GADLOR 2 sequences of SEQ ID NOs 4 to 6. Preferred examples of nucleic acid sequences being at least 75% identical to one or more sequences of SEQ ID NOs 1 to 6 are nucleic acid sequences differing with increasing preference by no more than 10, such as 5, 4, 3, 2 or 1 nucleotide(s) from any one of SEQ ID NOs 1 to 6. The nucleotide differences may be the addition, deletion and/or substitution of nucleotide(s).

The term "siRNA" in accordance with the present invention refers to small interfering RNA, also known as short interfering RNA or silencing RNA. siRNAs are a class of 12 to 30, preferably 18 to 30, more preferably 20 to 25, and most preferred 21 to 23 or 21 nucleotide-long double-stranded RNA molecules that play a variety of roles in biology. Most notably, siRNA is involved in the RNA interference (RNAi) pathway where the siRNA interferes with the expression of a specific gene. In addition to their role in the RNAi pathway, siRNAs also act in RNAi-related pathways, e.g. as an antiviral mechanism or in shaping the chromatin structure of a genome. siRNAs have a well defined structure: a short double-strand of RNA (dsRNA), advantageously with at least one RNA strand having an overhang. Each strand typically has a 5' phosphate group and a 3' hydroxyl (—OH) group. This structure is the result of processing by dicer, an enzyme that converts either long dsRNAs or small hairpin RNAs into siRNAs. siRNAs can also be exogenously (artificially) introduced into cells to bring about the specific knockdown of a gene of interest. Thus, any gene of which the sequence is known can in principle be targeted based on sequence complementarity with an appropriately tailored siRNA. The double-stranded RNA molecule or a metabolic processing product thereof is capable of mediating target-specific nucleic acid modifications, particularly RNA interference and/or DNA methylation. Also preferably at least one RNA strand has a 5'- and/or 3'-overhang. Preferably, one or both ends of the double-strand have a 3'-overhang from 1-5 nucleotides, more preferably from 1-3 nucleotides and most preferably 2 nucleotides. In general, any RNA molecule suitable to act as siRNA is envisioned in the present invention. The most efficient silencing was so far obtained with siRNA duplexes composed of 21-nt sense and 21-nt antisense strands, paired in a manner to have 2-nt 3'-overhangs. The sequence of the 2-nt 3' overhang makes a small contribution to the specificity of target recognition restricted to the unpaired nucleotide adjacent to the first base pair (Elbashir et al. Nature. 2001 May 24; 411(6836):494-8). 2'-deoxynucleotides in the 3' overhangs are as efficient as ribonucleotides, but are often cheaper to synthesize and probably more nuclease resistant. The siRNA according to the invention comprises an antisense strand which comprises or consists of a sequence which is with increasing preference complementary to at least 13 nucleotides, at least 14 nucleotides, at least 15 nucleotides, at least 16 nucleotides, at least 17 nucleotides, at least 18 nucleotides, at least 19 nucleotides, at least 20 nucleotides, or at least 21 nucleotides of one or more selected from SEQ ID NOs 1 to 6 or a sequence being at least 75% identical to one or more sequences of SEQ ID NOs 1 to 6. These at least 13 nucleotides, at least 14 nucleotides, at least 15 nucleotides, at least 16 nucleotides, at least 17 nucleotides, at least 18 nucleotides, at least 19 nucleotides, at least 20 nucleotides, or at least 21 nucleotides are preferably a contiguous part of one or more selected from SEQ ID NOs 1 to 6 or a sequence being at least 75% identical to one or more sequences of SEQ ID NOs 1 to 6, i.e. the nucleotides are consecutive in the respective SEQ ID NO.

A preferred example of a siRNA is an Endoribonuclease-prepared siRNA (esiRNA). An esiRNA is a mixture of siRNA oligos resulting from cleavage of a long double-stranded RNA (dsRNA) with an endoribonuclease such as *Escherichia coli* RNase III or dicer. esiRNAs are an alternative concept to the usage of chemically synthesized siRNA for RNA Interference (RNAi). For the generation of esiRNAs a cDNA of an lncRNA template may be amplified by PCR and tagged with two bacteriophage-promotor sequences. RNA polymerase is then used to generate long double stranded RNA that is complementary to the target-gene cDNA. This complementary RNA may be subsequently digested with RNase III from *Escherichia coli* to generate short overlapping fragments of siRNAs with a length between 18-25 base pairs. This complex mixture of short double stranded RNAs is similar to the mixture generated by dicer cleavage in vivo and is therefore called endoribonuclease-prepared siRNA or short esiRNA. Hence, esiRNA are a heterogeneous mixture of siRNAs that all target the same mRNA sequence. esiRNAs lead to highly specific and effective gene silencing.

A "shRNA" in accordance with the present invention is a short hairpin RNA, which is a sequence of RNA that makes a (tight) hairpin turn that can also be used to silence gene expression via RNA interference. shRNA preferably utilizes the U6 promoter for its expression. The shRNA hairpin structure is cleaved by the cellular machinery into siRNA, which is then bound to the RNA-induced silencing complex (RISC). This complex binds to and cleaves mRNAs which match the shRNA that is bound to it. The shRNA according to the invention comprises an antisense strand which comprises or consists of a sequence which is with increasing preference complementary to at least 13 nucleotides, at least 14 nucleotides, at least 15 nucleotides, at least 16 nucleotides, at least 17 nucleotides, at least 18 nucleotides, at least 19 nucleotides, at least 20 nucleotides, at least 21 nucleotides of one or more selected from SEQ ID NOs 1 to 6 or a sequence being at least 75% identical to one or more sequences of SEQ ID NOs 1 to 6. These at least 13 nucleotides, at least 14 nucleotides, at least 15 nucleotides, at least 16 nucleotides, at least 17 nucleotides, at least 18 nucleotides, at least 19 nucleotides, at least 20 nucleotides, or at least 21 nucleotides are preferably a contiguous part of one or more selected from SEQ ID NOs 1 to 6 or a sequence being at least 75% identical to one or more sequences of SEQ ID NOs 1 to 6, i.e. the nucleotides are consecutive in the respective SEQ ID NO.

The term "antisense oligonucleotide" in accordance with the present invention refers to a single-stranded nucleotide sequence being complementary by virtue of Watson-Crick base pair hybridization to the lncRNA GADLOR 1 or GADLOR 2 whereby the activity of GADLOR 1 or GADLOR 2 is blocked. The antisense oligonucleotides may be unmodified or chemically modified. In general, they are relatively short (preferably between 13 and 25 nucleotides). Moreover, they are specific for GADLOR 1 or GADLOR 2, i.e. they hybridize to a unique sequence in the total pool of targets present in the target cells/organism. The antisense oligonucleotide according to the invention comprises or consists a sequence which is with increasing preference complementary to at least 13 nucleotides, at least 14 nucleotides, at least 15 nucleotides, at least 16 nucleotides, at least 17 nucleotides, at least 18 nucleotides, at least 19 nucleotides, at least 20 nucleotides, at least 21 nucleotides, at least 22 nucleotides, at least 23 nucleotides, at least 24 nucleotides, or at least 25 nucleotides of one or more selected from SEQ ID NOs 1 to 6 or a sequence being at least 75% identical to one or more sequences of SEQ ID NOs 1 to 6. These at least 13 nucleotides, at least 14 nucleotides, at least 15 nucleotides, at least 16 nucleotides, at least 17 nucleotides, at least 18 nucleotides, at least 19 nucleotides, at least 20 nucleotides, at least 21 nucleotides, at least 22 nucleotides, at least 23 nucleotides, at least 24 nucleotides, or at least 25 nucleotides are preferably a contiguous part of one or more selected from SEQ ID NOs 1 to 6 or a sequence being at least 75% identical to one or more sequences of SEQ ID NOs 1 to 6, i.e. the nucleotides are consecutive in the respective SEQ ID NO.

The antisense oligonucleotide is preferably a LNA-GapmeR, an Antagomir, or an antimiR. LNA-GapmeRs or simply GapmeRs are potent antisense oligonucleotides used for highly efficient inhibition of mRNA and lncRNA function. GapmeRs function by RNase H dependent degradation of complementary RNA targets. They are an excellent alternative to siRNA for knockdown of mRNA and lncRNA. They are advantageously taken up by cell without transfection reagents. GapmeRs contain a central stretch of DNA monomers flanked by blocks of LNAs. The GapmeRs are preferably 14-16 nucleotides in length and are optionally fully phosphorothioated. The DNA gap activates the RNAse H-mediated degradation of targeted RNAs and is also suitable to target transcripts directly in the nucleus. The LNA-GapmeR according to the invention comprises a sequence which is with increasing preference complementary to at least 13 nucleotides, at least 14 nucleotides, or at least 15 nucleotides of one or more selected from SEQ ID NOs 1 to 6 or a sequence being at least 75% identical to one or more sequences of SEQ ID NOs 1 to 6. These at least 13 nucleotides, at least 14 nucleotides, or at least 15 nucleotides are preferably a contiguous part of one or more selected from SEQ ID NOs 1 to 6 or a sequence being at least 75% identical to one or more sequences of SEQ ID NOs 1 to 6, i.e. the nucleotides are consecutive in the respective SEQ ID NO. The LNA-GapmeR against GADLOR 1 according to the invention preferably comprises a sequence which is complementary to SEQ ID NO: 7 (GGAUACUAGGCUUAGGACAUA) or SEQ ID NO: 8 (UCUCAAUCAUCUUGCA). SEQ ID NO: 7 can be found in the human GADLOR 1 of SEQ ID NO: 1 and SEQ ID NO: 8 in the mouse GADLOR 1 of SEQ ID NO: 2. The LNA-GapmeR against GADLOR 2 according to the invention preferably comprises a sequence which is complementary to SEQ ID NO: 9 (AGCCUCUAUCCUUACU) or SEQ ID NO: 10 (AACCUCUAUCCUUGA). SEQ ID NO: 9 can be found in the human GADLOR 2 of SEQ ID NO: 4 and SEQ ID NO: 10 in the mouse GADLOR 2 of SEQ ID NO: 5. The LNA-GapmeR technology is well established. LNA-GapmeRs are routinely designed using established algorithms. LNA-GapmeRs to a selected target are commercially available including positive and negative controls, for example, from Exiqon.

As mentioned, AntimiRs are oligonucleotide inhibitors that were initially designed to be complementary to a miRNA. AntimiRs against miRNAs have been used extensively as tools to gain understanding of specific miRNA functions and as potential therapeutics. As used herein, the AntimiRs are designed to be complementary to the lncRNA GADLOR 1 or GADLOR 2. AntimiRs are preferably 14 to 23 nucleotides in length. An AntimiR according to the invention more preferably comprises or consists a sequence which is with increasing preference complementary to at least 15 nucleotides, at least 16 nucleotides, at least 17 nucleotides, at least 18 nucleotides, at least 19 nucleotides, at least 20 nucleotides, at least 21 nucleotides, at least 22 nucleotides, or at least 23 nucleotides of one or more selected from SEQ ID NOs 1 to 6 or a sequence being at least 75% identical to one or more sequences of SEQ ID NOs 1 to 6. These at least 15 nucleotides, at least 16 nucleotides, at least 17 nucleotides, at least 18 nucleotides, at least 19 nucleotides, at least 20 nucleotides, at least 21 nucleotides, at least 22 nucleotides, or at least 23 nucleotides are preferably a contiguous part of one or more selected from SEQ ID NOs 1 to 6 or a sequence being at least 75% identical to one or more sequences of SEQ ID NOs 1 to 6, i.e. the nucleotides are consecutive in the respective SEQ ID NO.

AntimiRs are preferably AntagomiRs. AntagomiRs are synthetic 2-O-methyl RNA oligonucleotides, preferably of 21 to 23 nucleotides which are preferably fully complementary to the selected target RNA. While AntagomiRs were initially designed against miRNAs they may also be designed against lncRNAs. The AntagomiRs according to the invention therefore preferably comprises a sequence being complementary to 21 to 23 nucleotides of one or more selected from SEQ ID NOs 1 to 6 or a sequence being at least 75% identical to one or more sequences of SEQ ID NOs 1 to 6. These 21 to 23 nucleotides are preferably complementary to a contiguous part of one or more selected from SEQ ID NOs 1 to 6 or a sequence being at least 75% identical to one or more sequences of SEQ ID NOs 1 to 6, i.e. the nucleotides are consecutive in the respective SEQ ID NO. AntagomiRs are preferably synthesized with 2'-OMe modified bases (2'-hydroxyl of the ribose is replaced with a methoxy group), phosphorothioate (phosphodiester linkages are changed to phosphorothioates) on the first two and last four bases, and an addition of cholesterol motif at 3' end through a hydroxyprolinol modified linkage. The addition of 2'-OMe and phosphorothioate modifications improve the bio-stability whereas cholesterol conjugation enhances distribution and cell permeation of the AntagomiRs.

Single-stranded antisense molecules (including antisense oligonucleotides, such as LNA-GapmeR, an Antagomir, an antimiR), siRNAs and shRNAs of the present invention are (also) preferably chemically synthesized using a conventional nucleic acid synthesizer. Suppliers of nucleic acid sequence synthesis reagents include Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK).

The ability of antisense molecules (including antisense oligonucleotides, such as LNA-GapmeR, an Antagomir, an antimiR), siRNA, and shRNA to potently, but reversibly, silence or inhibit a lncRNA in vivo makes these molecules particularly well suited for use in the pharmaceutical composition of the invention. Ways of administering siRNA to humans are described in De Fougerolles et al., Current Opinion in Pharmacology, 2008, 8:280-285. Accordingly, such pharmaceutical compositions may be administered directly formulated as a saline, via liposome based and polymer-based nanoparticle approaches, as conjugated or complexation pharmaceutical compositions, or via viral delivery systems. Direct administration comprises injection into tissue, intranasal and intratracheal administration. Liposome based and polymer-based nanoparticle approaches comprise the cationic lipid Genzyme Lipid (GL) 67, cationic liposomes, chitosan nanoparticles and cationic cell penetrating peptides (CPPs). Conjugated or complexation pharmaceutical compositions comprise PEI-complexed antisense molecules (including antisense oligonucleotides), siRNA, or shRNA. Further, viral delivery systems comprise influenza virus envelopes and virosomes.

The antisense molecules (including antisense oligonucleotides, such as LNA-GapmeR, an Antagomir, an antimiR), siRNAs, shRNAs may comprise modified nucleotides such as locked nucleic acids (LNAs). The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. Such oligomers are synthesized chemically and are commercially available. The locked ribose conformation enhances base stacking and backbone pre-organization. This significantly increases the hybridization properties (melting temperature) of oligonucleotides.

In accordance with an even more preferred embodiment of the first aspect of the present invention, the nucleotide-based inhibitor comprises (a) a nucleic acid sequence which comprises or consists of a nucleic acid sequence being complementary to at least 12 continuous nucleotides of a nucleic acid sequence selected from SEQ ID NOs 1 to 6 or a sequence being at least 75% identical thereto, (b) a nucleic acid sequence which comprises or consists of a nucleic acid sequence which is at least 70% identical to the complementary strand of one or more nucleic acid sequences selected from SEQ ID NOs 1 to 6, (c) a nucleic acid sequence which comprises or consists of a nucleic acid sequence according to (a) or (b), wherein the nucleic acid sequence is DNA or RNA, (d) an expression vector expressing the nucleic acid sequence as defined in any one of (a) to (c), preferably under the control of a myocardium-specific promoter and/or cardiac endothelial cell-specific promoter, or (e) a host comprising the expression vector of (d).

The nucleic acid sequences as defined in items (a) to (c) of this preferred embodiment comprise or consist of sequences being complementary to nucleotides of GADLOR 1 or GADLOR 2 as defined by one or more of sequences SEQ ID NOs 1 to 6 or a sequence being at least 70%/75% identical to one or more sequences of SEQ ID NOs 1 to 6. Hence, the nucleic acid sequences as defined in items (a) to (c) comprise or are antisense nucleic acid sequences.

The nucleic acid sequence according to item (a) of this further preferred embodiment of the invention comprises or consists of a sequence which is with increasing preference complementary to at least 13 nucleotides, at least 14 nucleotides, at least 15 nucleotides, at least 16 nucleotides, at least 17 nucleotides, at least 18 nucleotides, at least 19 nucleotides, at least 20 nucleotides, at least 21 nucleotides of one or more selected from SEQ ID NOs 1 to 6 or a sequence being at least 75% identical to one or more sequences of SEQ ID NOs 1 to 6. These at least 13 nucleotides, at least 14 nucleotides, at least 15 nucleotides, at least 16 nucleotides, at least 17 nucleotides, at least 18 nucleotides, at least 19 nucleotides, at least 20 nucleotides, or at least 21 nucleotides are preferably a contiguous part of one or more selected from SEQ ID NOs 1 to 6 or a sequence being at least 75% identical to one or more sequences of SEQ ID NOs 1 to 6, i.e. the nucleotides are consecutive in the respective SEQ ID NO. The format of the nucleic acid sequence according to item (a) is not particularly limited as long as it comprises or consists of at least 12 continuous nucleotides being complementary to a nucleic acid sequence selected from SEQ ID NOs 1 to 6 or a sequence being at least 75% identical to one or more sequences of SEQ ID NOs 1 to 6. The nucleic acid sequence according to item (a) comprises or consists of an antisense oligonucleotide. Hence, the nucleic acid sequence according to item (a) reflects the above-mentioned basic principle of the antisense technology which is the use of an oligonucleotide for silencing a selected target RNA through the exquisite specificity of complementary-based pairing. Therefore, it is to be understood that the nucleic acid sequence according to item (a) is preferably in the format of an siRNA, shRNA or an antisense oligonucleotide as defined herein above. The antisense oligonucleotides are preferably LNA-GapmeRs, AntagomiRs, or antimiRs as defined herein above.

The nucleic acid sequence according to item (b) requiring at least 70% identity to the complementary strand of one or more nucleic acid sequences selected from SEQ ID NOs 1 to 6 is considerably longer than the nucleic acid sequence according to item (a) which comprises an antisense oligonucleotide and comprises at least 12 continuous nucleotides of a nucleic acid sequence selected from SEQ ID NOs 1 to 6. Among SEQ ID NOs 1 to 6 SEQ ID NO: 4 is the shortest sequence and SEQ ID NO: 4 comprises 615 nucleotides. A sequence of at least 70% identity to the complementary strand of SEQ ID NO: 4 accordingly has to comprise at least 413 nucleotides. A nucleic acid sequence according to item (b) of the above preferred embodiment of the invention is capable of interacting with, more specifically hybridizing with the target lncRNA GADLOR 1 or GADLOR 2. By formation of the hybrid the function of the lncRNA GADLOR 1 or GADLOR 2 is reduced or blocked.

The sequence identity of the molecule according to item (b) in connection with a sequence selected from SEQ ID NOs 1 to 6 is with increasing preference at least 75%, at least 80%, at least 85%, at least 90%, at least 92.5%, at least 95%, at least 98%, at least 99% and 100%. The sequence identity in connection with each of SEQ ID NOs 1 to 6 can be individually selected. For instance, a non-limiting example is at least 90% in connection with SEQ ID NO: 1 and at least 95% in connection with SEQ ID NO: 2. Means and methods for determining sequence identity are known in the art. Preferably, the BLAST (Basic Local Alignment Search Tool) program is used for determining the sequence identity with regard to one or more sequences of SEQ ID NOs 1 to 6. Most preferred examples of nucleic acid sequences which comprise a nucleotide sequence which is at least 70% identical to the complementary strand of one or more sequences of SEQ ID NOs 1 to 6 are the complementary strands of SEQ ID NOs 1 to 6.

In the nucleic acid sequence according to item (c) the nucleotide sequences may be RNA or DNA. RNA or DNA encompasses chemically modified RNA nucleotides or DNA nucleotides.

As commonly known RNA comprises the nucleotide U while DNA comprises the nucleotide T.

In accordance with items (d) and (e) of the above preferred embodiment the inhibitor may also be an expression vector or host, respectively being capable of producing an nucleic acid sequence as defined in any one of items (a) to (c).

An expression vector may be a plasmid that is used to introduce a specific transcript into a target cell. Once the expression vector is inside the cell, the protein that is encoded by the gene is produced by the cellular-transcription and translation machinery ribosomal complexes. The plasmid is in general engineered to contain regulatory sequences that act as enhancer and/or promoter regions and lead to efficient transcription of the transcript. In particular for in vivo applications the expression vector preferably contains a myocardium-specific promoter and/or cardiac endothelial cell-specific promoter. Myocardium-specific promoters are known in the art, for example, from US 2004/0175699. Using a myocardium-specific promoter ensures that the nucleic acid sequence is only expressed in the heart muscle and may avoid potential unwanted side effects by expression in other organs. Promoters for cardiac endothelial cell-specific expression are as well known in the art, e.g., from Doetschman and Azhar (2012), Circ Res; 110(11), doi:10.1161/CIRCRESAHA.112.265066. Using a cardiac endothelial cell-specific promoter ensures that the nucleic acid sequence is only expressed in cardiac endothelial cells and may avoid potential unwanted side effects by expression in other cell-types of the heart.

Non-limiting examples of expression vectors include prokaryotic plasmid vectors, such as the pUC-series, pBluescript (Stratagene), the pET-series of expression vectors (Novagen) or pCRTOPO (Invitrogen) and vectors compatible with an expression in mammalian cells like pREP (Invitrogen), pcDNA3 (Invitrogen), pCEP4 (Invitrogen), pMClneo (Stratagene), pXT1 (Stratagene), pSG5 (Stratagene), EBO-pSV2neo, pBPV-1, pdBPVMMTneo, pRSVgpt, pRSVneo, pSV2-dhfr, plZD35, pLXIN, pSIR (Clontech), plRES-EGFP (Clontech), pEAK-10 (Edge Biosystems) pTriEx-Hygro (Novagen) and pCINeo (Promega). Examples for plasmid vectors suitable for *Pichia pastoris* comprise e.g. the plasmids pAO815, pPIC9K and pPIC3.5K (all Intvitrogen). For the formulation of a pharmaceutical composition a suitable vector is selected in accordance with good manufacturing practice. Such vectors are known in the art, for example, from Ausubel et al, Hum Gene Ther. 2011 April; 22(4):489-97 or Allay et al., Hum Gene Ther. May 2011; 22(5): 595-604.

A typical mammalian expression vector that may be used for in vitro or in vivo applications contains the promoter element, which mediates the initiation of transcription of mRNA, the protein coding sequence, and signals required for the termination of transcription and polyadenylation of the transcript. Moreover, elements such as origin of replication, drug resistance gene, regulators (as part of an inducible promoter) may also be included. The lac promoter is a typical inducible promoter, useful for prokaryotic cells, which can be induced using the lactose analogue isopropylthiol-b-D-galactoside ("IPTG"). For recombinant expression and secretion, the polynucleotide of interest may be ligated between e.g. the PelB leader signal, which directs the recombinant protein in the periplasm and the gene III in a phagemid called pHEN4 (described in Ghahroudi et al, 1997, FEBS Letters 414:521-526). Additional elements might include enhancers, Kozak sequences and intervening sequences flanked by donor and acceptor sites for RNA splicing. Highly efficient transcription can be achieved with the early and late promoters from SV40, the long terminal repeats (LTRs) from retroviruses, e.g., RSV, HTLVI, HIVI, and the early promoter of the cytomegalovirus (CMV). However, cellular elements can also be used (e.g., the human actin promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12MI (ATCC 67109). Alternatively, the recombinant (poly)peptide can be expressed in stable cell lines that contain the gene construct integrated into a chromosome. The co-transfection with a selectable marker such as dhfr, gpt, neomycin, hygromycin allows the identification and isolation of the transfected cells. The transfected nucleic acid can also be amplified to express large amounts of the encoded (poly)peptide. The DHFR (dihydrofolate reductase) marker is useful to develop cell lines that carry several hundred or even several thousand copies of the gene of interest. Another useful selection marker is the enzyme glutamine synthase (GS) (Murphy et al. 1991, Biochem J. 227:277-279; Bebbington et al. 1992, Bio/Technology 10:169-175). Using these markers, the mammalian cells are grown in selective medium and the cells with the highest resistance are selected. As indicated above, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. For vector modification techniques, see Sambrook and Russel (2001), Molecular Cloning: A Laboratory Manual, 3 Vol. Generally, vectors can contain one or more origins of replication (ori) and inheritance systems for cloning or expression, one or more markers for selection in the host, e.g., antibiotic resistance, and one or more expression cassettes. Suitable origins of replication (ori) include, for example, the Col E1, the SV40 viral and the M 13 origins of replication.

The sequences to be inserted into the vector can e.g. be synthesized by standard methods, or isolated from natural sources. Ligation of the coding sequences to transcriptional regulatory elements and/or to other amino acid encoding sequences can be carried out using established methods. Transcriptional regulatory elements (parts of an expression cassette) ensuring expression in prokaryotes or eukaryotic cells are well known to those skilled in the art. These elements comprise regulatory sequences ensuring the initiation of the transcription (e.g., translation initiation codon, promoters, enhancers, and/or insulators), internal ribosomal entry sites (IRES) (Owens, Proc. Natl. Acad. Sci. USA 98 (2001), 1471-1476) and optionally poly-A signals ensuring termination of transcription and stabilization of the transcript. Additional regulatory elements may include transcriptional as well as translational enhancers, and/or naturally-associated or heterologous promoter regions. Preferably, the nucleotide sequence as defined in item (a) of the above preferred embodiment of the invention is operatively linked to such expression control sequences allowing expression in prokaryotic or eukaryotic cells.

The host may be a prokaryotic or eukaryotic cell. A suitable eukaryotic host may be a mammalian cell, an amphibian cell, a fish cell, an insect cell, a fungal cell or a plant cell. Representative examples of bacterial cells are *E. coli, Streptomyces* and *Salmonella typhimurium* cells; of fungal cells are yeast cells; and of insect cells are *Drosophila* S2 and *Spodoptera* Sf9 cells. It is preferred that the cell is a mammalian cell such as a human cell. Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells. The cell may be a part of a cell line, preferably a human cell line. Appropriate culture mediums and conditions for the above-described host cells are known in the art. The host is preferably a host cell and more preferably an isolated host cell. The host is also preferably a non-human host.

In accordance with an even more preferred embodiment of the first aspect of the present invention, a first and a second compound is used, wherein the first compound inhibits the expression and/or the activity of the lncRNA GADLOR 1 and the second compound inhibits the expression and/or the activity of the lncRNA GADLOR 2.

As is evident from the examples herein below, the lncRNAs GADLOR 1 and GADLOR 2 in combination are more potent to induce cardiac remodeling (i.e. in the examples heart failure) as compared to one of these lncRNAs alone. Thus, inhibiting both GADLOR 1 and GADLOR 2 in the treatment or preventing cardiac remodelling is expected to lead to a superior treatment success as compared to inhibiting only one of these lncRNAs. In a second aspect the present invention relates to a method for diagnosing cardiac remodelling in a patient, comprising (a) detecting the expression level of one or both lncRNA(s) selected from GADLOR 1 and GADLOR 2 as defined in connection with the first aspect of the invention in a sample obtained from said patient, and optionally (b) comparing said expression obtained in (a) with the expression level of said lncRNA(s) in a sample obtained from at least one healthy subject or with a predetermined standard that has been obtained from a sample of at least one healthy subject, wherein a greater than 1.5-fold upregulation of the is indicative for cardiac remodelling in the patient.

The above definitions and preferred embodiments as described herein above in connection with the first aspect of the invention apply mutatis mutandis to the second aspect of the invention as far as being applicable to the second aspect of the invention. For instance, also in connection with the second aspect the cardiac remodelling is preferably Heart Failure with preserved Ejection Fraction (HFpEF), Heart Failure with reduced Ejection Fraction (HFrEF), myocardial infarction related cardiac remodelling, a genetic cardiac disease associated cardiac remodelling, cardiac hypertrophy and/or cardiac dysfunction related cardiac remodelling. Among this list of cardiac remodelling conditions Heart Failure with preserved Ejection Fraction (HFpEF), Heart Failure with reduced Ejection Fraction (HFrEF) are more preferred. The cardiac hypertrophy is preferably ventricular hypertrophy, preferably left ventricular hypertrophy, and/or the cardiac dysfunction is preferably ventricular dysfunction, preferably left ventricular dysfunction.

In connection with the second aspect of the invention the expression level of both lncRNAs GADLOR 1 and GADLOR 2 is preferably detected. As is evident from the examples herein below, the lncRNAs GADLOR 1 and GADLOR 2 in combination are more potent to induce cardiac remodeling (i.e. in the examples heart failure) as compared to one of these lncRNAs alone. For this reason the detection of GADLOR 1 and GADLOR 2 is expected to lead to a better diagnosis of cardiac remodelling as compared to the detection of GADLOR 1 or GADLOR 2.

In this connection it is to be understood that the method according to the second aspect of the invention may also encompass detecting and comparing the expression level of lncRNAs being with increased preference at least 80%, at least 85%, at least 90%, at least 92%, at least 94%, at least 96%, at least 98%, at least 99%, and at least 99.5% identical to any one of SEQ ID NOs 1 to 6. The method according to the second aspect of the invention may furthermore encompass detecting and comparing the expression level of one or more lncRNAs differing with increasing preference by no more than 10, such as 5, 4, 3, 2 or 1 nucleotide(s) from any one of SEQ ID NOs 1 to 6. The nucleotide differences may be the addition, deletion and/or substitution of nucleotide(s). The sequences the expression of which is compared, while being homologous, may also differ from each other with increasing preference by no more than 10, such as 5, 4, 3, 2 or 1 nucleotide(s).

The term "sample" designates a tissue sample or a body fluid sample. The body fluid sample is preferably selected from blood, serum, plasma, urine, *salvia*, amniotic fluid, cerebrospinal fluid and lymph. The tissue sample is preferably an organ sample, preferably a heart sample. As far as the method is applied to a body fluid sample it is to be understood that the expression level of the lncRNA GADLOR 1 or GADLOR 2 corresponds to the concentration of the lncRNA GADLOR 1 or GADLOR 2, because lncRNAs are not directly expressed in the body fluid but secreted from the cells, said cells expressing the lncRNAs, into the body fluids.

The "patient" or "subject" referred to herein is preferably human.

The term "detecting the expression level of one or both lncRNA(s) selected from GADLOR 1 and GADLOR 2" means determining the amount or yield of GADLOR 1 or GADLOR 2, and preferably of both GADLOR 1 or GADLOR 2. GADLOR 1 and GADLOR 2 are initially expressed within a cell, in particular in endothelial cells of the heart. It was found in accordance with the present invention that the lncRNAs GADLOR 1 and GADLOR 2 can be detected in the sample of a patient, in particular a heart tissue sample as well as a blood sample. GADLOR 1 or GADLOR 2 being "expressed in a sample" is therefore GADLOR 1 or GADLOR 2 the expression level of which can be detected in the sample by means and methods including those being further detailed herein below. GADLOR 1 or GADLOR 2 is downregulated in a test sample if the amount or yield of the GADLOR 1 or GADLOR 2 is significantly less as compared to the amount or yield of GADLOR 1 or GADLOR 2 in a control sample.

In accordance with the above described diagnostic method the control sample is either a sample obtained from at least one healthy subject or a predetermined standard that has been obtained from a sample of at least one healthy subject. A healthy subject in particular a healthy subject with no heart condition can be routinely identified by a physician. The at least one healthy subject is with increasing preference at least two, at least three, at least five, and at least ten healthy subjects. By employing more than one healthy subject individual GADLOR 1 and GADLOR 2 expression level differences may be balanced. With respect to the use of a predetermined standard it is noted that within the context of the diagnostic method of the invention is not or not always necessary to determine the GADLOR 1 and/or GADLOR 2 expression level in a sample of at least one healthy subject. Once GADLOR 1 and/or GADLOR 2 expression levels obtained from a sample of at least one healthy subject are available they may be used in the diagnostic method of the invention as a predetermined standard.

The expression level in the samples can be quantified by any suitable means and methods available from the art. In general relative and absolute quantification means and methods can be used. In absolute quantification no known standards or controls are needed. The expression level can be directly quantified. As well-known in the art, absolute quantification may rely on a predetermined standard curve. In relative quantification the expression level is quantified relative to a reference (such as known control expressions levels). Also in the absence of controls, one can relatively quantify the expression level when comparing e.g. fluorescence intensities.

Methods to assess RNA concentration may, for example, comprise measuring the fluorescence intensity of dyes that bind to nucleic acids and selectively fluoresce when bound. Such methods comprise a reverse transcription reaction and the production of cDNA, wherein the amount of the cDNA is determined thereby indirectly determining the amount of the RNA. The fluorescent-based method is particularly useful for cases where the RNA concentration is too low to accurately assess some with spectrophotometry and/or in cases where contaminants absorbing at 260 nm make accurate quantification by spectrophotometry difficult or impossible.

When comparing the expression level of a lncRNA between different samples reliability of the comparison is preferably improved by including an invariant endogenous control (expression of a reference gene) to correct for potential sample to sample variations. Such normalization with respect to an invariant endogenous control is routinely performed in the art. For example, means and methods for expression level normalization, e.g. in real-time RT-PCR (see, for example, Bustin, Journal of Molecular Endocrinology, (2002) 29, 23-39) or micro-array expression analysis (see, for example, Calza and Balwitan, Methods Mol Biol. 2010; 673:37-52) are well-established. Also methods for normalization of the expression levels of small RNA sequences are established (see, for example, Mestdagh et al. (2009) Genome Biol.; 10(6):R64). In case RT-PCR or a micro-array is used to determine the expression levels in accordance with the present invention, the expression levels are preferably normalized to a spiked-in RNA (see, for example, McCormick et al. (2011), Silence, 2:2). Known amounts of a spiked-in RNA are mixed with the sample during preparation. More preferably the RNA is externally spiked-in to the sample before the RNA isolation process is carried out. The spiked-in RNA technology is well-known and commercial kits are available from a number of manufacturers. The spiked-in RNA is preferably a spiked-in *C. elegans* RNA.

In the examples herein below the primer pair of SEQ ID NOs 11 and 12 was employed for detecting the expression level of human GADLOR 1, the primer pair of SEQ ID NOs 13 and 14 for human GADLOR 2, the primer pair of SEQ ID NOs 15 and 16 for mouse GADLOR 1 and the primer pair of SEQ ID NOs 17 and 18 for mouse GADLOR 2, wherein the uneven number is the forward primer and the even number is the reverse primer. In addition, the expression level of human GADLOR 1 can be detected by the primer pair of SEQ ID NOs 60 and 61, and the expression level of human GADLOR 2 can be detected by the primer pair of SEQ ID NOs 62 and 63. One or more of these primer pairs is preferably used in the diagnostic method according to the second aspect of the invention. One or more of these primer pairs is likewise preferably incorporated into the kit of the invention being described herein below. As regards the detection of the expression levels of human GADLOR 1 and 2, the primer pair of SEQ ID NOs 60 and 61 and SEQ ID NOs 62 and 63 is particularly preferred, respectively.

The greater than 1.5-fold upregulation is with increasing preference greater than 2-fold upregulation, 2.5-fold upregulation, 3-fold upregulation, and greater than 4-fold upregulation. The higher thresholds for the downregulation may increase the reliability of the method of the second aspect of the invention.

It is shown in the examples that in human heart tissue samples as well as in serum samples from patients with heart failure on average GADLOR1 was 7-fold and GADLOR2 was 4-fold upregulated. Based on this finding it can be expected that the upregulation of GADLOR1 and/or GADLOR2 in sample from a subject is indicative for a subject having cardiac remodelling or being at risk of developing cardiac remodelling.

In accordance with a preferred embodiment of the second aspect of the present invention, the sample is a heart tissue sample or a blood sample.

The blood sample is more preferably a serum sample, because serum was used as blood sample in the examples.

In accordance with a further preferred embodiment of the second aspect of the present invention, the detection of the expression level of the lncRNA comprises (a) quantitative PCR, preferably quantitative real time PCR, or (b) a template/RNA amplification method followed by determining the expression level of the lncRNA using a fluorescence- or luminescence-based quantification method.

In quantitative PCR (qPCR), the amount of amplified product is linked to fluorescence intensity using a fluorescent reporter molecule. The point at which the fluorescent signal is measured in order to calculate the initial template quantity can either be at the end of the reaction (endpoint semi-quantitative PCR) or while the amplification is still progressing (real-time qPCR).

In endpoint semi-quantitative PCR, fluorescence data are collected after the amplification reaction has been completed, usually after 30-40 cycles, and this final fluorescence is used to back-calculate the amount of template present prior to PCR.

The more sensitive and reproducible method of real-time qPCR measures the fluorescence at each cycle as the amplification progresses. This allows quantification of the template to be based on the fluorescence signal during the exponential phase of amplification, before limiting reagents, accumulation of inhibitors, or inactivation of the polymerase have started to have an effect on the efficiency of amplification. Fluorescence readings at these earlier cycles of the reaction will measure the amplified template quantity where the reaction is much more reproducible from sample to sample than at the endpoint.

A non-limiting example of a template/RNA amplification method followed by determining the expression level of the lncRNA(s) GADLOR 1 and/or 2 using a fluorescence- or luminescence-based quantification method is a method combining transcription mediated amplification (TMA) and a hybridization protection assay (HPA). In more detail, such a method may comprise hybridizing one or more oligonucleotides ("capture oligonucleotides") that are complementary to GADLOR 1 and/or 2. The hybridized target sequences are then captured onto magnetic microparticles that are separated from the sample in a magnetic field. Wash steps may be utilized to remove extraneous components. Target amplification typically occurs via TMA, which is a transcription-based nucleic acid amplification method that utilizes two enzymes, Moloney murine leukemia virus (MMLV) reverse transcriptase and T7 RNA polymerase. A unique set of primers is used for GADLOR 1 or GADLOR 2, preferably one or more of the above-described the primer pairs of SEQ ID NOs 11 and 12, SEQ ID NOs 13 and 14, SEQ ID NOs 15 and 16 and SEQ ID NOs 17 and 18. The reverse transcriptase is used to generate a DNA copy (containing a promoter sequence for T7 RNA polymerase) of the target sequence. T7 RNA polymerase produces multiple copies of RNA amplicon from the DNA copy. Detection of GADLOR 1 and/or 2 expression level is achieved by HPA using single-stranded, chemiluminescent-labelled nucleic acid probes that are complementary to the one or more amplicon. Preferably, distinguishably labelled probes are used for each target amplicon. The labelled nucleic acid probes hybridize specifically to the amplicon. A "selection reagent" then differentiates between hybridized and unhybridized probes by inactivating the label on unhybridized probes. During the detection step, the chemiluminescent signal produced by the hybridized probe is measured in a luminometer and is reported as "Relative Light Units" (RLU), thereby quantifying the GADLOR 1 and/or 2 expression level.

In accordance with a further preferred embodiment of the second aspect of the invention the method comprises prior to the detection of the expression level of GADLOR 1 and/or 2 a pre-amplification step of the RNA within the test patient's sample and/or the healthy patient's sample.

Performing a pre-amplification step is of particular advantage in case only a low amount of (test and/or control) sample is available. The pre-amplification step allows increasing the amount of RNA within the sample before proceeding to the analysis of the expression level. Means and methods for the pre-amplification of RNA are well known in the art (see, e.g., Vermeulen et al (2009) BMC Res Notes., 2:235). In case both the RNA in the test and control sample is pre-amplified preferably the same method for the pre-amplification step is used such that the relative amount of RNA of the test sample as compared to the control sample is maintained. In case only the RNA of the test or control sample is pre-amplified or the two RNA samples are pre-amplified by different methods, the expression level data may have to be normalized for the pre-amplification step; see, e.g. Mestdagh et al. (2009), Genome Biology 2009, 10:R64.

In a third aspect the present invention relates to a kit for diagnosing cardiac remodelling in a patient, said kit comprising means for the detection of the expression level of one or both lncRNA(s) selected from GADLOR 1 and GADLOR 2 as defined in connection with the first aspect of the invention, and instructions how to use the kit.

The above definitions and preferred embodiments as described herein above in connection with the first and second aspect of the invention apply mutatis mutandis to the third aspect of the invention as far as being applicable to the second aspect of the invention. For instance, also in connection with the third aspect the cardiac remodelling is preferably Heart Failure with preserved Ejection Fraction (HFpEF), Heart Failure with reduced Ejection Fraction (HFrEF), myocardial infarction related cardiac remodelling, a genetic cardiac disease associated cardiac remodelling, cardiac hypertrophy and/or cardiac dysfunction related cardiac remodelling. Among this list of cardiac remodelling conditions Heart Failure with preserved Ejection Fraction (HFpEF), Heart Failure with reduced Ejection Fraction (HFrEF) are more preferred. The cardiac hypertrophy is preferably ventricular hypertrophy, preferably left ventricular hypertrophy, and/or the cardiac dysfunction is preferably ventricular dysfunction, preferably left ventricular dysfunction.

The instructions how to use the kit preferably inform inter alia that a high expression level of the lncRNA GADLOR 1 and/or GADLOR 2 is indicative for cardiac remodelling.

The means for the detection of the expression level of GADLOR 1 and/or GADLOR 2 are preferably the means required for (i) a quantitative PCR, preferably quantitative real time PCR, or (ii) a template/RNA amplification method followed by determining the expression level of GADLOR 1 and/or GADLOR 2 using a fluorescence- or luminescence-based quantification method. These means have been further detailed herein above in connection with the second aspect of the invention, and may be comprised in the kit. Hence, the means preferably comprise oligonucleotides, such as fluorescent hybridization probes or primers, which specifically hybridize to GADLOR 1 and/or GADLOR 2. Additional ingredients of the kits may be fluorescent or luminescent dyes, preferably coupled to said oligonucleotides. Also, additional ingredients of the kits may be enzymes, such as a reverse transcriptase and/or a polymerase.

Also in connection with the third aspect of the invention, GADLOR 1 and 2 preferably comprises or consists of a nucleic acid sequence selected from the group consisting of SEQ ID NOs 1 to 6. In this connection it is to be understood that the kits may also encompass means for detecting lncRNAs being with increased preference at least 80%, at least 85%, at least 90%, at least 92%, at least 94%, at least 96%, at least 98%, at least 99%, and at least 99.5% identical to any one of SEQ ID NOs 1 to 6. The kit may furthermore encompass means for detecting and comparing the expression level of one or more lncRNAs differing with increasing preference by no more than 10, such as 5, 4, 3, 2 or 1 nucleotide(s) from any one of SEQ ID NOs 1 to 6. The nucleotide differences may be the addition, deletion and/or substitution of nucleotide(s).

The various components of the kit may be packaged in one or more containers such as one or more vials. The vials may, in addition to the components, comprise preservatives or buffers for storage.

In accordance with a preferred embodiment of the third aspect of the invention, the means are primer pairs used for the specific detection of the lncRNA(s) selected from GADLOR 1 and GADLOR 2.

The primer pairs of SEQ ID NOs 11 and 12, SEQ ID NOs 13 and 14, SEQ ID NOs 15 and 16, and SEQ ID NOs 17 and 18 are described herein above in connection with the method according to the second aspect of the present invention. One or more of these primer pairs is preferably incorporated into the kit of the invention as means for the detection of the expression level of GADLOR 1 and/or 2.

In a fourth aspect the present invention relates to a method for producing a non-human animal model for heart failure comprising (a) the administration of the lncRNA of GADLOR 1 and/or GADLOR 2 as defined in connection with the first aspect of the invention to the myocardium of the animal; and (b) the induction of pressure overload in the myocardium of the animal.

The non-human animal is preferably a mammal. Non-limiting examples are mouse, rat, swine and monkey. The non-human animal is most preferably a mouse.

The step of the administration of the lncRNA of GADLOR 1 and/or GADLOR 2 as defined in connection with the first aspect of the invention to the myocardium of the animal may also encompass the production of a transgenic animal model, wherein GADLOR 1 and/or GADLOR 2 is/are expressed in the myocardium of the animal. Considerable progress has been made in methods for production of transgenic animal models; beginning with pronuclear microinjection over 20 years ago. Today various methods, including the use of viral vectors, sperm-mediated gene transfer and somatic cell cloning, are available that have overcome many of the limitations of pronuclear microinjection. It is possible to not only readily make simple insertional genetic modifications, but also to accomplish, more complex, homozygous gene targeting and artificial chromosome transfer in animals. Exemplary methods for producing transgenic mice that are widely used are transforming embryonic stem cells (ES cells) growing in tissue culture with a desired DNA; injecting the desired gene into the pronucleus of a fertilized mouse egg.

The examples herein below show that the administration of the lncRNA of GADLOR 1 and/or GADLOR 2 induces heart failure in TAC mice. The example also illustrate that a pressure overload in the myocardium of an animal can be induced, for example, by transverse aortic constriction (TAC).

In a fifth aspect the present invention relates to a non-human animal model for heart failure that has been produced by the method of the fourth aspect the present invention.

Also this animal is preferably a mammal and is most preferably a mouse.

In a sixth aspect the present invention relates to the lncRNA of GADLOR 1 or GADLOR 2 as defined herein in connection with the first aspect of the invention.

The lncRNAs of GADLOR 1 and GADLOR 2 are preferably the human GADLOR 1 or GADLOR 2 orthologs of SEQ ID NOs 1 and 4.

Regarding the embodiments characterized in this specification, in particular in the claims, it is intended that each embodiment mentioned in a dependent claim is combined with each embodiment of each claim (independent or dependent) said dependent claim depends from. For example, in case of an independent claim 1 reciting 3 alternatives A, B and C, a dependent claim 2 reciting 3 alternatives D, E and F and a claim 3 depending from claims 1 and 2 and reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Similarly, and also in those cases where independent and/or dependent claims do not recite alternatives, it is understood that if dependent claims refer back to a majority of preceding claims, any combination of subject-matter covered thereby is considered to be explicitly disclosed. For example, in case of an independent claim 1, a dependent claim 2 referring back to claim 1, and a dependent claim 3 referring back to both claims 2 and 1, it follows that the combination of the subject-matter of claims 3 and 1 is clearly and unambiguously disclosed as is the combination of the subject-matter of claims 3, 2 and 1. In case a further dependent claim 4 is present which refers to any one of claims 1 to 3, it follows that the combination of the subject-matter of claims 4 and 1, of claims 4, 2 and 1, of claims 4, 3 and 1, as well as of claims 4, 3, 2 and 1 is clearly and unambiguously disclosed.

The figures show.

FIG. 1: GATA2 is downregulated in endothelial cells upon mechanical stress. *a*, Immunoblot and quantification (*b*) for GATA2 from control and failing hearts of patients undergoing left ventricular assist device (LVAD) implantation. Ponceau staining was the loading control. Luciferase assay from primary cardiac endothelial cells (sc) and C166 endothelial cells (ECs) (*d*) infected with Ad.GATA-Luc and subjected to mechanical stretch or not (static) for 24 h. *e*, Immunoblot for GATA2 and quantification (*f*) of primary cardiac ECs treated for 24 h as indicated. Data are mean±sem; the number of biological replicates is shown in bars; *p<0.05, *** p<0.001.

FIG. 2: Endothelial GATA2 knock-out mice (G2-EC-KO) develop heart failure during pressure overload (TAC). *a*, qPCR of GATA2 mRNA in cardiac endothelial cells (EC) from indicated mice. *b*, Heart weight/body weight (HW/BW), lung weight/BW ratio and (*c*) left ventricular ejection fraction (EF) 2 weeks after sham or TAC surgery. *d*, Capillaries/cardiomyocyte ratio and (*e*) representative immunofluorescence pictures (scale bar, 20 μm). *f*, qPCR of GATA2 mRNA in cardiac ECs. *g*, Kaplan-Meier survival curves after TAC (n=37 control and n=16 VE-Cad-G2-EC-KO). *h*, EF of mice 4 weeks after TAC. *i*, Capillaries/cardiomyocyte ratio. *j*, Scheme of experiments in *k* and *l*. *k*, qPCR of GATA2 mRNA in GATA2$^{flox/flox}$ ECs treated as indicated. *l*, Size of cardiomyocyte (CMs) grown on ECs. Representative immunofluorescence pictures (scale bar, 50 μm). Data are mean±sem; the number of biological replicates is shown in the graphs; *p<0.05, p<0.01, * p<0.001, **** p<0.0001.

FIG. 3: The lncRNAs GADLOR1 and 2 are suppressed by GATA2. *a*, Volcano plot of RNA expression from microarray of cardiac endothelial cells (EC) from indicated mice. Red dots indicate upregulated, green downregulated and blue unregulated RNAs in G2-EC-KO ECs. *b-c*, qPCR for GADLOR1 and 2 in mouse cardiac ECs. *d-e*, qPCR of GADLOR1 and 2 in cardiac ECs and whole hearts. *f*, UCSC Genome Browser view of mouse chromosome 16, encoding GADLOR1 (AK037972) and 2 (AK038629). *g-h*, Scheme of promoters of GADLOR1 and 2; potential GATA binding sites and primers for ChIP are shown. Below, left: Anti-myc ChIP for binding of myc-GATA2 to promoter regions of GADLOR1 (*g*) and 2 (*h*). Below, right: Luciferase activity after co-transfection with pGADLOR1-Luc (*g*) or pGADLOR2-Luc (*h*) and GATA2 or control plasmid. *i*, qPCR of GADLOR1 and 2 in cardiac tissue from failing hearts and serum of patients with heart failure due to aortic stenosis. Data are mean±sem; the number of biological replicates is shown in graphs; *p<0.05 p<0.01, * p<0.001, **** p<0.0001.

FIG. 4: Regulation of cardiomyocyte signalling by endothelial GADLOR1 and 2. *a*, Immunoblots for indicated proteins of cardiac protein lysate 2 weeks after surgery. *b*, Immunofluorescence of cardiac sections. *c*, qPCR for RCAN1.4 mRNA from mouse hearts. (*d*) Experimental scheme (above) and qPCR (below) of GADLOR1 and 2 in isolated GATA2$^{flox/flox}$ endothelial cells (ECs) treated with Ad.Cre or Ad.Control and in cardiomyocytes (CM) treated with exosomes from supernatants of these ECs. *e*, Experimental scheme (above) and qPCR results (below) from CMs treated with exosomes from supernatants of C-166 ECs over-expressing GADLOR1 or 2 for 72 h. CM immunofluorescence (right) after treatment with PKH67 labeled EC exosomes (scale bar, 20 μm). *f*, Immunoblots of indicated proteins from CMs treated as shown. *g*, Luciferase activity from CMs infected with Ad.NFAT-Luc, treated with PE and exosomes. Data are mean±sem; the number of biological replicates is shown in the graphs; *p<0.05, p<0.01, * p<0.001, **** p<0.0001.

FIG. 5: GADLORs interact with the Ras-like protein TC21. *a*, Scheme of the GADLOR co-precipitation assay. *b*, Proteins bound to GADLOR2, determined by mass spectrometry. *c*, Quantification of TC21/GADLOR co-immunoprecipitation (RIP assay) after IP with IgG or anti-myc from HEK293 cells transfected with TC21-myc and GADLOR1+2. *d*, Immunoblot of indicated proteins with quantification (*e-f*) from HEK293 cells transfected with active TC21 (TC21-V23) and treated with exosomes as shown. *g*, IP with anti-myc or IgG from HEK293 cells transfected with TC21-myc and treated with exosomes as indicated, and immunoblotting (IB) as demonstrated with quantification in (*h*). Data are mean±sem; the number of biological replicates is indicated within the graphs; *p<0.05, p<0.01, ** p<0.0001.

FIG. 6: GADLORs trigger cardiomyopathy. *a*, Experimental scheme. *b*, qPCR of GADLOR1 and 2 from hearts 1 week after TAC and application of control or GADLOR exosomes. *c-d*, Echocardiographic ejection fraction (EF), wall thickness and left ventricular end-diastolic area (LVEDA) 1 and 2 weeks after surgery. *e*, qPCR of cardiac BNP and RCAN1.4 mRNA of mice treated like in (*b*). *f*, Immunoblots for indicated proteins from whole hearts and quantification (*g*). *h*, Experimental scheme of the GapmeR experiment. *i*, Heart weight/body weight (HW/BW), lung weight/BW ratio and (*j*) EF in mice treated with GAD- LOR1+2-specific or control GapmeR after TAC surgery. *k*, Immunoblot from mouse hearts and quantification (*l*). Data are mean±sem; the number of biological replicates is indicated within the graphs; *p<0.05, **p<0.01.

FIG. 7: Further characterization of endothelial GATA2 knock-out mice (G2-EC-KO). *a*, G2-EC-KO and control mice were subjected to transverse aortic constriction (TAC) for 2 weeks. Left ventricular end-diastolic area (LVEDA) and heart rate (*b*) were determined during echocardiography. *c-g*, qPCR analysis of ANP, BNP, α-MHC, β-MHC and SERCA2a mRNA expression from mouse hearts. *h*, Sirius-red staining (scale bar, 100 μm) of heart tissue slides and quantification of cardiomyocytes cross-sectional area (*i*) of the indicated mice two weeks after TAC. *j-l*, G2-EC-KO (VE-Cad) and control mice were subjected to TAC or sham surgery for 4 weeks. LVEDA (*j*) and heart rate (*k*) were determined. *l*, Sirius-red staining of heart sections (scale bar, 100 μm). Data are mean±sem; the number of biological replicates is indicated within graphs; *p<0.05, **p<0.01.

FIG. 8: GADLOR expression in wild-type mice. *a*, Tissue expression pattern of GADLOR1 and 2 of various mouse organs. The relative expression as determined in a qPCR run is demonstrated. *b*, GADLOR expression in cardiac endothelial cells in response to sham or 1 or 8 weeks of TAC. Data are mean±sem; the number of biological replicates is indicated within the graphs; *p<0.05, **p<0.01.

FIG. 9: Short open reading frames in the GADLORs. Analysis of possible open reading frames (ORF) of GADLOR1 and GADLOR2; bp denotes base pairs, aa denotes amino acids.

FIG. 10: Signal transduction in GATA2 mutant mice and during GADLOR exposure. *a-d*, Quantification of the immunoblots shown in the FIGS. 4*a* and 4*f* (*e-l*). *m*, Immunoblot of the indicated proteins from cardiomyocytes stimulated with phenylephrine (PE, 100 μM) for 15 min and treated with exosomes containing either GADLOR1 or 2. Data are mean±sem; the number of biological replicates is indicated within graphs; *p<0.05, p<0.01, *p<0.001.

Figure 11:
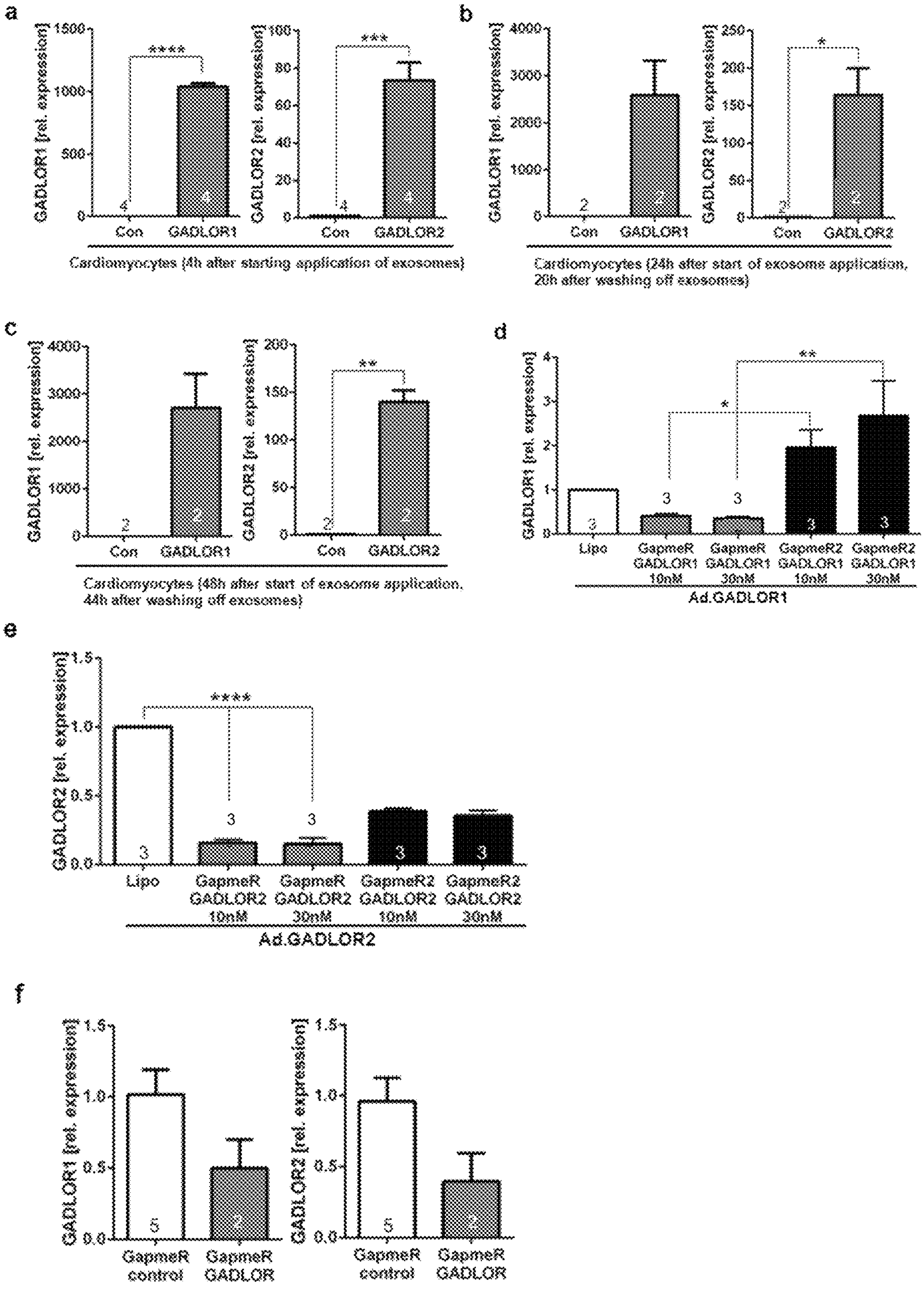

FIG. 11: Endothelial GADLORs transfer to cardiomyocytes and manipulation of GADLOR expression by specific GapmeRs. *a-c*, qPCR analysis of the GADLOR1 and 2 expression in cardiomyocytes treated with exosomes purified from supernatants of C-166 endothelial cells overexpressing GADLOR1 or 2. *d-e*, qPCR analysis of GADLOR1 or 2 expression in COS cells overexpressing GADLOR1 or 2 after transfection with different concentration of GapmeR or GapmeR2 as indicated. GapmeR against GADLOR1 and GapmeR against GADLOR2 were used in combination for the experiment shown in FIG. 6*h*. GapmeR2 were not used. *f*, qPCR of GADLOR1 or 2 in endothelial cells isolated from the hearts of G2-EC-KO, VE-Cad mice treated with control GapmeR or GADLOR1/2-specific GapmeRs. Data are mean±sem; the number of biological replicates is indicated within the graphs; *p<0.05, p<0.01, *p<0.001, ****p<0.0001

Figure 12:
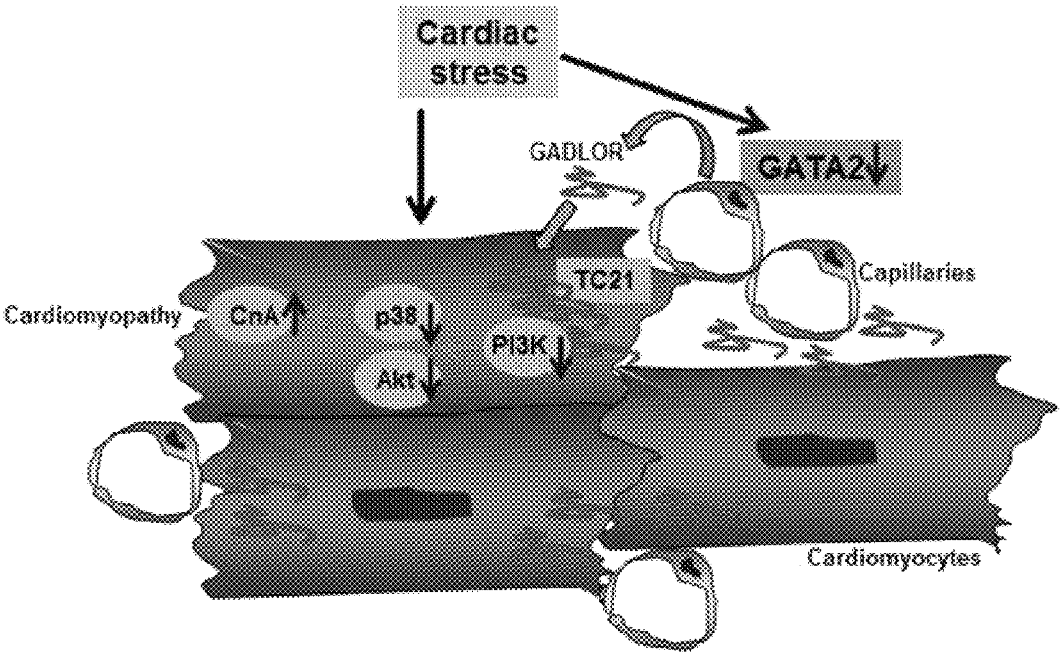

FIG. 12: Schematic representation of this study's findings. Chronic cardiac overload (stress) reduces GATA2 in endothelial cells. This leads to de-repression of the lncRNAs GADLOR1 and 2, which are secreted and taken up by cardiomyocytes, where they disturb the interaction between TC21 and PI3K ultimately resulting in reduced p38 and Akt, increased calcineurin activation and cardiomyopathy.

The Examples illustrate the invention.

EXAMPLE 1—MATERIAL AND METHODS

Animals

Tamoxifen-inducible endothelial cell specific GATA2 knock-out mice were generated by crossing GATA2$^{flox/flox}$ mice with Tie2ER$^{T2}$Cre (in here: Tie2-CreER) transgenic mice or Cdh5(PAC)-CreERT2 (in here: VE-Cadherin-CreER) mice[48,25,49]. GATA2$^{flox/flox}$ and wild-type mice with and without Cre were used as controls. GATA2$^{flox/flox}$ x Tie2-CreER (G2-EC-KO) and control animals received tamoxifen (Sigma-Aldrich) in their diet (400 mg/kg food pellets for 6 weeks, i.e. 40 mg/kg body weight/day). GATA2$^{flox/flox}$ VE-Cadherin-CreER (G2-EC-KO, VE-Cad) and controls were injected intraperitoneally with a dose of 0.5 mg/mouse/day of tamoxifen for 5 consecutive days. Administration of tamoxifen was started at the age of 5-6 weeks. Further details on mouse strains is shown in Table 1. Constriction of the transverse aortic arch (TAC) was performed in 8- to 12 week old mice around a 27-gauge needle as previously described[50]. Echocardiography was performed with a linear 30 MHz transducer (Vevo770, Visualsonics) in mice that were sedated with 1-1.5% isoflurane and placed on a heating pad to maintain body temperature. LV end-diastolic area (LVEDA), end-diastolic average wall thickness (Wth) and enddiastolic volume (EDV) as well as end-systolic area (LVESA) and endsystolic volume (ESV) were recorded or calculated from the short axis view. Ejection fraction was calculated as [(EDV−ESV)/EDV]×100. For the assessment of mouse survival after TAC, mice were followed and inspected daily for 15 days. No mortality was observed in sham operated mice. Mice that died before the end of the planned experimental period were excluded from the analysis.

At the end of the experiments, mice were weighed and then euthanized. Hearts and lungs were quickly removed from the thoracic cavity. After removal of blood, the heart and lung weights were determined. All procedures involving the use and care of animals were performed according to the Guide for the Care and Use of Laboratory Animals published by the National Research Council (NIH Publication No. 85-23, revised 1996) and the German animal protection code. All animal procedures were approved by our local state authorities (the Lower Saxony State Office for Consumer Protection and Food Safety, Germany 33.9-42502-12-10/0016 and 33.19-42502-04-14/1403).

LNA GapmeR control (40 mg/kg/body weight; Exiqon) or LNA GapmeR GADLOR1&2 (40 mg/kg/body weight for each; Exiqon) were injected intraperitoneally twice per week starting 24 h after surgery (FIG. 6*h*).

Human Tissue and Serum Samples

Studies on human heart tissue were permitted by the Massachusetts General Hospital Institutional Review Board (US), and by the Ethical Committee of the Hannover Medical School, Germany (Az. Z 14.06-A 1871-30724/98). The human heart samples used in this study were in part described previously and obtained after death, explantation or left ventricular assist device (LVAD) implantation[51]. Control human heart tissue was derived from victims of motor vehicle accidents, gunshot wounds or from healthy heart organ donors, when the organ was ineligible for transplantation. Failing human heart samples were derived from patients with end-stage heart failure undergoing cardiac transplantation. Transmural left-ventricular samples of the cardiac apex were obtained during implantation of an LVAD (Table 2).

Human serum samples were collected from the patients with known aortic stenosis before replacement of the aortic valve or from healthy blood donors (Table 3). This study was approved by the Ethical Committee of the Hannover Medical School, Germany. All individuals and patients gave written informed consent.

Cell Culture

Primary juvenile cardiac endothelial cells were isolated from the hearts of 7-11 days old mice as previously described by Lim and Luscinskas[52]. In short, the mouse hearts were digested by collagenase type 1 (Worthington) with subsequent purification of endothelial cells by Dynabeads (Invitrogen) coated with CD31 antibody (BD Pharmingen). The cells were plated on gelatine coated cell culture plates. After growing to confluency, the cells were purified again with Dynabeads coated with CD102 (BD Biosciences) antibodies and plated on gelatine coated cell culture plates for experiments.

Adult heart endothelial cells were isolated from the hearts of adult mice using CD146 coated micro beads with MACS technology from Miltenyi. The primary isolated ECs were about 85% pure as determined by FACS analysis after staining for CD31. The isolated cells were directly used for RNA extraction.

Neonatal rat ventricular cardiomyocytes (NRCMs) were isolated from 1-3 day old Sprague-Dawley rats by Percoll density gradient centrifugation as previously described 53. On the day after isolation, the cells were switched to serum free media.

HEK293 cell line (Cell Line 293 ACC: 305, DSZM), NIH3T3 (ATCC), COS-1 and C166 mouse embryonic yolk sac endothelial cells (C-166, ATCC) were cultured in DMEM containing 10% FCS.

Plasmids and Adenoviruses

To generate the luciferase reporter plasmids harboring the putative GADLOR1 and 2 promoter DNA, the sequences 3365 bp upstream of GADLOR1 and 3581 bp upstream of GADLOR2 (FIGS. 3*g* and *h*) were separately cloned into the pGL2 basic vector (Promega) to generate pGADLOR1-Luc and pGADLOR2-Luc. The TC21-expressing plasmid was generated by cloning TC21 cDNA amplified by PCR from the RRAS2 plasmid (#38816, Addgene) with insertion of a C-terminal myc-tag sequence into the pShuttleCMV vector (Agilent Technologies) to generate pshuttleCMV-TC21-myc. The myc-tagged TC21-V23 expressing construct was kindly provided by Christopher J. Marshall[21]. All transfections were performed using Lipofectamine 2000 reagent (Invitrogen).

Ad.βgal (Ad.Control), Ad.Cre, Ad.GATA-luc and Ad.NFAT-luc were previously described[50,27,54]. To generate GADLOR-expressing recombinant adenoviruses (Ad.GADLOR1 and 2), the mouse cDNAs of AK037972 (GADLOR1) and AK038629 (GADLOR2, both from Source BioScience) were subcloned into the pShuttleCMV vector and adenoviruses were generated using the AdEasy Adenoviral Vector System (Agilent Technologies). For GATA2 overexpression, human GATA2 cDNA (BC006793, Open Biosystems) was subcloned into the pShuttleCMV vector, a myc-tag was introduced at the N-terminus (pshuttleCMV-GATA2-myc), and an adenovirus was generated.

Adenoviral infection of cultured cells was conducted at 37° C. for 2 hours. Subsequently, the cells were washed three times with PBS before cell culture media was applied.

Co-Culture of Endothelial Cells and Cardiomyocytes

Adenoviruses encoding for either 3-galactosidase (Ad.Control) or Cre-recombinase (Ad.Cre) were added to primary juvenile endothelial-cells for two hours on the day after purification with CD102 antibodies. For co-culture, neonatal rat cardiomyocytes were plated on top of the endothelial cells 24 hours later and stimulation with phenylephrine (PE, 100 μM) was subsequently conducted. Cell size was determined by planimetry after immunofluorescence staining for α-actinin (Sigma-Aldrich).

Exosome Extraction

The exosomes were isolated from supernatants of C-166 cells 72 hours after infection (or other time points as indicated) with Ad.GADLOR1 and/or Ad.GADLOR2 or from primary juvenile endothelial cells 5 days after infection with Ad.Control or Ad.Cre, using the ExoQuick-TC™ exosome precipitation solution (SBI System Biosciences) according to the manufacturer's instructions. Exosome pellets were resuspended in growth medium and applied to the cells. As control, exosomes isolated from the supernatants of C-166 or juvenile endothelial cells infected with Ad.Control were used.

For application in vivo, exosomes were injected together with 0.5 μg sodium nitroprusside (Sigma-Aldrich) into the left ventricular cavity with simultaneous cross-clamping of the aorta and pulmonary artery in 0.9% sodium chloride solution (total volume, 100 μl/injection) as described previously for cardiac adenoviral delivery[3]. TAC surgery was performed immediately after exosome administration. Exosomes were labeled with the green fluorescent dye PKH67 (Sigma-Aldrich) according to the manufacturer's instructions. Exosomes pellets were resuspended in diluted PKH67. After washing with PBS, exosomes were pelleted by centrifugation, resuspended in cell culture medium and added to the cardiomyocytes. After 24 hours of incubation, cells were washed, fixed with 4% paraformaldehyde and analyzed.

Stretch Assay

To produce cyclic stretch in vitro, a computerized Flexcell strain unit (FX-5000T, Flexcell International) was employed. Cells were seeded on a Bioflex culture plate on type I collagen substrate (Dunn Labortechnik). 24 hours after infection with Ad.GATA-Luc, cells were subjected to a 15% radial stretch (1 Hz) for 24 hours. Controls consisted of cells seeded on the Bioflex culture plate, without cyclic stretch.

Luciferase Assay

NIH3T3 cells were transiently transfected with pGADLOR1/2-Luc constructs and co-transfected with pshuttleCMV-GATA2-myc or empty plasmid.

NRCM were infected with Ad.NFAT-luc. Primary juvenile endothelial cells were infected with Ad.GATA-Luc and subjected to stretch. All cells were harvested 48 hours after transfection/infection using Passive Lysis Buffer (Promega) and luciferase activity was measured. Values were normalized to total protein as described previously[50].

RNA Isolation and Real-Time PCR

RNA from cultured cardiomyocytes, mouse hearts or human hearts was isolated with the Trifast reagent (Peqlab). For RNA isolation from endothelial cells and human serum samples, the NucleoSpin RNA II kit (Macherey Nagel) and RNeasy mini kit (Qiagen), respectively, were used according to the manufacturer's protocol.

cDNA was generated from RNA with the Maxima H Minus First Strand cDNA Synthesis Kit (Thermo Scientific) using standard procedures. Quantitative PCR was performed using the Maxima SYBR Green qPCR Master Mix (Thermo Scientific) following the kit directions with the MX4000 multiplex QPCR system from Stratagene. Gene expression was normalized to Gapdh mRNA expression. The value of control samples was set to 1. Tissue expression analysis of GADLORS was performed using mouse normal tissue qPCR panel I (TissueScan qPCR array, OriGene Technologies) with GADLOR1 or 2 specific primers following the manufacturer's protocol. The qPCR primers are listed in Table 1.

Agilent Micro-array

For gene expression profiling, the Mouse Gene Expression kit from Agilent was used. 200 ng of total RNA was transcribed into cDNA, amplified using T7 RNA polymerase while incorporating cyanine 3-labeled CTP and then hybridized according to the manufacturer's protocol (Quick Amp, Agilent). Signal intensities were extracted from scan images using Feature Extraction Software v10.7.3.1. The raw data has been deposited in the GEO expression database (http://www.ncbi.nlm.nih.gov/geo/) under the accession number GSE93596. Raw data were further analysed using R package "Limma". Raw data were log 2 transformed and quantile normalized. For testing differential gene expression, normalized data sets were filtered for informative genes (showing at least expression values >log 2(15) in more than two samples). Datasets were tested across all groups (ANOVA) or pairwise using linear models to assess differential expression in the context of the multifactorial designed experiment. For statistical analysis and assessing differential expression, Limma used an empirical Bayes method to moderate the standard errors of the estimated log-fold changes.

Immunoprecipitation and Immunoblot Analysis

The cells were harvested in lysis buffer containing 10 mM Hepes, 100 mM KCl, 5 mM $MgCl_2$ and 0.5% NP-40. Immunoprecipitation was conducted with 4 μg anti-myc antibody/sample (Cell Signalling). The immuno-complexes were captured with Protein A/G PLUS Agarose beads (Santa Cruz), and after washing, the proteins were resolved with SDS-PAGE electrophoresis and subjected to immunoblotting.

Immunoblotting was performed using standard procedures with antibodies to the following proteins: phospho-Akt, total-Akt, phospho-p38 MAPK, total-p38 MAPK, phospho-ERK1/2, ERK 1/2, phospho-SAPK-JNK, total-SAPK-JNK, myc-tag (all from Cell Signaling Technology), GATA2 (Abcam), PI3 Kinase p85 (Millipore), TC21/R-Ras2 (R&D) and actin (Sigma-Aldrich). Further details on the antibodies used in this study are available in Table 1. Densitometry of protein bands was performed using QuantityOne (Bio-Rad) software.

lncRNA Pulldown

The sequence of GADLOR2 was amplified by PCR using a forward primer carrying a T7 polymerase promoter sequence at the 5' end. Approximately 2 μg of purified PCR product (PCR purification kit, Thermo Scientific) was transcribed in vitro with incorporation of biotin with a Biotin RNA Labeling Mix (Roche) and T7 RNA polymerase (Roche). Cell lysates from isolated cardiomyocytes were incubated with the labeled RNA overnight at 4° C. 60 μl of washed streptavidin agarose beads (Millipore) were added to each binding reaction and multiple washing steps were performed. The associated proteins were eluted from the beads, resolved by SDS-PAGE, and whole gel lanes were excised and analyzed by mass spectrometry.

ChIP Assay

The chromatin-immunoprecipitation (ChIP) assay was performed according to manufacturer's directions (ChIP Assay kit, Millipore) on the cells overexpressing myc-tagged-GATA2 protein. Myc-tag antibodies (Cell Signaling) and normal mouse IgG (Santa Cruz) were used for immunoprecipitation. Sequences of the primer used to amplify regions of GADLOR promoter are listed in Table 1.

RIP Assay

RNA-protein complex immunoprecipitation (FIG. 5*c*) was performed from HEK293 cells transfected with pshuttleCMV-TC21-myc and with pshuttleCMV-GADLOR1 and 2, using anti-myc (Cell Signaling) or normal goat IgG (Santa Cruz) with Magna RIP™ RNA-Binding Protein Immunoprecipitation Kit (Millipore) according to manufacturer's directions. Co-precipitated RNA was extracted by Trifast reagent (Peqlab) according to the manufacturer's protocol and subjected to qRT-PCR analysis to detect each GADLOR. Primer sequences are shown in Table 1.

Histological Analysis

Cryosections (7 μm in thickness) were stained with TRITC-conjugated wheat germ agglutinin (WGA, Sigma-Aldrich) to outline cardiomyocytes and with Isolectin B4 (Vector Laboratories) to visualize endothelial cells and capillaries. Fibrosis was detected with the Sirius Red staining method.

Immunofluorescence staining was performed using standard procedures. Antibodies used for immunofluorescence staining (see also Table 1): phospho-p38 MAPK, phospho-Akt (both from Cell Signaling Technology), α-actinin (Sigma-Aldrich) followed by Anti-Rabbit/Mouse IgG Alexa Fluor® 488 or Anti-Rabbit/Mouse IgG Alexa Fluor® 555 secondary antibody (NEB). Nuclear staining was performed with Mounting Medium (Roth) with DAPI.

Statistical Analysis

All values are presented as means±sem. Sample size was chosen as a result of previous experience regarding data variability in similar models and experimental set-up. No statistical method was used to predetermine sample size. All experiments were carried out in at least 3 biological replicates. The number of biological replicates (number of mice, samples or cell culture dishes) is demonstrated in the Figures. Randomization was not used in this study. The investigators were blinded for mouse genotype and treatment during surgeries, echocardiography, organ weight determination and all histological and immunofluorescence quantifications. The variance was comparable between groups and normality was assumed, when possible. Adequate tests were chosen to assess statistical significance. Multiple groups were compared by one-way repeated measures analysis of variance (ANOVA) followed by the Sidak's multiple comparisons test or by Student's t-test when comparing two experimental groups. Mouse mortality after TAC surgery was analyzed by the log-rank test. A two-tailed P value of less than 0.05 was considered significant. All statistics were calculated with the Graph Pad Prism 6 software.

Data Availability

The micro-array data that support the findings of this study have been deposited in the Gene Expression Omnibus (GEO) repository with the accession code GSE93596. The data can be accessed using the following link: https://www.ncbi.nlm.nih.gov/geo/query/acc.cgi?token=wvsnakcalpkpxyl&acc=GSE93596

EXAMPLE 2—REDUCED ENDOTHELIAL GATA ACTIVATION UPON STRETCH

In the heart, GATA2 is expressed in ECs, but not in cardiomyocytes or fibroblasts[18]. A strong downregulation of GATA2 protein in myocardial specimens from patients with advanced systolic heart failure compared to control myocardium was found (FIG. 1*a*-*b*, Table 2). It was hypothesized that the increased cardiac mechanical overload in heart failure might trigger the GATA2 dysregulation. To directly measure GATA activation in response to mechanical overload, primary cardiac mouse ECs and C166 ECs were transduced with a GATA dependent luciferase reporter adenovirus and subsequently applied cyclic stretch. This mechanical loading significantly reduced GATA dependent transcriptional activity in both endothelial cell types (FIG. 1c-d). Immunoblotting revealed a concomitant decrease in GATA2 protein levels in stretched versus static ECs (FIG. 1e-f).

EXAMPLE 3—ENDOTHELIAL GATA2 KNOCK-OUT TRIGGERS HEART FAILURE

To assess the functional consequences of reduced endothelial GATA2 abundance during cardiac overload, endothelial GATA2 knock-out mice (G2-EC-KO) were generated by breeding mice harbouring a LoxP targeted GATA2 allele with endothelial Cre expressing Tie2-CreER mice ($GATA2^{flox/flox}$ x Tie2-CreER, FIG. 2a). DNA recombination in ECs was achieved by administration of tamoxifen containing chow for 6 weeks starting at the age of 6 weeks. Littermate $GATA2^{flox/flox}$ and wild-type (WT) mice with and without Tie2-CreER fed with tamoxifen were used as control. Real-time PCR (qPCR) from isolated heart ECs revealed a (by 50-60%) reduced Gata2 mRNA abundance in G2-EC-KO mice (FIG. 2a). To mimic pathological hemodynamic overload, experimental transverse aortic constriction (TAC) was performed in G2-EC-KO and control mice. Two weeks after TAC, G2-EC-KO mice exerted an increased heart weight/body weight (HW/BVV) and lung weight/body weight ratio versus control mice as sign of enhanced cardiac growth and pulmonary congestion (FIG. 2b). Echocardiography revealed a significantly reduced ejection fraction as indicator of systolic heart failure in G2-EC-KO mice after TAC, but no changes were observed in cardiac diastolic dimensions or heart rate (FIG. 2c, FIG. 7a-b). The expression of foetal genes and the cardiomyocyte cross-sectional area were enhanced in G2-EC-KO mice after TAC (FIG. 7c-g, i). No differences were noted between both groups of mice after sham surgery. Assessment of capillary density in the myocardium revealed no changes between control or G2-EC-KO mice after TAC or sham surgery (FIG. 2d-e). Similarly, cardiac tissue fibrosis was not changed (FIG. 7h). In order to obtain a more efficient removal of GATA2 in ECs, $GATA2^{flox/flox}$ mice were crossed with endothelial Cre expressing VE-Cadherin-CreER mice. DNA recombination was induced by intraperitoneal tamoxifen injections at the age of 6 weeks. The resulting G2-EC-KO (VE-Cad) mice exerted a significant reduction (by 90%) of Gata2 mRNA expression in isolated cardiac ECs compared to control mice ($GATA2^{flox/flox}$, VVT and VE-Cadherin-CreER mice with tamoxifen injection, FIG. 2f). TAC led to a significantly increased mortality in G2-EC-KO (VE-Cad) mice compared to control mice (FIG. 2g). No mortality was observed after sham operation. Echocardiography in surviving mice revealed a reduced cardiac systolic function in VE-Cadherin-CreER based G2-EC-KO compared to control mice after TAC (FIG. 2h, FIG. 7j-k). The capillary/cardiomyocyte ratio was similarly increased in both groups of mice after TAC (FIG. 2i) and no difference in myocardial fibrosis was noted (FIG. 7l). Because these results suggested that ECs with reduced GATA2 levels trigger cardiomyocyte hypertrophy and dysfunction, a co-culture system was established to test whether a direct interaction between both cell types was involved. Cardiac ECs of $GATA2^{flox/flox}$ mice were isolated and transduced with Cre-recombinase (Ad.Cre) or lacZ (Ad.Control) adenoviruses (FIG. 2j). Ad.Cre led to reduced GATA2 in ECs, and cardiomyocytes plated on top displayed enhanced hypertrophy compared to those plated on Ad.Control infected ECs (FIG. 2k-l).

EXAMPLE 4—RELEASE OF GADLOR LNCRNAS DUE TO REDUCED GATA2

Next, it was assessed how reduced GATA2 levels in ECs might lead to cardiac failure. Therefore, cardiac ECs of control or G2-EC-KO mice were isolated and their transcriptome was analyzed by microarray (FIG. 3a). In total, 398 RNAs were significantly regulated by more than two-fold (280 up and 118 down) in response to reduced GATA2. The two most prominently upregulated transcripts in GATA2 depleted cardiac ECs were the unnamed RNAs AK037972 (Log 2FC=5.2) and AK038629 (Log 2FC=3.5). Because their expression was suppressed by GATA2 they were named GATA Downregulated LOng non-coding RNA (GADLOR)1 and 2. A screen of GADLOR1 and 2 expression revealed a highly overlapping pattern in different mouse organs (FIG. 8a). The strong upregulation of GADLOR1 and 2 RNAs in cardiac ECs from G2-EC-KO versus control mice was confirmed by qPCR, but the exposure to TAC or sham surgery did not have an additional effect (FIG. 3b-c). VE-Cadherin-CreER based G2-EC-KO mice also exerted a highly significant upregulation of GADLOR1 and 2 in cardiac ECs, although to a somewhat lesser extent (FIG. 3d-e). In contrast, in WT mice, GADLOR1 and 2 appeared transiently suppressed very early (1 week), but not late (8 weeks) after TAC in cardiac ECs (FIG. 8b). Comparison of GADLOR1 and 2 expression in purified cardiac ECs versus heart tissue from control and G2-EC-KO (VE-Cad) mice revealed high enrichment of both RNAs in ECs (FIG. 3d-e).

GADLOR1 is 2296 base pairs (bp) long and exerts only scattered short fragments of possible protein coding regions, with a maximum length of 77 amino acids (FIG. 9). None of these potential peptide fragments matched any known mouse peptides using blastp search (NCBI). GADLOR2 is 1393 bp long and similar to GADLOR1 only scattered very short potential reading frames encoding either 35 or less amino acids were found, which do not show similarities to known mouse peptides (FIG. 9). SDS-Gel and subsequent mass-spectrometry did not identify any of the potential peptides in mouse C166 ECs with adenoviral overexpression of GADLOR1 or GADLOR2. It was therefore concluded that GADLOR1 and GADLOR2 are lncRNAs. Both lncRNAs do not share any significant similarities. They are encoded on mouse chromosome 16 and are located in close proximity to each other, with only 3601 bp between them (FIG. 3f). They are embedded in the intron after exon 1 of the Lsamp gene, which encodes the limbic system-associated membrane protein that is mainly expressed in the brain, where it regulates for example locomotion and anxiety. Lsamp gene expression was not detected in our microarray from cardiac ECs. Interestingly, the GADLOR1 and 2 sequences are highly conserved between mouse, rat, rabbits, humans and dogs (FIG. 3f). The sequence (−3365 bp) upstream of GADLOR1 were analyzed as potential promoter region (FIG. 3g) and 24 possible GATA binding sites were identified. A chromatin immunoprecipitation (ChIP) with anti-myc or control IgG from C166 mouse ECs infected with a GATA2-myc expressing adenovirus revealed GATA2 binding especially in the region detected by the primer pairs #1 and #4, which also contain GATA consensus binding motifs (FIG. 3g). Accordingly, GATA2 expression dose dependently suppressed luciferase activity driven by the putative −3365 bp promoter region. Similar results were obtained when analysing the −3581 bp region upstream of GADLOR2, in which 26 potential GATA sites were identified. A ChIP assay demonstrated binding of GATA2 (in region detected by primers #4 and #5, both containing GATA sites) and GATA2 potently suppressed the activity of the promoter (FIG. 3*h*). Because reduced GATA2 led to increased endothelial GADLOR1/2 expression in mouse hearts and because reduced GATA2 levels in human failing hearts were detected, GADLOR expression in heart tissue and serum of patients with heart failure or hypertrophy was analyzed. Interestingly, the expression of GADLOR1 and 2 were highly upregulated in the myocardium of patients with endstage heart failure before receiving cardiac transplantation (FIG. 3*i*). Similarly, GADLOR1/2 levels were significantly elevated in the serum of patients with cardiac hypertrophy due to aortic stenosis (FIG. 3*j*, Table 2).

EXAMPLE 5—GADLORS INTERFERE WITH CARDIOMYOCYTE STRESS SIGNALLING

To understand the reasons for the development of cardiomyopathy in G2-EC-KO mice, pressure-overload induced stress signalling was assessed by immunoblot (FIG. 4*a*, FIG. 10*a-d*). Compared to control mice, G2-EC-KO mice showed markedly reduced phosphorylation (i.e. activation) of p38MAPK and some degree of reduced Akt, ERK and JNK phosphorylation after TAC. Immunofluorescence analysis with phospho-specific antibodies revealed that reduced Akt and p38 activation in the knock-out mice occurred in cardiomyocytes (FIG. 4*b*). This was accompanied by increased cardiac RCAN1.4 mRNA expression in G2-EC-KO mice after TAC, indicative of increased calcineurin/NFAT activation (FIG. 4*c*).

It was hypothesized that the high expression of GADLORs in ECs of the GATA2 mutant mice triggers dysregulation of signalling in cardiomyocytes. Thus, we examined whether the GADLORs are secreted by cardiac ECs and taken up by cardiomyocytes to regulate signalling in these cells. To address this, we studied cardiac ECs from $GATA2^{flox/flox}$ mice, in which GATA2 was eliminated by adenoviral Cre expression. Cre transduced ECs exerted increased GADLOR1/2 levels (FIG. 4*d*). Because RNA can travel from one cell to another via extracellular vesicles like exosomes, these were isolated from the supernatant of Ad.Control or Ad.Cre infected mouse cardiac ECs and transferred them to rat cardiomyocytes. Compared to rat cardiomyocytes without any exosome treatment, exosomes from Ad.Control mouse ECs entailed strong enrichment of mouse GADLOR1/2 (assessed by mouse specific qPCR), indicating a constitutive release of GADLORs into endothelial cell derived vesicles (FIG. 4*d*). Cardiomyocyte enrichment of mouse endothelial GADLORs was significantly higher, when exosomes from GATA2 depleted ECs were applied. Another model was established, in which GADLOR1 or 2 (Ad.GADLOR1/Ad.GADLOR2) or lacz (Ad-.Control) was overexpressed by adenovirus in C166 ECs, isolated exosomes from the supernatant and transferred them to cardiomyocytes. After 4 hours of incubation, the cardiomyocytes were washed and RNA was either extracted immediately or after further culturing of the cardiomyocytes. 24 hours after removal of the exosome containing medium, exosomes were still detectable in cardiomyocytes and GADLORs were highly abundant in cardiomyocytes treated with GADLOR1 or 2 overexpressing versus control exosomes (FIG. 4*e* and FIG. 11*b*). Interestingly, GADLOR1/2 overexpression in cardiomyocytes was detected already after 4 hours of incubation with GADLOR exosomes and continued to be evident after 48 hours (FIG. 11*a, c*) and 72 hours (FIG. 4*e*). Next, the functional consequences of GADLOR uptake in cardiomyocytes were assessed. Because reduced activation of p38 and Akt kinases in G2-EC-KO hearts was found, the impact of GADLOR on cellular signal-transduction was tested. Cardiomyocytes were pre-treated either with endothelial control exosomes or exosomes containing GADLOR1 and 2. 24 hours later, the cardiomyocytes were stimulated with the α-adrenergic agonist phenylephrine (PE) or the protein synthesis inhibitor and direct activator of stress protein kinases anisomycin for 15 min and 24 hours. Assessment of kinase activation demonstrated enhanced activation of p38, ERK and JNK mainly 15 minutes and of Akt 24 hours after the addition of PE to cardiomyocytes treated with control exosomes, while in contrast, p38 as well as Akt activation were markedly blunted in cardiomyocytes treated with GADLOR1 and 2 exosomes (FIG. 4*f*). ERK and JNK activation appeared unchanged. Treatment with exosomes that contained either GADLOR1 or 2 alone had only a minor effect (FIG. 10*m*). In response to anisomycin, protein kinase phosphorylation was not different between control and GADLOR exosomes treated cardiomyocytes (FIG. 4*f*). All blots shown in FIG. 4 were also quantified (FIG. 10*e-l*). These results indicated GADLOR dependent interference with adrenergic signal transduction. Increased NFAT-dependent luciferase activity in PE stimulated cardiomyocytes after GADLOR exposition was also found (FIG. 4*g*). In conclusion, uptake of endothelial derived GADLOR1 and 2 in cardiomyocytes was observed where they decreased p38 and Akt activation, but enhanced NFAT activation in response to PE, a pattern that was similarly detected in vivo in G2-EC-KO mice after TAC.

EXAMPLE 6—GADLORS BIND THE RAS-LIKE PROTEIN TC21

It was shown that lncRNAs specifically interact with signalling proteins[19,20]. Because changes in cellular signal transduction by GADLORs wee found, it was screened for cardiomyocyte proteins that interact with these lncRNAs. GADLOR2 coated beads or beads alone (as control) were incubated with cardiomyocyte protein lysate (FIG. 5*a*). After washing, binding candidate proteins were eluted and subjected to SDS-gel electrophoresis. Proteins that interacted with GADLOR-beads, but not control beads were forwarded to mass-spectrometry. As shown in FIG. 5*b*, several proteins of different functional classes were found to interact with GADLOR2, but not with beads alone. Among them were multiple known RNA-binding proteins like Argonaute-2 and hnRNPA2/B1, multiple ubiquitin related, structural proteins and proteins related to vesicle formation. Two signalling proteins were identified in the screen: the Ras superfamily members TC21 (also called RRas2) and Ral-A. Since Ral-A was shown to be a target of TC21, it was focused on the more upstream TC21[21]. First, the interaction of TC21 with GADLORs was verified by RNA immunoprecipitation in HEK293 cells transduced with TC21-myc and GADLOR1 and 2 expressing plasmids (FIG. 5*c*). Interestingly, p38 and Akt activities were induced by an active mutant of TC21 (TC21-V23) in control exosomes treated cells, but this was markedly blunted in the presence of GADLORs containing exosomes (FIG. 5*d-f*). Because these results implied that GADLORs modulate TC21 dependent signal-transduction, it was hypothesized that this might be the result of altered interaction of TC21 with its downstream target molecules (e.g. PI3 Kinase, PI3K). Indeed, PI3K was co-immunoprecipitated with TC21 under control conditions, but this interaction was strongly reduced in the presence of GADLOR1/

2, which likely reduced PI3K activation by TC21 and further downstream signalling (FIG. 5g-h). Thus, exosome derived GADLORs interacted with TC21 and thereby reduced activation of p38 and Akt.

EXAMPLE 7—GADLORS INDUCE CARDIOMYOPATHY

To decipher the functional consequences of increased GADLOR expression during heart failure, control, GADLOR1, GADLOR2 or GADLOR1 and 2 containing exosomes were administered before TAC surgery to mouse hearts by intra-ventricular injection with simultaneous clamping of the aorta and pulmonary artery, to achieve perfusion of exosomes through the coronary arteries (FIG. 6a). Increased GADLOR1 expression was detectable in mouse hearts one week after GADLOR1 and GADLOR1/2 administration. GADLOR2 was significantly upregulated upon administration of GADLOR1/2 (FIG. 6b). Decreased cardiac function was found in mice that received exosomes containing both GADLOR1 and 2, while for mice receiving either GADLOR1 or GADLOR2 only a trend was observed (FIG. 6c and data not shown). Echocardiography in a second cohort of mice that was followed for 2 weeks after TAC also showed reduced cardiac function as well as increased wall thickness (as sign of hypertrophic remodeling), but no ventricular dilation (normal left ventricular end-diastolic area, LVEDA) in response to GADLOR exosomes (FIG. 6c-d). Molecular analysis of mouse hearts showed increased levels of BNP (indicative of aggravated cardiomyopathy) and increased RCAN1.4 expression (showing increased calcineurin/NFAT activation) in mice after treatment with GADLOR1, GADLOR2 and GADLOR1/2 containing exosomes (FIG. 6e). Analysis of p38 and Akt showed reduced activation of both kinases in GADLOR versus control exosome treated mouse hearts (FIG. 6f-g) in agreement with what was observed in vitro (see FIG. 4f). While these results indicated that exosomal delivery of GADLOR1 and 2 in combination is sufficient to aggravate cardiomyopathy after TAC, it was next assessed whether enhanced GADLOR expression is necessary for the development of cardiomyopathy in G2-EC-KO mice. For this purpose, locked nucleic acid (LNA) modified antisense oligonucleotides termed GapmeRs were employed, which degrade lncRNAs in a sequence specific manner-. First specific GapmeR molecules were identified capable of reducing GADLOR1 or GADLOR2 in vitro and in cardiac ECs in mice in vivo (FIG. 11d-f). TAC surgery in control and G2-EC-KO (VE-Cad) mice was performed and that were then treated either with control or GADLOR1 and GADLOR2 targeting GapmeRs by bi-weekly intraperitoneal administration for 4 weeks (FIG. 6h). During treatment with control GapmeRs, increased cardiac hypertrophy and pulmonary congestion were noted in G2-EC-KO (VE-Cad) compared to control mice (FIG. 6i). Remarkably, treatment with GADLOR targeting GapmeRs abolished the increased cardiac hypertrophy in G2-EC-KO (VE-Cad) mice. In addition, GADLOR specific GapmeRs improved cardiac function compared to control GapmeR treatment in G2-EC-KO mice and ameliorated the effects of endothelial GATA2 deletion on p38 activation, but not on Akt activation (FIG. 6j-l). Hence, increased GADLORs expression played a crucial role for driving aggravated cardiac hypertrophy, dysfunction and diminished p38 activation during TAC in G2-EC-KO mice. Our findings are summarized in FIG. 12.

EXAMPLE 8—DISCUSSION

Capillary ECs acquire a highly abnormal morphology in advanced heart failure[23]. A recent study in dogs suggested that mechanical over-loading itself triggers de-differentiation of cardiac ECs[24]. Similarly, it is demonstrate here that the endothelial signature transcription factor GATA2 is downregulated by mechanical overload and that this promoted the development of heart failure. A direct effect of ECs on adjacent cardiomyocytes was confirmed by an in vitro co-culture model of both cell types, in which endothelial GATA2 depletion aggravated cardiomyocyte hypertrophy. Endothelial GATA2 elimination in mice was achieved by using two different endothelial Cre driver lines, whereby the VE-Cadherin-CreER line is known to be more efficient and specific towards ECs compared to the Tie2-CreER line[25,26]. Accordingly, a better elimination of endothelial GATA2 in G2-EC-KO (VE-Cadherin) mice and a stronger phenotype with increased mortality during TAC were observed.

GATA2 depletion caused a markedly increased expression of GADLOR1 and GADLOR2, which are two previously unknown lncRNAs that were identified and named within this study. Both are encoded on chromosome 16 in close proximity to each other and are co-expressed in various tissues. GADLOR1 and GADLOR2 are not part of the same transcript (data not shown), but rather controlled by separate 5'promoter regions, which are both bound and dose-dependently suppressed by GATA2. Indeed, GATA factors in general and also specifically GATA2 can act as transcriptional repressor, for instance in conjunction with histone deacetylases[27,28].

GADLOR1 and 2 are excreted from cardiac ECs within extracellular vesicles and are efficiently taken up by cardiomyocytes. Similarly, transfer of lncRNAs (TUC339 and linc-ROR) within extracellular vesicles among human hepatocellular cancer cells contributes to disease progression and resistance to chemotherapy[29,30]. Cardiomyocytes appear to be a prime target of extracellular vesicles, as transfer of endothelial miR146a or miR21* from fibroblasts to cardiomyocytes within vesicles has also been described[10,31]. In cardiomyocytes, it was found that GADLOR1 and 2 bind the upstream signalling protein TC21 from the Ras family, which was previously linked to PI3K and subsequent p38 and Akt activation[21]. Binding of GADLORs prevented interaction of TC21 with its direct downstream target PI3K and activation of p38 and Akt. Since both GADLORs were induced in GATA2 knock-out mice, most of the experiments were performed with the combination of GADLOR1 and 2. Indeed, the combination of both lncRNAs was more potent to influence signalling in cardiomyocytes and to induce heart failure compared to the administration of either lncRNAs alone. How both GADLORs act together and whether they form dimers will have to be the subject of future studies.

Protein binding by lncRNAs is commonly part of their mechanism of action[32,33], for instance during recruitment of epigenetic factors to certain DNA regions[34]. It was recently demonstrated that lncRNAs bind cytosolic signalling molecules and thereby modulate signal-transduction[19,20]. Here, a new paradigm is established, whereby lncRNAs efficiently act on signal-transduction in neighbouring cells: According to this exemplary mechanism, ECs are able to attenuate intracellular stress signalling within a given tissue through paracrine transfer of GADLOR lncRNAs, perhaps in order to synchronize signalling responses between adjacent cells. Although modulation of cardiomyocyte stress-signalling by endothelial GADLORs may be desirable to a certain extent, pronounced GADLOR expression clearly triggers heart failure, which will at least in part be the consequence of reduced p38 and Akt and enhanced calcineurin activation: Cardiomyocyte specific genetic deletion of p38 or general deletion of Akt1 in mice aggravated cardiac dysfunction after TAC[35,36]. p38 has been identified as negative regulator of calcineurin/NFAT signalling in the myocardium[37], therefore enhanced activation of myocardial calcineurin in G2-EC-KO and GADLOR treated cells or mice is likely the consequence of diminished p38 activation. Activated calcineurin/NFAT signalling, in turn, was shown to induce heart failure[38].

Increased levels of GADLOR1 and 2 in heart failure patients suggest that our findings are transferable to humans. Therapeutic strategies could be developed to reduce GADLOR expression and halt progression of the disease in patients. Our endothelial GATA2 mutant mice are a useful model to develop these strategies: Indeed, combined experimental ablation of both GADLORs ameliorated cardiac hypertrophy and heart failure in G2-EC-KO mice. This is in line with recent studies suggesting lncRNAs as valuable therapeutic targets in heart failure[39-45]. Because circulating exosomal lncRNAs are useful as biomarker, this is expected to apply also for the GADLORs, which were found increased in serum of heart failure patients[46,47].

TABLE 1

Key reagents, mice and software used in the study

| Reagents, Mice or Software | Source | Identifier | SEQ ID NO |
|---|---|---|---|
| Antibodies | | | |
| Anti-CD31 | BD Pharmingen | 553370 | |
| Anti-CD102 | BD Biosciences | 553326 | |
| Anti-CD146 | Miltenyi Biotech | 130-092-007 | |
| Anti-α-actinin | Sigma-Aldrich | A7811 | |
| Anti-myc | Cell Signaling | 2276 | |
| Anti-phospho-Akt | Cell Signaling | 9271 | |
| Anti-total-Akt | Cell Signaling | 9272 | |
| Anti-phospho-38 MAPK | Cell Signaling | 9211 | |
| Anti-total-p38 MAPK | Cell Signaling | 9212 | |
| Anti-phospho-ERK1/2 | Cell Signaling | 9101 | |
| Anti-ERK 1/2 | Cell Signaling | 9102 | |
| Anti-phospho-SAPK-JNK | Cell Signaling | 9251 | |
| Anti-total-SAPK-JNK | Cell Signaling | 9252 | |
| Anti-GATA2 | Abcam | ab109241 | |
| Anti-PI3 Kinase p85 | Millipore | 06-195 | |
| Anti-TC21/R-Ras2 | R&D Systems | AF3605 | |
| Anti-actin | Sigma-Aldrich | C6198 | |
| Anti-Rabbit/Mouse IgG Alexa Fluor ® 488 or secondary antibody | New England Biolabs | 4412 | |
| Anti-Rabbit/Mouse IgG Alexa Fluor ® 555 secondary antibody | New England Biolabs | 4409 | |
| Chemicals | | | |
| Lipofectamine 2000 reagent | Invitrogen | 11668-027 | |
| Phenylephrine | Sigma-Aldrich | P6126 | |
| ExoQuick-TC ™ exosome precipitation solution | SBI System Biosciences | EXOTC50A | |
| Sodium nitroprusside dihydrate | Sigma-Aldrich | 71780 | |
| Green fluorescent dye PKH67 | Sigma-Aldrich | MINI67 | |
| Passive Lysis Buffer | Promega | E1941 | |
| Trifast reagent | Peqlab | 30-2020 | |
| Protein A/G PLUS Agarose beads | Santa Cruz | sc-2003 | |
| Biotin RNA Labeling Mix | Roche | 11685597910 | |
| T7 RNA polymerase | Roche | 10881767001 | |
| Streptavidin agarose beads | Millipore | 16-126 | |
| Normal mouse IgG | Santa Cruz | sc-2025 | |
| Normal goat IgG | Santa Cruz | sc-2028 | |
| TRITC-conjugated wheat germ agglutinin (WGA) | Sigma-Aldrich | L5266 | |
| Isolectin B4 | Vector Laboratories | FL-1201 | |
| Mounting Medium with DAPI | Roth | HP20.1 | |
| Tamoxifen | Sigma-Aldrich | T5648 | |
| Critical Commercial Kits | | | |
| AdEasy Adenoviral Vector System | Agilent Technologies | 240009 | |
| NucleoSpin RNA II kit | Macherey Nagel | 740955250 | |
| RNeasy mini kit | Qiagen | 74104 | |
| Maxima H Minus First Strand cDNA Synthesis Kit | Thermo Scientific | EP0751 | |
| Maxima SYBR Green qPCR Master Mix | Thermo Scientific | K0253 | |
| Whole Mouse Genome Microarray 4 × 44K | Agilent | G4122F | |
| Tissue scan Normal Tissue qPCR Arrays | OriGene Technologies | MNRT301 | |
| PCR purification kit | Thermo Scientific | K0701 | |
| ChIP Assay kit | Merck-Millipore | 17-295 | |
| Magna RIP ™ RNA-Binding Protein Immunoprecipitation Kit | Merck-Millipore | 17-700 | |

TABLE 1-continued

Key reagents, mice and software used in the study

| Reagents, Mice or Software | Source | Identifier | SEQ ID NO |
|---|---|---|---|
| Experimental Models: Cell Lines | | | |
| HEK293 | Leibniz Institute DSMZ | Cell Line 293 ACC: 305 | |
| NIH3T3 | ATCC | CL-173 | |
| C166 | ATCC | CRL-2581 | |
| COS-1 | Laboratory of Kai C. Wollert | N/A | |
| Experimental Models: Organisms/Strains | | | |
| Mouse: GATA2floxflox | Laboratory of Sally A. Camper | N/A | |
| Mouse: Tie2ERT2Cre | Laboratory of Bernd Arnold | N/A | |
| Mouse: Cdh5(PAC)-CreERT2 | Laboratory of Ralf H. Adams | N/A | |
| Mouse: GATA2floxflox × Tie2-CreER | Provided herein | N/A | |
| Mouse: GATA2floxflox × VE-Cadherin-CreER | Provided herein | N/A | |
| Mouse: C57BL/6 | The Jackson Laboratory | JAX: 000664 | |
| Recombinant DNA | | | |
| Vector: pGL2 basic | Promega | E1641 | |
| Plasmid: pGADLOR1-Luc | Provided herein | N/A | |
| Plasmid: pGADLOR2-Luc | Provided herein | N/A | |
| Plasmid: RRAS2 | Addgene | 38816 | |
| Vector: pShuttleCMV | Agilent Technologies | 240007 | |
| Plasmid: pshuttleCMV-TC21-myc | Provided herein | N/A | |
| Plasmid: Myc-tagged TC21-V23 | Laboratory of Christopher J. Marshall | Rosario et al., 2001 | |
| Adenovirus expressing β-Gal | Previous work | Froese et al., 2011 | |
| Adenovirus expressing Cre | Previous work | Froese et al., 2011 | |
| Adenovirus expressing GATA-Iuc | Previous work | Froese et al., 2011 | |
| Adenovirus expressing NFAT-Iuc | Previous work | Heineke et al., 2010 | |
| cDNA clone AK037972 | Source BioScience | ID A130068D08 | |
| cDNA clone AK038629 | Source BioScience | ID A230051L22 | |
| Human GATA2 cDNA clone | Open Biosystems | BC006793 | |
| Plasmid: pshuttleCMV-GATA2-myc | Provided herein | N/A | |
| Adenovirus expressing myc-tagged human GATA2 | Provided herein | N/A | |
| Sequence-Based Reagents | | | |
| LNA long RNA GapmeR scramble control: 5'-AACACGTCTATACGC-3' | Exiqon | 500175 | 19 |
| LNA long RNA GapmeR targeting GADLOR1: 5'-TGCAAGATGATTGAGA-3' | Exiqon | 500175 | 20 |
| LNA long RNA GapmeR targeting GADLOR2: 5'-TCAAGGATAGAGGTT-3' | Exiqon | 500175 | 21 |
| qPCR primers for mouse Gapdh: 5'-CCGCATCTTCTTGTGCAGT -3' and 5'-CATCACCTGGCCTACAGGAT -3' | Provided herein | N/A | 23, 24 |
| qPCR primers for mouse β-MHC: 5'-AGGCAAGGCAAAGAAAGGCTCATC -3' and 5'-GCGTGGAGCGCAAGTTTGTCATAA -3' | Provided herein | N/A | 24, 25 |
| qPCR primers for mouse α-MHC: 5'-ACTGTGGTGCCTCGTTCC -3' and 5'-GCCTCTAGGCGTTCCTTCTC -3' | Provided herein | N/A | 26, 27 |

TABLE 1-continued

Key reagents, mice and software used in the study

| Reagents, Mice or Software | Source | Identifier | SEQ ID NO |
|---|---|---|---|
| qPCR primers for mouse SERCA2a: 5'-ACGTGCCTGGTGGAGAAGATGAAT -3' and 5'-ATCTTGCTCATGGATGTCCGGCTT -3' | Provided herein | N/A | 28, 29 |
| qPCR primers for mouse Gata2: 5'-GCACCTGTTGTGCAAATTGT -3' and 5'- AGGGCGGTGACTTCTCTTG -3' | Provided herein | N/A | 30, 31 |
| qPCR primers for mouse BNP: 5'-CTCAAGCTGCTTTGGGCACAAGAT -3' and 5'-AGCCAGGAGGTCTTCCTACAACAA -3' | Provided herein | N/A | 32, 33 |
| qPCR primers for mouse RCAN1.4: 5'-GCTTGACTGAGAGAGCGAGTC -3' and 5'-CCACACAAGCAATCAGGGAGC -3' | Provided herein | N/A | 34, 35 |
| qPCR primers for GADLOR1: 5'-TTACATGGTTCCCTACCCAGACCA -3' and 5'-GGGTGGCATGCAAGATGATTGAGA -3' | Provided herein | N/A | 11, 12 |
| qPCR primers for GADLOR2: 5'-AGGACTTGCAGGGACTCACA -3' and 5'- TCAATAGCCATTCAGTTTTCAA -3' | Provided herein | N/A | 13, 14 |
| qPCR primers for mouse specific GADLOR1: 5' AGCTTGGGCAAACTCCTTA -3' and 5'-GAAGTCTTAAAAATGCATGGC -3' | Provided herein | N/A | 15, 16 |
| qPCR primers for mouse specific GADLOR2: 5'-CACAGTGTGTCATATTTTGCA -3' and 5'- CAAAGGAACACCTTCATAGC -3' | Provided herein | N/A | 17, 18 |
| ChIP assay primer 1 for GADLOR1: 5'-CAATTACAAACACTGAAGTAACAATTT -3' and 5'-GCCCTCTTCTGGCCTCTAAA -3' | Provided herein | N/A | 36, 37 |
| ChIP assay primer 2 for GADLOR1: 5'-GGCTGAGCCATTTCATCTCT -3' and 5'- TATCCACGTGCACTCACACA -3' | Provided herein | N/A | 38, 39 |
| ChIP assay primer 3 for GADLOR1: 5'-ATTTGTTCGGTTTGGCAATG -3' and 5'- GACGGCTCAAGAGGTAAGCTA -3' | Provided herein | N/A | 40, 41 |
| ChIP assay primer 4 for GADLOR1: 5'-GAGACAGGCACCCAGAAGAC -3' and 5'- CACACCCCTCTTTTGCTTTC -3' | Provided herein | N/A | 42, 43 |
| ChIP assay primer 5 for GADLOR1: 5'-CTCACCTCTTCCTGGCTCAC -3' and 5'- TCCCTTTTCCATTCCTCTCA -3' | Provided herein | N/A | 44, 45 |
| ChIP assay primer 1 for GADLOR2: 5'-TTCCTTGCTGGGTATCTTGG -3' and 5'- GCCCTCTTCTGGCCTCTAAA -3' | Provided herein | N/A | 46, 47 |
| ChIP assay primer 2 for GADLOR2: 5'-CGTGGCAGCAAGTTAAATCA -3' and 5'- CTGTGGCAGTGTTGCCTCTA -3' | Provided herein | N/A | 48, 49 |
| ChIP assay primer 3 for GADLOR2: 5'-TTTGCATTTCTGATACTTACTGGA -3' and 5'- CGAGGTCATTGAAATCGCTTA -3' | Provided herein | N/A | 50, 51 |
| ChIP assay primer 4 for GADLOR2: 5'-GGAGACCGAGATCAAGCAAA -3' and 5'- TGGTCCTTTGAACCCTCATT -3' | Provided herein | N/A | 52, 53 |
| ChIP assay primer 5 for GADLOR2: 5'-TTGAAGATGTTGCAAACAAGAA -3' and 5'- AGGTGAAGTGGGATTTGTGC -3' | Provided herein | N/A | 54, 55 |
| RIP assay primer for GADLOR1: 5'-TTACATGGTTCCCTACCCAGACCA -3' and 5'- GGGTGGCATGCAAGATGATTGAGA -3' | Provided herein | N/A | 56, 57 |
| RIP assay primer for GADLOR2: 5'-AGGACTTGCAGGGACTCACA -3' and 5'- TCAATAGCCATTCAGTTTTCAA -3' | Provided herein | N/A | 58, 59 |
| **Software and Algorithms** | | | |
| Graph Pad Prism 6 | Graph Pad software | N/A | |
| Feature Extraction Software v10.7.3.1 | Agilent | N/A | |

TABLE 1-continued

| Key reagents, mice and software used in the study | | | |
|---|---|---|---|
| Reagents, Mice or Software | Source | Identifier | SEQ ID NO |
| Limma | Bioconductor | N/A | |
| Quantity One | Bio-Rad | N/A | |

TABLE 2

| Clinical characteristics of the patients undergoing implantation of a left ventricular assist device (LVAD) | | |
|---|---|---|
| | LVAD N = 19 | Normal values |
| Age (years) | 59.7 ± 10.9 | |
| Sex (M/F, %) | 94.7/5.3 | |
| Echocardiography | | |
| Ejection fraction (%) | 18.9 ± 4.9 | >55 |
| Septum thickness (mm) | 29.4 ± 34.8 | ≤11 |
| Serum | | |
| Creatinine (μmol/l) | 132.6 ± 73 | 59-104 |
| Clinical Classification | | |
| NYHA I [% of all patients] | 0 | |
| NYHA II [% of all patientsl | 0 | |
| NYHA III [% of all patients] | 35.7 | |
| NYHA IV [% of all patients] | 64.3 | |

Data are displayed as mean ± SEM or in % of all patients as indicated. NYHA indicates New York Heart Association Class.

TABLE 3

| Clinical characteristics of the patients with aortic stenosis. | | |
|---|---|---|
| | Aortic stenosis N = 24 | Normal values |
| Age (years) | 79.5 ± 2.2 | |
| Sex (M/F, %) | 96/4 | |
| Echocardiography | | |
| Ejection fraction (%) | 30 ± 12.6 | >55 |
| Septum thickness (mm) | 13.8 ± 4.2 | ≤11 |
| Serum | | |
| Creatinine (μmol/l) | 136.6 ± 9.1 | 59-104 |
| Clinical Classification | | |
| NYHA I [% of all patients] | 12.5 | |
| NYHA II [% of all patients] | 16.7 | |
| NYHA III [% of all patients] | 58.3 | |
| NYHA IV [% of all patients] | 12.5 | |

Data are displayed as mean ± SEM or in % of all patients as indicated. NYHA indicates New York Heart Association Class.

REFERENCES

1 Heineke, J. & Molkentin, J. D. Regulation of cardiac hypertrophy by intracellular signalling pathways. *Nat Rev Mol Cell Biol* 7, 589-600 (2006).
2 Hill, J. A. & Olson, E. N. Cardiac plasticity. *N Engl J Med* 358, 1370-1380, doi:10.1056/NEJMra072139 (2008).
3 Heineke, J. et al. Cardiomyocyte GATA4 functions as a stress-responsive regulator of angiogenesis in the murine heart. *J Clin Invest* 117, 3198-3210, doi:10.1172/JC132573 (2007).
4 Sano, M. et al. p53-induced inhibition of Hif-1 causes cardiac dysfunction during pressure overload. *Nature* 446, 444-448 (2007).
5 Mohammed, S. F. et al. Coronary microvascular rarefaction and myocardial fibrosis in heart failure with preserved ejection fraction. *Circulation* 131, 550-559, doi:10.1161/CIRCULATIONAHA.114.009625 (2015).
6 Izumiya, Y. et al. Vascular Endothelial Growth Factor Blockade Promotes the Transition From Compensatory Cardiac Hypertrophy to Failure in Response to Pressure Overload. *Hypertension* (2006).
7 Tirziu, D. et al. Myocardial hypertrophy in the absence of external stimuli is induced by angiogenesis in mice. *J Clin Invest* 117, 3188-3197, doi:10.1172/JC132024 (2007).
8 Heineke, J. Wag the dog: how endothelial cells regulate cardiomyocyte growth. *Arterioscler Thromb Vasc Biol* 32, 545-547, doi:10.1161/ATVBAHA.111.242784 (2012).
9 Appari, M. et al. C1q-TNF-Related Protein-9 Promotes Cardiac Hypertrophy and Failure. *Circ Res* 120, 66-77, doi:10.1161/CIRCRESAHA.116.309398 (2017).
10 Halkein, J. et al. MicroRNA-146a is a therapeutic target and biomarker for peripartum cardiomyopathy. *J Clin Invest* 123, 2143-2154, doi:10.1172/JC164365 (2013).
11 Mammoto, A. et al. A mechanosensitive transcriptional mechanism that controls angiogenesis. *Nature* 457, 1103-1108, doi:nature07765 [pii]10.1038/nature07765 (2009).
12 Linnemann, A. K., O'Geen, H., Keles, S., Farnham, P. J. & Bresnick, E. H. Genetic framework for GATA factor function in vascular biology. *Proc Natl Acad Sci USA* 108, 13641-13646, doi:10.1073/pnas.1108440108 (2011).
13 Tsai, F. Y. et al. An early haematopoietic defect in mice lacking the transcription factor GATA-2. *Nature* 371, 221-226, doi:10.1038/371221a0 (1994).
14 Lim, K. C. et al. Conditional Gata2 inactivation results in HSC loss and lymphatic mispatterning. *J Clin Invest* 122, 3705-3717, doi:10.1172/JC161619 (2012).
15 Johnson, K. D. et al. Cis-element mutated in GATA2-dependent immunodeficiency governs hematopoiesis and vascular integrity. *J Clin Invest* 122, 3692-3704, doi:10.1172/JC161623 (2012).
16 Scheuermann, J. C. & Boyer, L. A. Getting to the heart of the matter: long non-coding RNAs in cardiac development and disease. *EMBO J* 32, 1805-1816, doi:10.1038/emboj.2013.134 (2013).
17 Feyder, M. & Goff, L. A. Investigating long noncoding RNAs using animal models. *J Clin Invest* 126, 2783-2791, doi:10.1172/JC184422 (2016).
18 Fiedler, J. et al. MicroRNA-24 Regulates Vascularity After Myocardial Infarction. *Circulation* 124, 720-730, doi:CIRCULATIONAHA. 111.039008 [pii]10.1161/CIRCULATIONAHA.111.039008 (2011).
19 Lin, A. et al. The LINK-A lncRNA activates normoxic HIF1alpha signalling in triple-negative breast cancer. *Nat Cell Biol* 18, 213-224, doi:10.1038/ncb3295 (2016).
20 Liu, X. et al. LncRNA NBR2 engages a metabolic checkpoint by regulating AMPK under energy stress. *Nat Cell Biol* 18, 431-442, doi:10.1038/ncb3328 (2016).
21 Rosario, M., Paterson, H. F. & Marshall, C. J. Activation of the Ral and phosphatidylinositol 3' kinase signaling pathways by the ras-related protein TC21. *Mol Cell Biol* 21, 3750-3762, doi:10.1128/MCB.21.11.3750-3762.2001 (2001).

22 Michalik, K. M. et al. Long noncoding RNA MALAT1 regulates endothelial cell function and vessel growth. *Circ Res* 114, 1389-1397, doi:10.1161/CIRCRESAHA.114.303265 (2014).

23 Chen, J. et al. Abnormalities of capillary microarchitecture in a rat model of coronary ischemic congestive heart failure. *Am J Physiol Heart Circ Physiol*, ajpheart 00583 02014, doi:10.1152/ajpheart.00583.2014 (2015).

24 Mai, J. et al. Dyssynchronous pacing triggers endothelial-mesenchymal transition through heterogeneity of mechanical stretch in a canine model. *Circ J* 79, 201-209, doi:10.1253/circj.CJ-14-0721 (2014).

25 Wang, Y. et al. Ephrin-B2 controls VEGF-induced angiogenesis and lymphangiogenesis. *Nature* 465, 483-486, doi:10.1038/nature09002 (2010).

26 Forde, A., Constien, R., Grone, H. J., Hammerling, G. & Arnold, B. Temporal Cre-mediated recombination exclusively in endothelial cells using Tie2 regulatory elements. *Genesis* 33, 191-197, doi:10.1002/gene.10117 (2002).

27 Froese, N. et al. GATA6 Promotes Angiogenic Function and Survival in Endothelial Cells by Suppression of Autocrine Transforming Growth Factor {beta}/Activin Receptor-like Kinase 5 Signaling. *J Biol Chem* 286, 5680-5690, doi:M110.176925 [pii]10.1074/jbc.M110.176925 (2011).

28 Ozawa, Y. et al. Histone deacetylase 3 associates with and represses the transcription factor GATA-2. *Blood* 98, 2116-2123 (2001).

29 Kogure, T., Yan, I. K., Lin, W. L. & Patel, T. Extracellular Vesicle-Mediated Transfer of a Novel Long Noncoding RNA TUC339: A Mechanism of Intercellular Signaling in Human Hepatocellular Cancer. *Genes & cancer* 4, 261-272, doi:10.1177/1947601913499020 (2013).

30 Takahashi, K., Yan, I. K., Kogure, T., Haga, H. & Patel, T. Extracellular vesicle-mediated transfer of long noncoding RNA ROR modulates chemosensitivity in human hepatocellular cancer. *FEBS* open bio 4, 458-467, doi:10.1016/j.fob.2014.04.007 (2014).

31 Bang, C. et al. Cardiac fibroblast-derived microRNA passenger strand-enriched exosomes mediate cardiomyocyte hypertrophy. *J Clin Invest* 124, 2136-2146, doi:10.1172/JC170577 (2014).

32 Schonrock, N., Harvey, R. P. & Mattick, J. S. Long noncoding RNAs in cardiac development and pathophysiology. *Circ Res* 111, 1349-1362, doi:10.1161/CIRCRESAHA.112.268953 (2012).

33 Thum, T. & Condorelli, G. Long noncoding RNAs and microRNAs in cardiovascular pathophysiology. *Circ Res* 116, 751-762, doi:10.1161/CIRCRESAHA.116.303549 (2015).

34 Tsai, M. C. et al. Long noncoding RNA as modular scaffold of histone modification complexes. *Science* 329, 689-693, doi:10.1126/science.1192002 (2010).

35 Nishida, K. et al. p38alpha mitogen-activated protein kinase plays a critical role in cardiomyocyte survival but not in cardiac hypertrophic growth in response to pressure overload. *Mol Cell Biol* 24, 10611-10620, doi:10.1128/MCB.24.24.10611-10620.2004 (2004).

36 DeBosch, B. et al. Akt1 is required for physiological cardiac growth. *Circulation* 113, 2097-2104 (2006).

37 Braz, J. C. et al. Targeted inhibition of p38 MAPK promotes hypertrophic cardiomyopathy through upregulation of calcineurin-NFAT signaling. *J Clin Invest* 111, 1475-1486 (2003).

38 Molkentin, J. D. et al. A calcineurin-dependent transcriptional pathway for cardiac hypertrophy. *Cell* 93, 215-228 (1998).

39 Ounzain, S. et al. Genome-wide profiling of the cardiac transcriptome after myocardial infarction identifies novel heart-specific long non-coding RNAs. *Eur Heart J* 36, 353-368a, doi:10.1093/eurheartj/ehu180 (2015).

50 40 Matkovich, S. J., Edwards, J. R., Grossenheider, T. C., de Guzman Strong, C. & Dorn, G. W., 2nd. Epigenetic coordination of embryonic heart transcription by dynamically regulated long noncoding RNAs. *Proc Natl Acad Sci USA* 111, 12264-12269, doi:10.1073/pnas.1410622111 (2014).

41 Yang, K. C. et al. Deep RNA sequencing reveals dynamic regulation of myocardial noncoding RNAs in failing human heart and remodeling with mechanical circulatory support. *Circulation* 129, 1009-1021, doi:10.1161/CIRCULATIONAHA.113.003863 (2014).

42 Wang, K. et al. The long noncoding RNA CHRF regulates cardiac hypertrophy by targeting miR-489. *Circ Res* 114, 1377-1388, doi:10.1161/CIRCRESAHA.114.302476 (2014).

43 Gao, C. & Wang, Y. Transcriptome complexity in cardiac development and diseases—an expanding universe between genome and phenome. *Circ J* 78, 1038-1047 (2014).

44 Han, P. et al. A long noncoding RNA protects the heart from pathological hypertrophy. *Nature* 514, 102-106, doi:10.1038/nature13596 (2014).

45 Viereck, J. et al. Long noncoding RNA Chast promotes cardiac remodeling. *Sci Transl Med* 8, 326ra322, doi:10.1126/scitranslmed.aaf1475 (2016).

46 Li, Q. et al. Plasma long noncoding RNA protected by exosomes as a potential stable biomarker for gastric cancer. *Tumour biology: the journal of the International Society for Oncodevelopmental Biology and Medicine*, doi:10.1007/s13277-014-2807-y (2014).

47 Kumarswamy, R. et al. Circulating long noncoding RNA, LIPCAR, predicts survival in patients with heart failure. *Circ Res* 114, 1569-1575, doi:10.1161/CIRCRESAHA.114.303915 (2014).

48 Forde, A., Constien, R., Grone, H. J., Hammerling, G. & Arnold, B. Temporal Cre-mediated recombination exclusively in endothelial cells using Tie2 regulatory elements. *Genesis* 33, 191-197, doi:10.1002/gene.10117 (2002).

49 Charles, M. A. et al. Pituitary-specific Gata2 knockout: effects on gonadotrope and thyrotrope function. *Mol Endocrinol* 20, 1366-1377, doi:me.2005-0378 [pii] 10.1210/me.2005-0378 (2006).

50 Heineke, J. et al. CIB1 is a regulator of pathological cardiac hypertrophy. *Nat Med* 16, 872-879, doi:nm.2181 [pii] 10.1038/nm.2181 (2010).

51 Haq, S. et al. Differential activation of signal transduction pathways in human hearts with hypertrophy versus advanced heart failure. *Circulation* 103, 670-677 (2001).

52 Lim, Y. C. & Luscinskas, F. W. Isolation and culture of murine heart and lung endothelial cells for in vitro model systems. *Methods Mol Biol* 341, 141-154, doi:10.1385/1-59745-113-4:141 (2006).

53 Heineke, J. et al. Attenuation of cardiac remodeling after myocardial infarction by muscle LIM protein-calcineurin signaling at the sarcomeric Z-disc. *Proc Natl Acad Sci USA* 102, 1655-1660 (2005).

54 Maillet, M. et al. Heart-specific deletion of CnB1 reveals multiple mechanisms whereby calcineurin regulates cardiac growth and function. *J Biol Chem* 285, 6716-6724, doi:M109.056143 [pii] 10.1074/jbc.M109.056143 (2010).

The invention claimed is:

1. A compound inhibiting the expression and/or the activity of a long non-coding RNA (lncRNA) selected from GADLOR 1 and GADLOR 2 for use in treating or preventing cardiac remodelling, wherein GADLOR 1 comprises or consists of a nucleic acid sequence selected from the group consisting of SEQ ID NOs 1 to 3 and sequences being at least 75% identical thereto, and GADLOR 2 comprises or consists of a nucleic acid sequence selected from the group consisting of SEQ ID NOs 4 to 6 and sequences being at least 75% identical thereto, wherein the compound inhibiting the expression and/or the activity of the lncRNA is a nucleotide-based inhibitor.

2. The compound for use according to claim 1, wherein the cardiac remodelling is Heart Failure with preserved Ejection Fraction (HFpEF), Heart Failure with reduced Ejection Fraction (HFrEF), myocardial infarction related cardiac remodelling, a genetic cardiac disease associated cardiac remodelling, cardiac hypertrophy and/or cardiac dysfunction related cardiac remodelling.

3. The compound for use according to claim 2, wherein the cardiac hypertrophy is ventricular hypertrophy, preferably left ventricular hypertrophy, and/or wherein the cardiac dysfunction is ventricular dysfunction, preferably left ventricular dysfunction.

4. The compound for use according to claim 1, wherein the nucleotide-based inhibitor acid is a DNA or RNA aptamer, a ribozyme, a siRNA, a shRNA, or an antisense oligonucleotide.

5. The compound for use according to claim 4, wherein the nucleotide-based inhibitor comprises (a) a nucleic acid sequence which comprises or consists of a nucleic acid sequence being complementary to at least 12 continuous nucleotides of a nucleic acid sequence selected from SEQ ID NOs 1 to 6 or a sequence being at least 75% identical thereto, (b) a nucleic acid sequence which comprises or consists of a nucleic acid sequence which is at least 70% identical to the complementary strand of one or more nucleic acid sequences selected from SEQ ID NOs 1 to 6, (c) a nucleic acid sequence which comprises or consists of a nucleic acid sequence according to (a) or (b), wherein the nucleic acid sequence is DNA or RNA, (d) an expression vector expressing the nucleic acid sequence as defined in any one of (a) to (c), preferably under the control of a myocardium-specific promoter and/or cardiac endothelial cell-specific promoter, or (e) a host comprising the expression vector of (d).

6. The compound for use according to claim 1, wherein a first and a second compound is used, wherein the first compound inhibits the expression and/or the activity of the lncRNA GADLOR 1 and the second compound inhibits the expression and/or the activity of the lncRNA GADLOR 2.

7. A method for diagnosing and treating cardiac remodelling in a patient, comprising (a) detecting the expression level of one or both lncRNA(s) selected from GADLOR 1 and GADLOR 2 as defined in claim 1 in a sample obtained from said patient, (b) comparing said expression obtained in (a) with the expression level of said lncRNA(s) in a sample obtained from at least one healthy subject or with a predetermined standard that has been obtained from a sample of at least one healthy subject, wherein a greater than 1.5-fold upregulation of the lncRNA(s) is indicative for cardiac remodelling in the patient, and (c) administering to the patent a therapeutically effective amount of a compound as defined in claim 1 when a greater than 1.5-fold upregulation of the lncRNA(s) is detected.

8. The method according to claim 7, wherein said sample is a heart tissue sample or a blood sample.

9. The method of claim 7, wherein the detection of the expression level of the lncRNA comprises (a) quantitative PCR, preferably quantitative real time PCR, or (b) a template/RNA amplification method followed by determining the expression level of the lncRNA using a fluorescence- or luminescence-based quantification method.

10. A kit for diagnosing cardiac remodelling in a patient, said kit comprising means for the detection of the expression level of one or both lncRNA(s) selected from GADLOR 1 and GADLOR 2 as defined in claim 1, and instructions how to use the kit.

11. The kit of claim 10, wherein the means are primer pairs used for the specific detection of the lncRNA(s) selected from GADLOR 1 and GADLOR 2.

12. A method for producing a non-human animal model for heart failure comprising (a) the administration of one or more lncRNA selected from GADLOR 1 and GADLOR 2 to the myocardium of the animal, wherein GADLOR 1 comprises or consists of a nucleic acid sequence selected from the group consisting of SEQ ID NOs 1 to 3 and sequences being at least 75% identical thereto, and GADLOR 2 comprises or consists of a nucleic acid sequence selected from the group consisting of SEQ ID NOs 4 to 6 and sequences being at least 75% identical thereto; and (b) the induction of pressure overload in the myocardium of the animal.

13. A non-human animal model for heart failure that has been produced by a method comprising (a) the administration of one or more lncRNA selected from GADLOR 1 and GADLOR 2 to the myocardium of the animal, wherein GADLOR 1 comprises or consists of a nucleic acid sequence selected from the group consisting of SEQ ID NOs 1 to 3 and sequences being at least 75% identical thereto, and GADLOR 2 comprises or consists of a nucleic acid sequence selected from the group consisting of SEQ ID NOs 4 to 6 and sequences being at least 75% identical thereto; and (b) the induction of pressure overload in the myocardium of the animal.

* * * * *

SEQUENCE LISTING

<160> NUMBER OF SEQ ID NOS: 63

<210> SEQ ID NO 1
<211> LENGTH: 2706
<212> TYPE: RNA
<213> ORGANISM: Homo sapiens
<220> FEATURE:
<223> OTHER INFORMATION: GADLOR 1

<400> SEQUENCE: 1

```
guuuaaugcu uuucaccggg auuugacuuc auuauaagag aaaguuucac uuggcuucuc     60
uucgaugacu gguuguggga aaaucuuucu gacaaaucuc aaauugucua gaauguggca    120
guuuaaaaac acaucuacau ugaucuacag ucucaagguc ccaccuuugu guuacuuuua    180
gaauuuguag auggauguua uucagcaagg augacucauc uacauuuggu uugucaauuu    240
guuuucaaag aucauaugua cauagcgucc uucgaucuua cuuucccuuu aaaauaugaa    300
acugauaaug accuugaaaa agacugaggc aaaaaauaua guuccuaag uuuuaccuuu    360
guacccugag uaugcauucu caccuuugug gccagguagu uugggggauu cucaccugau    420
ccccucccuc ccuuugcugc ccuuaaggaa aauaauaacu auuggauacu aggcuuagga    480
cauaggugac aaaauaaauu uuacaacaaa ccccuauggc augaauuuac cuguagaaca    540
aaccugcaca uguaccccga accuaaaauu auuuuuuuaa aaaaacaacu uuuauuaggc    600
ucuuuaaacu gucauguaua ccacuuccac auuuauuuug ggacucaagc uauauuugaa    660
guauuuugug gcccuccuua uuuuuuuuua auauguauau ucuguauuuu uuauguuuuc    720
ccuuugccuu ugaauaccuc ucguaguuua ccuauugcua auaaaugaca uuuuacaagc    780
uuugccuuua uuuuuuuucc aagacccaca uuuacucaag gcuugaagaa guuuuuaaga    840
ccuuuaagau aucuugugca uuauauauau uuauuuguag uuuuucuuua cuaaugaugu    900
cauuuuauca cugucccuu uucuaaaauu aaauaacauu uuugauugau uucuuuggau    960
uucccucuac caccaggaug uggggguugaa uuuuguuaca cacagcuaau uucugcagcu   1020
acuuuuguca gacuccuguc uccccaggcc ccacuuucua auucaugcug caaaugucua   1080
ucauagggag caguuauaaa caccuuuuua ucagucauua aaaaaaaaau ucuaguguuu   1140
guuuuuuacu ucuaguuuuc auuaaauaau aaagaagccu cauuguuaau aucugcuuuu   1200
ggugucaguu uuaaggaaaa cuaguuucau aucauaaaua aggaaauuau ugucucucuc   1260
aguuccaaca uguuaauuug gguauagaau uucagccaca agcaucccau gaaauuaaug   1320
uauccauacu uuuaacacua guauacuuua ucuucuuauu ucaaaugcuc ugucuccuuc   1380
uguccauuac uuccucuucc ccaagcaauu augagcauuu uuugaauaug ucugaauuuc   1440
uucauuccca uugcccccac ucuaaaugug uagauacuau ugucuccagu uuuaagcaau   1500
ugcuacugac cccuaacuag gcucauagaa auugguuuuc uacaucgaga cagagugacc   1560
cuuaauauuc uuucaccaac acguaaguca guaucauguu cagggaaaaa cugaauagcc   1620
agauucaaag ugggcucugu cacacagguu auuuaggaaa gucacuuaac aucuccugga   1680
uuuaauuuca ucauaugcaa ugaagggauu ggaggagauu auaagaaguc auuucaagug   1740
cuccauuuuu uuaguguuuu ucaaauauau acaaggcuug gcaauauucu uuauauaaug   1800
cuuguauaca uugaaagcaa uguaaauuuu aauucauaac cccaaguaug cuaacuucaa   1860
agaucucauc acuugcuaag guacacuaaa gccuaucacu aaacaauggc aucaaaauca   1920
caugagggua acacaauuau cuacagaaau aucuaguccc auuaccaguu acuccugugc   1980
ucauuugagu uaaacacccu gcaauguaua uagcugucca aaaaaggagu gagcaggug a   2040
```

```
gaaugugaau gcuuuaaugg aguacauuau accuuuaugg cuuuuucaaa aguuagccau   2100

aauaauaaua aauaauauuu ucuuggguuc uauccccaaa uuuaggaucu gucuaaucuc   2160

uuucaaaucc cuccuuugua aaauaggaga uccccagagc agauaggacu aagaaauuuc   2220

acauuauaua auauuccaaa uucauuauua ugacucaagg agaucauuau ucuuaaaaau   2280

ucuguggcuu aguuuuucuc aauaaaaaaa agaguuuagu gauuuguuuc ugaacauagc   2340

agaaggaaua aguuauggaa cauauucugu gugugcuccc uccuguaguc aucuuaacua   2400

ucauauguug uccuaugccu uguuccuguc aaugguuucc aagucucccc uguuuagagc   2460

ucuucaauug cuccuucuga gucguguuga aaucauacau guuccaauaa uugaucaccu   2520

uguugaaaua ggcuaaguac uuucuacugc aauuugagcu auguuuugug auuauaccaa   2580

augcucucuu aaccuuucag uauccucugu ugaguuuuug aaaacucauu ucuuauuaau   2640

gugcccccuc cccuaacugc caacaacuuu caagcaccca agagauucaa auaugauuuu   2700

auggag                                                              2706
```

```
<210> SEQ ID NO 2
<211> LENGTH: 2296
<212> TYPE: RNA
<213> ORGANISM: Mus musculus
<220> FEATURE:
<223> OTHER INFORMATION: GADLOR 1

<400> SEQUENCE: 2

aaauuguuua gaacuguggc acuuuaaaag caccucggca uugaucuacu aacucuagau     60

cucaccucuc ugugcuacuu uuagaguuug uagauggaua cuguccagca gaggagaguc    120

aucuacguuc ugaugucgau uuguuuucag agaucagaca cuugacauuc cuagagugga    180

cugucccuuu aaaauaugaa acaaguaaug gccuacagaa agauuaugau aaaacuuucc    240

aguuuuuugg cuuuucccuu cggcccugac uggaugugua gucuacuucc cacaauccug    300

uauguuacau gguucccuac ccagaccacu cccuuugccc caccccaaaa auggcuacug    360

ggcuuucuca aucaucuugc augccacccc ucgccuucuu uuauguuuca gaguugugug    420

ugaagaauca cauuagugau acuguaugcu uucuuuuaca aucuauuuac guuuacacau    480

auuuauuuuu auauuuacau auuucucauu guuuaccagu uggcaauagu gauauuuugu    540

gagcugacuu uacauuuuac uuccgggauc cauaucauuc aaagcuuuaa ggucuuauua    600

aaggcacuug aagguuuucu ggguguuauu uaugcuuagu guuuuucugu aauggaguug    660

guaauguguc auuguuuccu cuucuaaauu uaaguaacua aauacucuga cagauuccua    720

gagcuuccuu cuaccacuag caggugagcu cugguugugu uacaacaggg cgcauuagcu    780

cuguuuacau cuacuaauuu guuuuuagag uauuguccuu cccaaccaca cuuuccaguu    840

caccugccau cuuucacagg cagcagugag agagguuuac cuuuuaaacu cauauuuuuu    900

uaauguuuuc aauccuagau uucacuuuuc cuuuaguuua aucagucaug gagucuuuug    960

auuauuagca uaugcuugac ucugguuuua auaaaaguua guuuuauuau cauaaaaugu   1020

cucccaguug auaaccuuga auuauuuaga aguagaauau cuaaccacaa auaccuccua   1080

aaauuaaugu guucauacuu caaauaccca uauuuuaucu ugcuucuuau uucaaaggcu   1140

gacucuucug cuugucaguu auuccucaaa aacuccugga aacauuuagg auauaucuaa   1200

auuucuuuau ucuuguugcu cuguucuucc uguguuuagu uagaauuuuc aacuauucag   1260

aaaauuucua cagauuucua auugaguuuu uaauuauuuc ucuacauuga gaaagaauau   1320
```

-continued aucccagggu cuuuuuauua aaggcaaagg cuucauggua ugugagaacc ugaaaagccg 1380
gacuccagcu ugggcaaacu ccuuaccauu ucaauguaau uacaucaugu cccacgaaga 1440
cccuggaaaa gauaaaagcc augcauuuuu aagacuucau uuuggggguug ggaaaagacu 1500 ccguuuacag uuucuauuau gauuuugugu gcuuacauuu ggcaaauuuu accucugacu 1560
ccauacucag guacuuucag agacuuuauu aauuucugag guacagagaa gcaugucaau 1620
aaacacugga uaucauagag uuuuguguau aaaacuuacc cagugaccuc ugcacuuuuu 1680
ugaaucugac aucauccagu uaaguagaug ucacucuucc caggaagaau gaggugagag 1740
ucugacuuuu ggaugggauu caucuucccuc uuagcuuuuu gaggaggcaa ucuuaaugau 1800
aauugauggu auauucucug uuuuauuccu ggguuuagga uacuucuggu gcuuuuaauu 1860
acagguuggg auauuucuaa uauuuucuca aguuccuucu gcagaaucag aggcucccaa 1920
agcagaaaaa cuaauaaaug ucaucuaaac guaguguugc acauacuuug acuugaagga 1980
gagccauauu cucauggagu caaugacaua gucuggggguu ugaaacagag uucauugaug 2040
acuuaagaag aauugaaguc agggcuacug aacaauaucc cccuacugaa ucucuaauua 2100
guacaugcuu ccccacaugu uguugggcgg ggggaggcag ugguuucaaa uucccuuuuc 2160
uuuacauuca uuaggggcuc cuuauuuaug cuguacauau auguguuuca ggaacuaauu 2220
uccuauugaa uaaacaaagc acauuguacu cccauguuuu gugacuauac caagcauagu 2280
cauauuuaac aauccu 2296

<210> SEQ ID NO 3
<211> LENGTH: 2399
<212> TYPE: RNA
<213> ORGANISM: Rattus norvegicus
<220> FEATURE:
<223> OTHER INFORMATION: GADLOR 1

<400> SEQUENCE: 3
aggauucuua aauauccuga cugugauugg uauagucaca aagcauggga guagaaugug 60
cuuuguuuau ucaauaaggu aguuagaucc ugaaacacac acacacgcgc gcgcgcacac 120
acacacacac guacacgcac acacacacac acacacacac acacacacac acacacacac 180
acuuaaauca gaaggagcac cugaugaguc uaaagaagag agaauuugga accacugccu 240
uccccaaaac aauguguaga auagcgcaua caaauuagag auucaguagg agauauaacu 300
caguaacccu cacuccaauc uuuccauaac ucaucaauga acucuguuuc aaaacccaca 360
cuaagucacu gaauccuuga gaauguggcu cucccuuaaag ucaaacugau caucuguaau 420
acuaugcuua gacgaaacuu auuaguuguu ucugcuuugg gagucucuga uucugcagaa 480
ggaacuugag aaauauuaga aauaccccuc accugugauu aaagccaucu gaaauauccu 540
aaaccggaaa auaaaacaaa gaacauagca ucaauuaucg uuauaauugc cuccucacaa 600
ugcuaugauu aagauuaauu ucaucaaaaa gucaaaaugc ucuccucauu cuuacuggga 660
acagugacgg cuacaccacu ggaagauguc agauucaaac aagagcagag gucaccgggu 720
aggauuuuua cacacaaaac ccuaugauau cuaauguuua uugacacaau uuccuguauc 780
ccacaaauua ggaaguaccu gccuauggag acagagguaa aauuugccaa aguuaagcau 840
acaaaaauca uuguacaaaa uguaagcaga gucuuagaca acccaaaaug cacugaaaaa 900
auguauugca agugugugguu uuuuaucuuu uccaaugucu ucacugcaca ugauguaauu 960
aaaucacaau gauaagugag uuucccaagg aaggggguguc acaguccaag cuggacucug 1020
acuuuucaga uuuuugccac agaccaugcu gacuggguau aauaaaaaga ccuugagacu 1080

-continued ugcucugccu caauguagag aaauaauuau ugucaacuca auuagagguc aguauaaauu 1140
uucugaauga uugaaaaucu uacacauaga aaagccagag caacaagaau aaugaaaauu 1200
aguuauaucc uaaacauguc cacgaguguu ugaagaauaa cgaacaagcg gaagagucag 1260
ccuuugaaau aagaaacgag auaaaauaug gguauuugaa guaugaacac auuaauuuua 1320
ggggauauuu gugguuagau auucuacuuc uaaauaauuu aagguucuca acugggagag 1380
cuauuaugau aauaaagcua auuuuuauua aaaccaaagu caagcauaua uuaauaauca 1440
aaagacuuua ugauuaauua aaccgaggga aaaguaaaau ggaggaaugg aaacauuaaa 1500
aaagaugagu uuaaaaggua auccucuuac ugcugccuuu gaaagaugcu gggugaacgg 1560
ggaaguaggg uugggaaggg cuagacucua aaaacagauu gauagggcua agcagagcug 1620
aagcuucaug gaacagaauu ggagccuagu gguagaagga agaagccaua ggaauccuuc 1680
agaguguuuu gcuacuuaaa uuuagaaaag gaaacaauca uagguuggca acacuauuac 1740
agaaauaaag aggcaagcau aaaugacaca cagcaagccu uaugaugccc uuaauaagac 1800
cuuaaagcuu ugaaugcaug uggaaccagg aagcaaagag uaaagacaga gcucacaaac 1860
ugucauuauu uccaacuggu aaagaauaag gaauacaugg aagcagaagg gaaauauaaa 1920
acgaaauaag uauauguaaa uagauuguaa aagaaagcag acaguaucac uaaaugugau 1980
auuucaaaca caacuuugaa auacaaaaga aggccaggag uggcaugcaa gaugauugag 2040
aaagccuagu agacguuccu agggugggc aaagagaacg aacuggguag aaaaccaugu 2100
aacccauagg auugugggaa ggagaauaua cauccuccca gggucaaagg ggaaagccaa 2160
gaaacuagag aguuuuacca uagucuuucu gaaggcuauu acuuguuuca uauuuuuaag 2220
ggacaaucua aggaugucaa gugucugaua ucuaaaauca aauugacaau ggaauguaga 2280
ugacucaccu cugcuggaca guauccaucu acaaacucua aaaguaacac agaggugaga 2340
ccuagaguua guagaucaau gccgaugugc uuuuaaacug ccacaguucu aaacaauuu 2399

<210> SEQ ID NO 4
<211> LENGTH: 615
<212> TYPE: RNA
<213> ORGANISM: Homo sapiens
<220> FEATURE:
<223> OTHER INFORMATION: GADLOR 2

<400> SEQUENCE: 4
auuuauaacu gcaauagaaa auggaaugac uauugauuau uuuuuaguua cccaaacuaa 60
uugucauaua aagcuuugua aaucuuuuaa aaugaguaug gguguaaauu aaaaacgaau 120
uaaagcagag gcuuauaaag acacuaucuc cccuucaaug gguuauguau uuuuguugug 180
uguuaggaag auaucucuug aucuccacac ccaaaacucc uuccaaauga acaaaggccu 240
acacacaaaa auuauuucaa uugcuaauag ccaguuuuua uuuuucaaaa guaaaugcuu 300
ucuuuuuuug aaaaguaaau auaacuauuu uaacaaagua agauuuaaaa aaaaaaacaa 360
cucagaaaaa agugccaugc agagauaaca gggcugaucu gucuguuauc ugcagccucu 420
auccuuacug uuaacaagcc uuuuaucuuu gaagacacua aacaucuggg aucuaagcac 480
ugacaccuau uaguuacagu gguuuccuuu uaccuuucua aacuaucuga uagauaaacc 540
uccaggaauc cuacaaaauu aggcccuuaa uugaccaaac gaaugucugu cucucuuuuu 600
caaucuaaau caaaa 615

<210> SEQ ID NO 5

-continued

<211> LENGTH: 1393
<212> TYPE: RNA
<213> ORGANISM: Mus musculus
<220> FEATURE:
<223> OTHER INFORMATION: GADLOR 2

<400> SEQUENCE: 5

```
ucugcaucug ugguuguuuu aacuguaugc augaagaaua aaauuuggac agugcacaca     60

uaggacuugc agggacucac agugugucau auuuugcacu uuuuaugaau guugauaugu    120

uuucagaaua auuuauaacu gcaauugaaa acugaauggc uauugauuaa auuuuaguuu    180

caaaaacuaa uugacauaua aagcuucaua aauccuuuua gaaaaggaug aguauaaauu    240

aaaaacuaau uacagcaaag gcuuauaaaa uacuccaauu ccaguucuau gguuauauac    300

uguuguaugc uaugaaggug uuccuuuguc uucuuaauca aaacuccugc cauagaauua    360

aauaugaacc auaaaagaua uuuuaauugc uaaugauuac uuuauauaua guaucccuuu    420

ucaagagagu uuauaagaau uuuuaaucag uaauauuuaa aaauuuaaaa aagaacagaa    480

gugggccaug uuaaggcagc agaaccaauu gccaguuauc uguaaccucu auccuugaug    540

cuaauaagcc uuuuaccuuc gaagacacua agcaucuggg aucuaaguag ugacaccuau    600

uaguuacaau gguuuccuuu uaccuucuaa gcaaucugau agauaaaccu ccaggaaucc    660

cacaaaauug gacccuuaau ugaccaaaug aauggcuguc ucucuuuuac aguauaaauu    720

gaaaagugag uuugcuccca ugagguaaga cauaacuuag gaaagaaauc acgcugagac    780

uccacuugcc acauuagugu gcccuuguaa ucucaccaaa agccacccac caacaguagg    840

acaaagugau ucuucuaaaa cgcacaucgu ucuucaaaug auucaucuca auuucaucuu    900

caccaucacu uuagaaacau gccugaaacc acauuuauuu uaaagaguuu uaaguaacau    960

uugaggauca ccugauauaa uagagaauac ucuuuucaag caauauagca gcagagaagg   1020

uagcuaaaga ggguguucug agauuuuuuu uuuuuccugu gugacuuccu uucaaauacu   1080

gggaaauaug aaguauuuua aaggcaaucu gugaaauagc aauuuuauau guaguauggu   1140

uauucuuuuu gucuacacuu cuuuaaguac uaaacauacu agaaauuaua auucauaugc   1200

aauggcaaua ugagaauuua cauacuucaa auaaaaacaa uuuaaauuca uuuaaaaaaa   1260

ccaauucaau uacaauuaag uaacugggua auauuuucac aaaaauccau uaaaucauau   1320

ucuuucauua aaauaguuua uacauuuuua auacaaauga aaaacagaac caaagagaua   1380

auaaaauagc agc                                                      1393
```

<210> SEQ ID NO 6
<211> LENGTH: 1364
<212> TYPE: RNA
<213> ORGANISM: Rattus norvegicus
<220> FEATURE:
<223> OTHER INFORMATION: GADLOR 2

<400> SEQUENCE: 6

```
gcugcuaugu uauuaucucu uucgcucugu uuuucauuug uauuaaaaau guauaaacua     60

uuuuaaugaa agaauaugau uuaauggauu uuuugugaaa auauuacaca gucacuuaau    120

uguaauugaa uuggguuuuu uuuuaaauga auuuaaauug uuuuuauuug aagucuguaa    180

auucucauau ugccauugca uaggaauuau gauuucuagu auguuuagga cuuaaagaag    240

uauagaccaa aaaauacagc aauaguacac uuaaaguugg cacuuuacag auugccuuua    300

aaauacauaa guucucccag uauuugcaag gaaguuacac aggaaaacgu cucucagaau    360

aagcucucua acuaccuucu cugcugcuac auucccugaa aaguguauuc ucuagaucag    420
```

-continued augauuuuca auugauacuc aaaccucuaa aacaaaugug auuucaggga ugugucuaag 480
gugaugcuga agauaaaauu gagaugaauc auuugaagaa agauguaggu uuuagaggaa 540
ccacuuuuuu ucugcuguug guugauggcu uuuggcgaga ucauaaggac acacuaaugu 600
gacaagggga gucgcagcau gauauccuuc cuaagguaug ccuugccuca ugggagcaaa 660
cucacuuuuc aauuuauacu guaaaagaga gacagccauu cauuugguca auuaagggcc 720
caauuuugua ggauuccugg aggguuaucu aucagauugc ucagaaggga aaagaaacca 780
uuguaacuaa uaggugucac uacuuagauc ccagauguuu agugucuucg aagguaaaag 840
gcuuauuaac cucaagaaaa gagguuacag auaacugaca gucgguucug cugccuuaac 900
auaguccacg uuuguucuuu cuuuuauuuu uuaaauauua cugauuuaaa acacuuauac 960
ucuuuucaaa aaauucugua uguaaucuaa ucauuagcaa uuaaauaauu uuuauuucua 1020
auauuugauc cuauggcagg aauuugggau aaaggagcua aaggaccaca uccauaguau 1080
acaaaaguau auaaacaugg cacuggaauu ggaguguuuu auaagccuuu gcuguaauua 1140
guuuuuaauu uauacucauc cucuucuaaa aggauuuaug aagcuuuaua ugucaauuca 1200
uuuuugaaac uaaaauuuaa ucaauaguca uucaguuuua aauugcaguu auaaauucuu 1260
cugaaaacau aucaacaauc auaaaaagca gauauuguga cacaauauga gucccugcaa 1320
auucuaugug ugcauugucc aaaguuucau cuucaugcau ccaa 1364

<210> SEQ ID NO 7
<211> LENGTH: 21
<212> TYPE: RNA
<213> ORGANISM: Homo sapiens
<220> FEATURE:
<223> OTHER INFORMATION: human GADLOR 1 target sequence

<400> SEQUENCE: 7
ggauacuagg cuuaggacau a 21

<210> SEQ ID NO 8
<211> LENGTH: 16
<212> TYPE: RNA
<213> ORGANISM: Mus musculus
<220> FEATURE:
<223> OTHER INFORMATION: mouse GADLOR 1 target sequence

<400> SEQUENCE: 8
ucucaaucau cuugca 16

<210> SEQ ID NO 9
<211> LENGTH: 16
<212> TYPE: RNA
<213> ORGANISM: Homo sapiens
<220> FEATURE:
<223> OTHER INFORMATION: human GADLOR 2 target sequence

<400> SEQUENCE: 9
agccucuauc cuuacu 16

<210> SEQ ID NO 10
<211> LENGTH: 15
<212> TYPE: RNA
<213> ORGANISM: Mus musculus
<220> FEATURE:
<223> OTHER INFORMATION: mouse GADLOR 2 target sequence

<400> SEQUENCE: 10

-continued aaccucuauc cuuga 15

<210> SEQ ID NO 11
<211> LENGTH: 24
<212> TYPE: DNA
<213> ORGANISM: Artificial Sequence
<220> FEATURE:
<223> OTHER INFORMATION: qPCR forward primer for GADLOR 1

<400> SEQUENCE: 11
ttacatggtt ccctacccag acca 24

<210> SEQ ID NO 12
<211> LENGTH: 24
<212> TYPE: DNA
<213> ORGANISM: Artificial Sequence
<220> FEATURE:
<223> OTHER INFORMATION: qPCR reverse primer for GADLOR 1

<400> SEQUENCE: 12
gggtggcatg caagatgatt gaga 24

<210> SEQ ID NO 13
<211> LENGTH: 20
<212> TYPE: DNA
<213> ORGANISM: Artificial Sequence
<220> FEATURE:
<223> OTHER INFORMATION: qPCR forward primer for GADLOR 2

<400> SEQUENCE: 13
aggacttgca gggactcaca 20

<210> SEQ ID NO 14
<211> LENGTH: 22
<212> TYPE: DNA
<213> ORGANISM: Artificial Sequence
<220> FEATURE:
<223> OTHER INFORMATION: qPCR reverse primer for GADLOR 2

<400> SEQUENCE: 14
tcaatagcca ttcagttttc aa 22

<210> SEQ ID NO 15
<211> LENGTH: 19
<212> TYPE: DNA
<213> ORGANISM: Artificial Sequence
<220> FEATURE:
<223> OTHER INFORMATION: qPCR forward primer for mouse specific GADLOR 1

<400> SEQUENCE: 15
agcttgggca aactcctta 19

<210> SEQ ID NO 16
<211> LENGTH: 21
<212> TYPE: DNA
<213> ORGANISM: Artificial Sequence
<220> FEATURE:
<223> OTHER INFORMATION: qPCR reverse primer for mouse specific GADLOR 1

<400> SEQUENCE: 16
gaagtcttaa aaatgcatgg c 21

<210> SEQ ID NO 17
<211> LENGTH: 21
<212> TYPE: DNA
<213> ORGANISM: Artificial Sequence
<220> FEATURE:
<223> OTHER INFORMATION: qPCR forward primer for mouse specific GADLOR 2

<400> SEQUENCE: 17
cacagtgtgt catattttgc a 21

<210> SEQ ID NO 18
<211> LENGTH: 20
<212> TYPE: DNA
<213> ORGANISM: Artificial Sequence
<220> FEATURE:
<223> OTHER INFORMATION: qPCR reverse primer for mouse specific GADLOR 2

<400> SEQUENCE: 18
caaaggaaca ccttcatagc 20

<210> SEQ ID NO 19
<211> LENGTH: 15
<212> TYPE: DNA
<213> ORGANISM: Artificial Sequence
<220> FEATURE:
<223> OTHER INFORMATION: LNA long RNA GapmeR scramble control

<400> SEQUENCE: 19
aacacgtcta tacgc 15

<210> SEQ ID NO 20
<211> LENGTH: 16
<212> TYPE: DNA
<213> ORGANISM: Artificial Sequence
<220> FEATURE:
<223> OTHER INFORMATION: LNA long RNA GapmeR targeting GADLOR 1

<400> SEQUENCE: 20
tgcaagatga ttgaga 16

<210> SEQ ID NO 21
<211> LENGTH: 15
<212> TYPE: DNA
<213> ORGANISM: Artificial Sequence
<220> FEATURE:
<223> OTHER INFORMATION: LNA long RNA GapmeR targeting GADLOR 2

<400> SEQUENCE: 21
tcaaggatag aggtt 15

<210> SEQ ID NO 22
<211> LENGTH: 19
<212> TYPE: DNA
<213> ORGANISM: Artificial Sequence
<220> FEATURE:
<223> OTHER INFORMATION: qPCR forward primer for mouse Gapdh

<400> SEQUENCE: 22
ccgcatcttc ttgtgcagt 19

<210> SEQ ID NO 23
<211> LENGTH: 20
<212> TYPE: DNA
<213> ORGANISM: Artificial Sequence
<220> FEATURE:
<223> OTHER INFORMATION: qPCR reverse primer for mouse Gapdh

<400> SEQUENCE: 23
catcacctgg cctacaggat 20

-continued

<210> SEQ ID NO 24
<211> LENGTH: 24
<212> TYPE: DNA
<213> ORGANISM: Artificial Sequence
<220> FEATURE:
<223> OTHER INFORMATION: qPCR forward primer for mouse ?-MHC

<400> SEQUENCE: 24
aggcaaggca aagaaaggct catc 24

<210> SEQ ID NO 25
<211> LENGTH: 24
<212> TYPE: DNA
<213> ORGANISM: Artificial Sequence
<220> FEATURE:
<223> OTHER INFORMATION: qPCR reverse primer for mouse ?-MHC

<400> SEQUENCE: 25
gcgtggagcg caagtttgtc ataa 24

<210> SEQ ID NO 26
<211> LENGTH: 18
<212> TYPE: DNA
<213> ORGANISM: Artificial Sequence
<220> FEATURE:
<223> OTHER INFORMATION: qPCR forward primer for mouse ?-MHC

<400> SEQUENCE: 26
actgtggtgc ctcgttcc 18

<210> SEQ ID NO 27
<211> LENGTH: 20
<212> TYPE: DNA
<213> ORGANISM: Artificial Sequence
<220> FEATURE:
<223> OTHER INFORMATION: qPCR reverse primer for mouse ?-MHC

<400> SEQUENCE: 27
gcctctaggc gttccttctc 20

<210> SEQ ID NO 28
<211> LENGTH: 24
<212> TYPE: DNA
<213> ORGANISM: Artificial Sequence
<220> FEATURE:
<223> OTHER INFORMATION: qPCR forward primer for mouse SERCA2a

<400> SEQUENCE: 28
acgtgcctgg tggagaagat gaat 24

<210> SEQ ID NO 29
<211> LENGTH: 24
<212> TYPE: DNA
<213> ORGANISM: Artificial Sequence
<220> FEATURE:
<223> OTHER INFORMATION: qPCR reverse primer for mouse SERCA2a

<400> SEQUENCE: 29
atcttgctca tggatgtccg gctt 24

<210> SEQ ID NO 30
<211> LENGTH: 20
<212> TYPE: DNA
<213> ORGANISM: Artificial Sequence
<220> FEATURE:
<223> OTHER INFORMATION: qPCR forward primer for mouse Gata2

<400> SEQUENCE: 30
gcacctgttg tgcaaattgt 20

<210> SEQ ID NO 31
<211> LENGTH: 19
<212> TYPE: DNA
<213> ORGANISM: Artificial Sequence
<220> FEATURE:
<223> OTHER INFORMATION: qPCR reverse primer for mouse Gata2

<400> SEQUENCE: 31
agggcggtga cttctcttg 19

<210> SEQ ID NO 32
<211> LENGTH: 24
<212> TYPE: DNA
<213> ORGANISM: Artificial Sequence
<220> FEATURE:
<223> OTHER INFORMATION: qPCR forward primer for mouse BNP

<400> SEQUENCE: 32
ctcaagctgc tttgggcaca agat 24

<210> SEQ ID NO 33
<211> LENGTH: 24
<212> TYPE: DNA
<213> ORGANISM: Artificial Sequence
<220> FEATURE:
<223> OTHER INFORMATION: qPCR reverse primer for mouse BNP

<400> SEQUENCE: 33
agccaggagg tcttcctaca acaa 24

<210> SEQ ID NO 34
<211> LENGTH: 21
<212> TYPE: DNA
<213> ORGANISM: Artificial Sequence
<220> FEATURE:
<223> OTHER INFORMATION: qPCR forward primer for mouse RCAN1.4

<400> SEQUENCE: 34
gcttgactga gagagcgagt c 21

<210> SEQ ID NO 35
<211> LENGTH: 21
<212> TYPE: DNA
<213> ORGANISM: Artificial Sequence
<220> FEATURE:
<223> OTHER INFORMATION: qPCR reverse primer for mouse RCAN1.4

<400> SEQUENCE: 35
ccacacaagc aatcagggag c 21

<210> SEQ ID NO 36
<211> LENGTH: 27
<212> TYPE: DNA
<213> ORGANISM: Artificial Sequence
<220> FEATURE:
<223> OTHER INFORMATION: ChIP assay forward primer 1 for GADLOR 1

<400> SEQUENCE: 36
caattacaaa cactgaagta acaattt 27

<210> SEQ ID NO 37

-continued

<211> LENGTH: 20
<212> TYPE: DNA
<213> ORGANISM: Artificial Sequence
<220> FEATURE:
<223> OTHER INFORMATION: ChIP assay reverse primer 1 for GADLOR 1

<400> SEQUENCE: 37
gccctcttct ggcctctaaa 20

<210> SEQ ID NO 38
<211> LENGTH: 20
<212> TYPE: DNA
<213> ORGANISM: Artificial Sequence
<220> FEATURE:
<223> OTHER INFORMATION: ChIP assay forward primer 2 for GADLOR 1

<400> SEQUENCE: 38
ggctgagcca tttcatctct 20

<210> SEQ ID NO 39
<211> LENGTH: 20
<212> TYPE: DNA
<213> ORGANISM: Artificial Sequence
<220> FEATURE:
<223> OTHER INFORMATION: ChIP assay reverse primer 2 for GADLOR 1

<400> SEQUENCE: 39
tatccacgtg cactcacaca 20

<210> SEQ ID NO 40
<211> LENGTH: 20
<212> TYPE: DNA
<213> ORGANISM: Artificial Sequence
<220> FEATURE:
<223> OTHER INFORMATION: ChIP assay forward primer 3 for GADLOR 1

<400> SEQUENCE: 40
atttgttcgg tttggcaatg 20

<210> SEQ ID NO 41
<211> LENGTH: 21
<212> TYPE: DNA
<213> ORGANISM: Artificial Sequence
<220> FEATURE:
<223> OTHER INFORMATION: ChIP assay reverse primer 3 for GADLOR 1

<400> SEQUENCE: 41
gacggctcaa gaggtaagct a 21

<210> SEQ ID NO 42
<211> LENGTH: 20
<212> TYPE: DNA
<213> ORGANISM: Artificial Sequence
<220> FEATURE:
<223> OTHER INFORMATION: ChIP assay forward primer 4 for GADLOR 1

<400> SEQUENCE: 42
gagacaggca cccagaagac 20

<210> SEQ ID NO 43
<211> LENGTH: 20
<212> TYPE: DNA
<213> ORGANISM: Artificial Sequence
<220> FEATURE:
<223> OTHER INFORMATION: ChIP assay reverse primer 4 for GADLOR 1

<400> SEQUENCE: 43
cacacccctc ttttgctttc 20

<210> SEQ ID NO 44
<211> LENGTH: 20
<212> TYPE: DNA
<213> ORGANISM: Artificial Sequence
<220> FEATURE:
<223> OTHER INFORMATION: ChIP assay forward primer 5 for GADLOR 1

<400> SEQUENCE: 44
ctcacctctt cctggctcac 20

<210> SEQ ID NO 45
<211> LENGTH: 20
<212> TYPE: DNA
<213> ORGANISM: Artificial Sequence
<220> FEATURE:
<223> OTHER INFORMATION: ChIP assay reverse primer 5 for GADLOR 1

<400> SEQUENCE: 45
tcccttttcc attcctctca 20

<210> SEQ ID NO 46
<211> LENGTH: 20
<212> TYPE: DNA
<213> ORGANISM: Artificial Sequence
<220> FEATURE:
<223> OTHER INFORMATION: ChIP assay forward primer 1 for GADLOR 2

<400> SEQUENCE: 46
ttccttgctg ggtatcttgg 20

<210> SEQ ID NO 47
<211> LENGTH: 20
<212> TYPE: DNA
<213> ORGANISM: Artificial Sequence
<220> FEATURE:
<223> OTHER INFORMATION: ChIP assay reverse primer 1 for GADLOR 2

<400> SEQUENCE: 47
gccctcttct ggcctctaaa 20

<210> SEQ ID NO 48
<211> LENGTH: 20
<212> TYPE: DNA
<213> ORGANISM: Artificial Sequence
<220> FEATURE:
<223> OTHER INFORMATION: ChIP assay forward primer 2 for GADLOR 2

<400> SEQUENCE: 48
cgtggcagca agttaaatca 20

<210> SEQ ID NO 49
<211> LENGTH: 20
<212> TYPE: DNA
<213> ORGANISM: Artificial Sequence
<220> FEATURE:
<223> OTHER INFORMATION: ChIP assay reverse primer 2 for GADLOR 2

<400> SEQUENCE: 49
ctgtggcagt gttgcctcta 20

<210> SEQ ID NO 50
<211> LENGTH: 24
<212> TYPE: DNA

<213> ORGANISM: Artificial Sequence
<220> FEATURE:
<223> OTHER INFORMATION: ChIP assay forward primer 3 for GADLOR 2

<400> SEQUENCE: 50
tttgcatttc tgatacttac tgga 24

<210> SEQ ID NO 51
<211> LENGTH: 21
<212> TYPE: DNA
<213> ORGANISM: Artificial Sequence
<220> FEATURE:
<223> OTHER INFORMATION: ChIP assay reverse primer 3 for GADLOR 2

<400> SEQUENCE: 51
cgaggtcatt gaaatcgctt a 21

<210> SEQ ID NO 52
<211> LENGTH: 20
<212> TYPE: DNA
<213> ORGANISM: Artificial Sequence
<220> FEATURE:
<223> OTHER INFORMATION: ChIP assay forward primer 4 for GADLOR 2

<400> SEQUENCE: 52
ggagaccgag atcaagcaaa 20

<210> SEQ ID NO 53
<211> LENGTH: 20
<212> TYPE: DNA
<213> ORGANISM: Artificial Sequence
<220> FEATURE:
<223> OTHER INFORMATION: ChIP assay reverse primer 4 for GADLOR 2

<400> SEQUENCE: 53
tggtcctttg aaccctcatt 20

<210> SEQ ID NO 54
<211> LENGTH: 22
<212> TYPE: DNA
<213> ORGANISM: Artificial Sequence
<220> FEATURE:
<223> OTHER INFORMATION: ChIP assay forward primer 5 for GADLOR 2

<400> SEQUENCE: 54
ttgaagatgt tgcaaacaag aa 22

<210> SEQ ID NO 55
<211> LENGTH: 20
<212> TYPE: DNA
<213> ORGANISM: Artificial Sequence
<220> FEATURE:
<223> OTHER INFORMATION: ChIP assay reverse primer 5 for GADLOR 2

<400> SEQUENCE: 55
aggtgaagtg ggatttgtgc 20

<210> SEQ ID NO 56
<211> LENGTH: 24
<212> TYPE: DNA
<213> ORGANISM: Artificial Sequence
<220> FEATURE:
<223> OTHER INFORMATION: RIP assay forward primer for GADLOR 1

<400> SEQUENCE: 56
ttacatggtt ccctacccag acca 24

<210> SEQ ID NO 57
<211> LENGTH: 24
<212> TYPE: DNA
<213> ORGANISM: Artificial Sequence
<220> FEATURE:
<223> OTHER INFORMATION: RIP assay reverse primer for GADLOR 1

<400> SEQUENCE: 57
gggtggcatg caagatgatt gaga 24

<210> SEQ ID NO 58
<211> LENGTH: 20
<212> TYPE: DNA
<213> ORGANISM: Artificial Sequence
<220> FEATURE:
<223> OTHER INFORMATION: RIP assay forward primer for GADLOR 2

<400> SEQUENCE: 58
aggacttgca gggactcaca 20

<210> SEQ ID NO 59
<211> LENGTH: 22
<212> TYPE: DNA
<213> ORGANISM: Artificial Sequence
<220> FEATURE:
<223> OTHER INFORMATION: RIP assay reverse primer for GADLOR 2

<400> SEQUENCE: 59
tcaatagcca ttcagttttc aa 22

<210> SEQ ID NO 60
<211> LENGTH: 20
<212> TYPE: DNA
<213> ORGANISM: Artificial Sequence
<220> FEATURE:
<223> OTHER INFORMATION: GADLOR 1 forward primer

<400> SEQUENCE: 60
aatttcagcc acaagcatcc 20

<210> SEQ ID NO 61
<211> LENGTH: 20
<212> TYPE: DNA
<213> ORGANISM: Artificial Sequence
<220> FEATURE:
<223> OTHER INFORMATION: GADLOR 1 reverse primer

<400> SEQUENCE: 61
tgcttgggga agaggaagta 20

<210> SEQ ID NO 62
<211> LENGTH: 21
<212> TYPE: DNA
<213> ORGANISM: Artificial Sequence
<220> FEATURE:
<223> OTHER INFORMATION: GADLOR 2 forward primer

<400> SEQUENCE: 62
tgggatctaa gcactgacac c 21

<210> SEQ ID NO 63
<211> LENGTH: 22
<212> TYPE: DNA
<213> ORGANISM: Artificial Sequence
<220> FEATURE:

-continued

```
<223> OTHER INFORMATION: GADLOR 2 reverse primer

<400> SEQUENCE: 63

gagacagaca ttcgtttggt ca                                              22
```